(12) United States Patent
Glerum et al.

(10) Patent No.: US 9,351,848 B2
(45) Date of Patent: May 31, 2016

(54) EXPANDABLE FUSION DEVICE AND METHOD OF INSTALLATION THEREOF

(71) Applicant: GLOBUS MEDICAL INC., Audubon, PA (US)

(72) Inventors: Chad Glerum, Pennsburg, PA (US); Andrew Iott, Newton Square, PA (US); Mark Adams, Downingtown, PA (US)

(73) Assignee: Globus Medical, Inc., Audubon, PA (US)

( * ) Notice: Subject to any disclaimer, the term of this patent is extended or adjusted under 35 U.S.C. 154(b) by 2 days.

(21) Appl. No.: 13/793,481

(22) Filed: Mar. 11, 2013

(65) Prior Publication Data

US 2014/0039622 A1   Feb. 6, 2014

Related U.S. Application Data

(63) Continuation-in-part of application No. 12/875,637, filed on Sep. 3, 2010, now Pat. No. 8,845,731.

(51) Int. Cl.
*A61F 2/44* (2006.01)
*A61F 2/46* (2006.01)
(Continued)

(52) U.S. Cl.
CPC .............. *A61F 2/447* (2013.01); *A61F 2/442* (2013.01); *A61F 2/4465* (2013.01); *A61F 2/4611* (2013.01); *A61F 2002/2817* (2013.01); *A61F 2002/2835* (2013.01); *A61F 2002/3056* (2013.01); *A61F 2002/3083* (2013.01); *A61F 2002/30266* (2013.01); *A61F 2002/30387* (2013.01); *A61F 2002/30397* (2013.01); *A61F 2002/30405* (2013.01); *A61F 2002/30411* (2013.01); *A61F 2002/30415* (2013.01); *A61F 2002/30471* (2013.01); *A61F 2002/30472* (2013.01); *A61F 2002/30482* (2013.01); *A61F 2002/30484* (2013.01); *A61F 2002/30517* (2013.01); *A61F 2002/30522* (2013.01); *A61F 2002/30523* (2013.01); *A61F 2002/30538* (2013.01); *A61F 2002/30555* (2013.01); *A61F 2002/30556* (2013.01); *A61F 2002/30579* (2013.01); *A61F 2002/30601* (2013.01); *A61F 2002/30607* (2013.01); *A61F 2002/30828* (2013.01); *A61F 2002/30841* (2013.01); *A61F 2002/30843* (2013.01); *A61F 2002/30904* (2013.01); *A61F 2002/4475* (2013.01);
(Continued)

(58) Field of Classification Search
CPC ...................................................... A61F 2/447
See application file for complete search history.

(56) References Cited

U.S. PATENT DOCUMENTS 4,349,921 A   9/1982   Kuntz
4,599,086 A   7/1986   Doty
(Continued)

FOREIGN PATENT DOCUMENTS

DE   4012622 C1   7/1991
DE   4327054 C1   4/1995
(Continued)

*Primary Examiner* — Jan Christopher Merene

(57) ABSTRACT

The present invention provides an expandable fusion device capable of being installed inside an intervertebral disc space to maintain normal disc spacing and restore spinal stability, thereby facilitating an intervertebral fusion. In an exemplary embodiment, the present invention provides an intervertebral implant. The intervertebral implant may be configured to transition from a collapsed configuration having a first height and a first width to an expanded configuration having a second height and a second width.

19 Claims, 45 Drawing Sheets

(51) Int. Cl.
*A61F 2/28* (2006.01)
*A61F 2/30* (2006.01)

(52) U.S. Cl.
CPC .......... *A61F 2310/00011* (2013.01); *A61F 2310/00017* (2013.01); *A61F 2310/00023* (2013.01); *A61F 2310/00179* (2013.01)

(56) References Cited

U.S. PATENT DOCUMENTS

| | | | |
|---|---|---|---|
| 4,863,476 A | 9/1989 | Shepperd | |
| 4,863,477 A | 9/1989 | Monson | |
| 5,123,926 A | 6/1992 | Pisharodi | |
| 5,290,312 A | 3/1994 | Kojimoto et al. | |
| 5,306,310 A | 4/1994 | Siebels | |
| 5,375,823 A | 12/1994 | Navas | |
| 5,390,683 A | 2/1995 | Pisharodi | |
| 5,522,899 A | 6/1996 | Michelson | |
| 5,534,030 A | 7/1996 | Navarro et al. | |
| 5,554,191 A | 9/1996 | Lahille et al. | |
| 5,571,192 A | 11/1996 | Schonhoffer | |
| 5,645,596 A | 7/1997 | Kim | |
| 5,653,763 A | 8/1997 | Errico et al. | |
| 5,665,122 A | 9/1997 | Kambin | |
| 5,676,701 A | 10/1997 | Yuan et al. | |
| 5,697,977 A | 12/1997 | Pisharodi | |
| 6,039,761 A | 3/2000 | Li et al. | |
| 6,045,579 A | 4/2000 | Hochshuler et al. | |
| 6,080,193 A | 6/2000 | Hochshuler | |
| 6,099,531 A | 8/2000 | Bonutti | |
| 6,126,689 A | 10/2000 | Brett | |
| 6,176,882 B1 | 1/2001 | Biedermann | |
| 6,200,347 B1* | 3/2001 | Anderson et al. | 623/16.11 |
| 6,258,125 B1 | 7/2001 | Paul et al. | |
| 6,436,140 B1 | 8/2002 | Liu | |
| 6,554,863 B2 | 4/2003 | Paul et al. | |
| 6,558,423 B1 | 5/2003 | Michelson | |
| 6,558,424 B2 | 5/2003 | Thalgott | |
| 6,562,074 B2 | 5/2003 | Gerbec et al. | |
| 6,576,016 B1 | 6/2003 | Hochshuler et al. | |
| 6,641,614 B1 | 11/2003 | Wagner et al. | |
| 6,648,917 B2 | 11/2003 | Gerbec et al. | |
| 6,666,891 B2 | 12/2003 | Boehm, Jr. et al. | |
| 6,692,495 B1 | 2/2004 | Zacouto | |
| 6,706,070 B1 | 3/2004 | Wagner et al. | |
| 6,752,832 B2 | 6/2004 | Neumann | |
| 6,773,460 B2 | 8/2004 | Jackson | |
| 6,814,756 B1 | 11/2004 | Michelson | |
| 6,830,589 B2 | 12/2004 | Erickson | |
| 6,849,093 B2 | 2/2005 | Michelson | |
| 6,852,129 B2 | 2/2005 | Gerbec et al. | |
| 6,863,673 B2 | 3/2005 | Gerbec et al. | |
| 6,881,228 B2 | 4/2005 | Zdeblick et al. | |
| 7,018,415 B1 | 3/2006 | McKay | |
| 7,070,598 B2 | 7/2006 | Lim et al. | |
| 7,204,853 B2 | 4/2007 | Gordon | |
| 7,217,291 B2 | 5/2007 | Zucherman et al. | |
| 7,217,293 B2* | 5/2007 | Branch, Jr. | 623/17.16 |
| 7,282,063 B2 | 10/2007 | Cohen et al. | |
| 7,316,714 B2 | 1/2008 | Gordon | |
| 7,473,276 B2 | 1/2009 | Aebi et al. | |
| 7,531,002 B2 | 5/2009 | Sutton | |
| 7,547,325 B2 | 6/2009 | Biedermann et al. | |
| 7,621,953 B2 | 11/2009 | Braddock, Jr. et al. | |
| 7,621,960 B2 | 11/2009 | Boyd | |
| 7,641,693 B2 | 1/2010 | Gutlin et al. | |
| 7,682,396 B2 | 3/2010 | Beaurain et al. | |
| 7,727,280 B2 | 6/2010 | McLuen | |
| 7,744,649 B2 | 6/2010 | Moore | |
| 7,749,270 B2 | 7/2010 | Peterman | |
| 7,753,958 B2 | 7/2010 | Gordon | |
| 7,771,473 B2 | 8/2010 | Thramann | |
| 7,780,732 B2 | 8/2010 | Abernathie | |
| 7,799,081 B2 | 9/2010 | McKinley | |
| 7,811,287 B2 | 10/2010 | Errico | |
| 7,815,683 B2 | 10/2010 | Melkent et al. | |
| 7,828,849 B2 | 11/2010 | Lim | |
| 7,837,734 B2 | 11/2010 | Zucherman et al. | |
| 7,850,733 B2 | 12/2010 | Baynham | |
| 7,875,076 B2 | 1/2011 | Mathieu | |
| 7,875,078 B2 | 1/2011 | Wysocki et al. | |
| 7,879,098 B1* | 2/2011 | Simmons, Jr. | 623/17.11 |
| 7,892,239 B2 | 2/2011 | Warnick | |
| 7,901,409 B2 | 3/2011 | Canaveral et al. | |
| 7,909,869 B2 | 3/2011 | Gordon | |
| 7,951,199 B2 | 5/2011 | Miller | |
| 7,959,675 B2 | 6/2011 | Gately | |
| 7,976,549 B2 | 7/2011 | Dye | |
| 7,988,695 B2 | 8/2011 | Dye | |
| 8,043,293 B2 | 10/2011 | Warnick | |
| 8,062,375 B2 | 11/2011 | Glerum | |
| 8,105,382 B2 | 1/2012 | Olmos | |
| 8,123,810 B2 | 2/2012 | Gordon | |
| 8,137,405 B2 | 3/2012 | Kostuik | |
| 8,157,845 B2 | 4/2012 | Warnick | |
| 8,262,666 B2 | 9/2012 | Baynham | |
| 8,273,129 B2 | 9/2012 | Baynham | |
| 8,292,959 B2 | 10/2012 | Webb | |
| 8,382,842 B2 | 2/2013 | Greenhalgh | |
| 8,409,290 B2 | 4/2013 | Zamani | |
| 8,444,650 B2 | 5/2013 | Warnick | |
| 8,529,628 B2* | 9/2013 | Marino et al. | 623/17.16 |
| 8,647,386 B2 | 2/2014 | Gordon | |
| 8,940,048 B2* | 1/2015 | Butler et al. | 623/17.15 |
| 2002/0045945 A1 | 4/2002 | Liu | |
| 2002/0068976 A1 | 6/2002 | Jackson | |
| 2002/0068977 A1 | 6/2002 | Jackson | |
| 2003/0065396 A1* | 4/2003 | Michelson | 623/17.15 |
| 2004/0030387 A1 | 2/2004 | Landry | |
| 2004/0049271 A1 | 3/2004 | Biedermann | |
| 2004/0054412 A1 | 3/2004 | Gerbec et al. | |
| 2004/0153065 A1 | 8/2004 | Lim | |
| 2005/0021041 A1 | 1/2005 | Michelson | |
| 2005/0021145 A1 | 1/2005 | de Villiers | |
| 2005/0033432 A1 | 2/2005 | Gordon | |
| 2005/0080422 A1 | 4/2005 | Otte | |
| 2005/0113916 A1 | 5/2005 | Branch, Jr. | |
| 2005/0113917 A1* | 5/2005 | Chae et al. | 623/17.11 |
| 2005/0149188 A1 | 7/2005 | Cook | |
| 2005/0171541 A1 | 8/2005 | Boehm | |
| 2005/0251258 A1 | 11/2005 | Jackson | |
| 2005/0261769 A1* | 11/2005 | Moskowitz et al. | 623/17.11 |
| 2005/0273171 A1 | 12/2005 | Gordon | |
| 2005/0273174 A1 | 12/2005 | Gordon | |
| 2005/0278026 A1 | 12/2005 | Gordon | |
| 2005/0283244 A1 | 12/2005 | Gordon | |
| 2005/0283245 A1 | 12/2005 | Gordon | |
| 2006/0004453 A1 | 1/2006 | Bartish, Jr. et al. | |
| 2006/0015184 A1 | 1/2006 | Winterbottom | |
| 2006/0058878 A1 | 3/2006 | Michelson | |
| 2006/0084986 A1 | 4/2006 | Grinberg | |
| 2006/0122701 A1 | 6/2006 | Kiester | |
| 2006/0129244 A1 | 6/2006 | Ensign | |
| 2006/0142859 A1 | 6/2006 | Mcluen | |
| 2006/0149385 A1 | 7/2006 | McKay | |
| 2006/0195192 A1 | 8/2006 | Gordon et al. | |
| 2006/0229729 A1 | 10/2006 | Gordon | |
| 2006/0241770 A1 | 10/2006 | Rhoda | |
| 2006/0253201 A1 | 11/2006 | Mcluen | |
| 2007/0043442 A1 | 2/2007 | Abernathie | |
| 2007/0050030 A1 | 3/2007 | Kim | |
| 2007/0050032 A1 | 3/2007 | Gittings et al. | |
| 2007/0055377 A1 | 3/2007 | Hanson et al. | |
| 2007/0123989 A1 | 5/2007 | Gfeller | |
| 2007/0191951 A1 | 8/2007 | Branch | |
| 2007/0255415 A1 | 11/2007 | Edie et al. | |
| 2007/0270963 A1 | 11/2007 | Melkent et al. | |
| 2007/0270968 A1 | 11/2007 | Baynham | |
| 2008/0021559 A1 | 1/2008 | Thramann | |
| 2008/0065222 A1 | 3/2008 | Hamada | |
| 2008/0114467 A1 | 5/2008 | Capote | |
| 2008/0140207 A1 | 6/2008 | Olmos | |
| 2008/0147194 A1 | 6/2008 | Grotz | |
| 2008/0167657 A1 | 7/2008 | Greenhalgh | |

(56) References Cited

U.S. PATENT DOCUMENTS

| | | | |
|---|---|---|---|
| 2008/0183204 A1* | 7/2008 | Greenhalgh et al. | 606/198 |
| 2008/0221694 A1 | 9/2008 | Warnick | |
| 2008/0275455 A1 | 11/2008 | Berry et al. | |
| 2008/0281346 A1 | 11/2008 | Greenhalgh et al. | |
| 2008/0288073 A1 | 11/2008 | Renganath et al. | |
| 2008/0300598 A1 | 12/2008 | Barreiro et al. | |
| 2008/0306488 A1 | 12/2008 | Altarac | |
| 2008/0319487 A1 | 12/2008 | Fielding et al. | |
| 2008/0319549 A1 | 12/2008 | Greenhalgh et al. | |
| 2009/0024217 A1 | 1/2009 | Levy | |
| 2009/0076616 A1 | 3/2009 | Duggal | |
| 2009/0125062 A1 | 5/2009 | Arnin | |
| 2009/0149956 A1 | 6/2009 | Greenhalgh et al. | |
| 2009/0149959 A1 | 6/2009 | Conner et al. | |
| 2009/0204218 A1 | 8/2009 | Richelsoph | |
| 2009/0222100 A1 | 9/2009 | Cipoletti et al. | |
| 2009/0240334 A1 | 9/2009 | Richelsoph | |
| 2009/0270989 A1 | 10/2009 | Conner et al. | |
| 2009/0276049 A1 | 11/2009 | Weiland | |
| 2009/0281628 A1 | 11/2009 | Oglaza | |
| 2009/0292361 A1 | 11/2009 | Lopez | |
| 2009/0299478 A1 | 12/2009 | Carls et al. | |
| 2009/0312763 A1 | 12/2009 | Mccormack | |
| 2010/0049324 A1 | 2/2010 | Valdevit | |
| 2010/0070041 A1 | 3/2010 | Peterman | |
| 2010/0082109 A1 | 4/2010 | Greenhalgh et al. | |
| 2010/0179657 A1 | 7/2010 | Greenhalgh et al. | |
| 2010/0185291 A1 | 7/2010 | Jimenez | |
| 2010/0191336 A1 | 7/2010 | Greenhalgh | |
| 2010/0204795 A1 | 8/2010 | Greenhalgh | |
| 2010/0211176 A1 | 8/2010 | Greenhalgh | |
| 2010/0222816 A1 | 9/2010 | Gabelberger | |
| 2010/0222884 A1 | 9/2010 | Greenhalgh | |
| 2010/0234952 A1 | 9/2010 | Peterman | |
| 2010/0249933 A1 | 9/2010 | Trieu | |
| 2010/0280622 A1 | 11/2010 | Mckinley | |
| 2010/0286779 A1 | 11/2010 | Thibodeau | |
| 2010/0286780 A1 | 11/2010 | Dryer | |
| 2010/0286783 A1* | 11/2010 | Lechmann et al. | 623/17.12 |
| 2010/0292796 A1 | 11/2010 | Greenhalgh | |
| 2010/0305705 A1 | 12/2010 | Butler | |
| 2010/0331981 A1 | 12/2010 | Mohammed | |
| 2010/0331985 A1 | 12/2010 | Gordon | |
| 2011/0035011 A1 | 2/2011 | Cain | |
| 2011/0093074 A1 | 4/2011 | Glerum | |
| 2011/0106259 A1 | 5/2011 | Lindenmann | |
| 2011/0144755 A1 | 6/2011 | Baynham | |
| 2011/0160861 A1 | 6/2011 | Jimenez | |
| 2011/0172774 A1 | 7/2011 | Varela | |
| 2011/0276142 A1 | 11/2011 | Niemiec | |
| 2011/0301713 A1 | 12/2011 | Theofilos | |
| 2011/0319997 A1 | 12/2011 | Glerum | |
| 2012/0035729 A1 | 2/2012 | Glerum | |
| 2012/0059470 A1 | 3/2012 | Weiman | |
| 2012/0059472 A1 | 3/2012 | Weiman | |
| 2012/0109308 A1 | 5/2012 | Lechmann | |
| 2012/0130496 A1 | 5/2012 | Duffield | |
| 2012/0165945 A1 | 6/2012 | Hansell | |
| 2012/0185049 A1 | 7/2012 | Varela | |
| 2012/0191194 A1 | 7/2012 | Olmos | |
| 2012/0209386 A1 | 8/2012 | Triplett | |
| 2012/0215313 A1 | 8/2012 | Saidha | |
| 2012/0226357 A1 | 9/2012 | Varela | |
| 2012/0265309 A1 | 10/2012 | Glerum | |
| 2012/0277870 A1 | 11/2012 | Wolters | |
| 2012/0290090 A1 | 11/2012 | Glerum | |
| 2012/0323329 A1 | 12/2012 | Jimenez | |
| 2012/0330421 A1 | 12/2012 | Weiman | |
| 2012/0330422 A1 | 12/2012 | Weiman | |
| 2012/0330426 A1 | 12/2012 | McLaughlin | |
| 2013/0023993 A1 | 1/2013 | Weiman | |
| 2013/0023994 A1 | 1/2013 | Glerum | |
| 2013/0158669 A1 | 6/2013 | Sungarian | |
| 2014/0031938 A1* | 1/2014 | Lechmann et al. | 623/17.16 |
| 2015/0094813 A1* | 4/2015 | Lechmann et al. | 623/17.15 |

FOREIGN PATENT DOCUMENTS

| | | |
|---|---|---|
| EP | 0576379 B1 | 6/1993 |
| EP | 0610837 B1 | 7/1994 |
| FR | 2794968 | 12/2000 |
| JP | 2000-513263 | 10/2000 |
| SU | 1424826 A1 | 9/1988 |
| WO | 9201428 A1 | 2/1992 |
| WO | 9525485 A1 | 9/1995 |
| WO | 9942062 A1 | 8/1999 |
| WO | 9966867 A1 | 12/1999 |
| WO | 0245625 A1 | 6/2002 |
| WO | 2004019829 A1 | 3/2004 |
| WO | 2004069033 A2 | 8/2004 |
| WO | 2006045094 A2 | 4/2006 |
| WO | 2006047587 A2 | 5/2006 |
| WO | 2006113080 A2 | 10/2006 |
| WO | 2008044057 A1 | 4/2008 |
| WO | 2008134515 A1 | 11/2008 |
| WO | 2009114381 A1 | 9/2009 |
| WO | 2012031267 A1 | 3/2012 |

* cited by examiner

EXPANDABLE FUSION DEVICE AND METHOD OF INSTALLATION THEREOF

CROSS-REFERENCE TO RELATED APPLICATION

This application is a continuation-in-part of U.S. Pat. No. 8,845,731, entitled "Expandable Fusion Device and Method of Installation Thereof," filed on Sep. 3, 2010, the entire disclosure of which is incorporated by reference herein.

FIELD OF THE INVENTION

The present invention relates to the apparatus and method for promoting an intervertebral fusion, and more particularly relates to an expandable fusion device capable of being inserted between adjacent vertebrae to facilitate the fusion process.

BACKGROUND

A common procedure for handling pain associated with intervertebral discs that have become degenerated due to various factors such as trauma or aging is the use of intervertebral fusion devices for fusing one or more adjacent vertebral bodies. Generally, to fuse the adjacent vertebral bodies, the intervertebral disc is first partially or fully removed. An intervertebral fusion device is then typically inserted between neighboring vertebrae to maintain normal disc spacing and restore spinal stability, thereby facilitating an intervertebral fusion.

There are a number of known conventional fusion devices and methodologies in the art for accomplishing the intervertebral fusion. These include screw and rod arrangements, solid bone implants, and fusion devices which include a cage or other implant mechanism which, typically, is packed with bone and/or bone growth inducing substances. These devices are implanted between adjacent vertebral bodies in order to fuse the vertebral bodies together, alleviating the associated pain.

However, there are drawbacks associated with the known conventional fusion devices and methodologies. For example, present methods for installing a conventional fusion device often require that the adjacent vertebral bodies be distracted to restore a diseased disc space to its normal or healthy height prior to implantation of the fusion device. In order to maintain this height once the fusion device is inserted, the fusion device is usually dimensioned larger in height than the initial distraction height. This difference in height can make it difficult for a surgeon to install the fusion device in the distracted intervertebral space.

As such, there exists a need for a fusion device capable of being installed inside an intervertebral disc space at a minimum to no distraction height and for a fusion device that can maintain a normal distance between adjacent vertebral bodies when implanted.

SUMMARY

In an exemplary embodiment, the present invention provides an intervertebral implant. The intervertebral implant may comprise an upper endplate comprising a first upper endplate portion and a second upper endplate portion. The intervertebral implant may comprise a lower endplate comprising a first lower endplate portion and a second lower endplate portion. The intervertebral implant may comprise a front sloped actuator configured to movingly engage a front end of the upper endplate and a front end of the lower endplate. The intervertebral implant may comprise a rear sloped actuator configured to movingly engage a rear end of the upper endplate and a rear end of the lower endplate. The intervertebral implant may be configured to transition from a collapsed configuration having a first height and a first width to an expanded configuration having a second height and a second width.

In an exemplary embodiment, the present invention provides an intervertebral implant. The intervertebral implant may comprise an upper endplate. The upper endplate may comprise a first upper endplate portion comprising a front ramped surface and a rear ramped surface. The upper endplate may further comprise a second upper endplate portion comprising a front ramped surface and a rear ramped surface. The upper endplate may further comprise endplate pins connecting the first upper endplate portion and the second upper endplate portion. The intervertebral implant may further comprise a lower endplate. The lower endplate may comprise a first lower endplate portion comprising a front ramped surface and a rear ramped surface. The lower endplate may further comprise a second lower endplate portion comprising a front ramped surface and a rear ramped surface. The lower endplate may further comprise endplate pins connecting the first lower endplate portion and the second lower endplate portion. The intervertebral implant may further comprise a front sloped actuator configured to movingly engage the front ramped surface of the first upper endplate portion, the front ramped surface of the second upper endplate portion, the front ramped surface of the first lower endplate portion, and the front ramped surface of the second lower endplate portion. The intervertebral implant may further comprise a rear sloped actuator configured to movingly engage the rear ramped surface of the first upper endplate portion, the front ramped surface of the second upper endplate portion, the rear ramped surface of the first lower endplate portion, and the rear ramped surface of the second lower endplate portion. The intervertebral implant may be configured to transition from a collapsed configuration having a first height and a first width to an expanded configuration having a second height and a second width.

In another embodiment, the present invention provides a method of installing an intervertebral implant, the method comprising: introducing the intervertebral implant into an intervertebral space; and contracting an actuator assembly to cause the intervertebral implant to transition from a collapsed configuration having a first height and a first width to an expanded configuration having a second height and a second width.

In another embodiment, the present invention provides an intervertebral implant. The intervertebral implant may comprise an upper endplate comprising a first upper endplate portion and a second upper endplate portion. The intervertebral implant may further comprise a lower endplate comprising a first lower endplate portion and a second lower endplate portion. The intervertebral implant may further comprise an actuator assembly disposed between the upper endplate and the lower endplate, the actuator assembly being configured to movingly engage front ends of the upper endplate and the lower endplate and also movingly engage rear ends of the upper endplate and the lower endplate. The intervertebral implant may be configured to first transition from a collapsed configuration having a first width and a first height to a laterally expanded configuration having a second width and then transition to a vertically expanded configuration having a second height.

In another embodiment, the present invention provides an intervertebral implant. The intervertebral implant may comprise an upper endplate comprising. The upper endplate may comprise a first upper endplate portion comprising a front ramped surface and a rear ramped surface. The upper endplate may further comprise a second upper endplate portion comprising a front ramped surface and a rear ramped surface. The upper endplate may further comprise endplate pins connecting the first upper endplate portion and the second upper endplate portion. The intervertebral implant may further comprise a lower endplate. The lower endplate may comprise a first lower endplate portion comprising a front ramped surface and a rear ramped surface. The lower endplate may further comprise a second lower endplate portion comprising a front ramped surface and a rear ramped surface. The lower endplate may further comprise endplate pins connecting the first lower endplate portion and the second lower endplate portion. The intervertebral implant may further comprise a front sloped actuator assembly disposed between the upper endplate and the lower endplate. The front sloped actuator assembly may comprise a pair of front height actuators, wherein the front height actuators each comprise opposing ramped surfaces in respective engagement with the upper endplate and the lower endplate. The front sloped actuator assembly may further comprise a front width actuator that is wedge shaped and disposed between the pair of front height actuators and in moving engagement with the pair of front height actuators, wherein the front width actuator is operable to force the pair of front height actuators laterally apart. The intervertebral implant may further comprise a rear sloped actuator assembly. The rear sloped actuator assembly may comprise a pair of rear height actuators, wherein the rear height actuators each comprise opposing ramped surfaces in respective engagement with the upper endplate and the lower endplate. The rear sloped actuator assembly may further comprise a front width actuator disposed between the pair of rear height actuators and in moving engagement with the pair of rear height actuators, wherein the front width actuator is operable to force the pair of front height actuators laterally apart. The intervertebral implant may be configured to first transition from a collapsed configuration having a first width and a first height to a laterally expanded configuration having a second width and then transition to a vertically expanded configuration having a second height.

In another embodiment, the present invention provides a method of installing an intervertebral implant, the method comprising. The method may comprise introducing the intervertebral implant into an intervertebral space. The method may further comprise moving at least one of a front width actuator or a rear width actuator to cause the front width actuator and the rear width actuator to move closer to one another such that the intervertebral implant transitions from a laterally collapsed configuration having a first width to a laterally expanded configuration having a second width. The method may further comprise moving at least one of a front sloped actuator assembly or a rear sloped actuator assembly to cause the front sloped actuator assembly and the rear sloped actuator assembly to move closer to another such that the intervertebral implant transitions from a vertically collapsed configuration having a first height to a vertically expanded configuration having a second height.

Further areas of applicability of the present invention will become apparent from the detailed description provided hereinafter. It should be understood that the detailed description and specific examples, while indicating the preferred or exemplary embodiments of the invention, are intended for purposes of illustration only and are not intended to limit the scope of the invention.

BRIEF DESCRIPTION OF THE DRAWINGS

The present invention will become more fully understood from the detailed description and the accompanying drawings, wherein.

DETAILED DESCRIPTION

Figure 1:
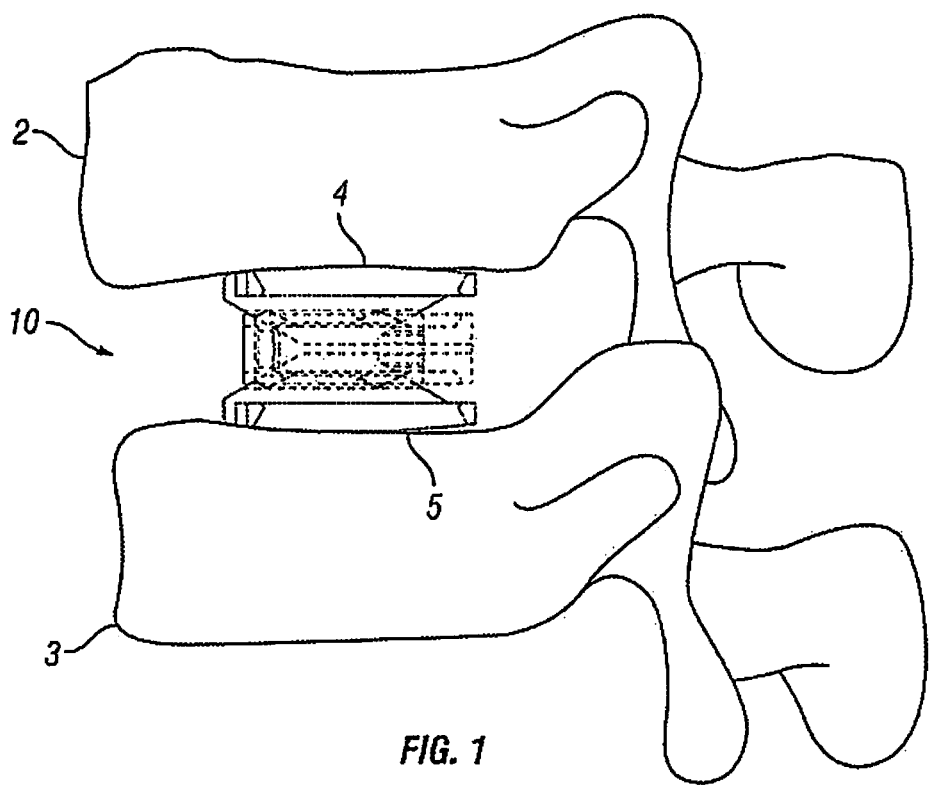
FIG. 1 is a side view of an embodiment of an expandable fusion device shown between adjacent vertebrae according to the present invention.
Figure 2:
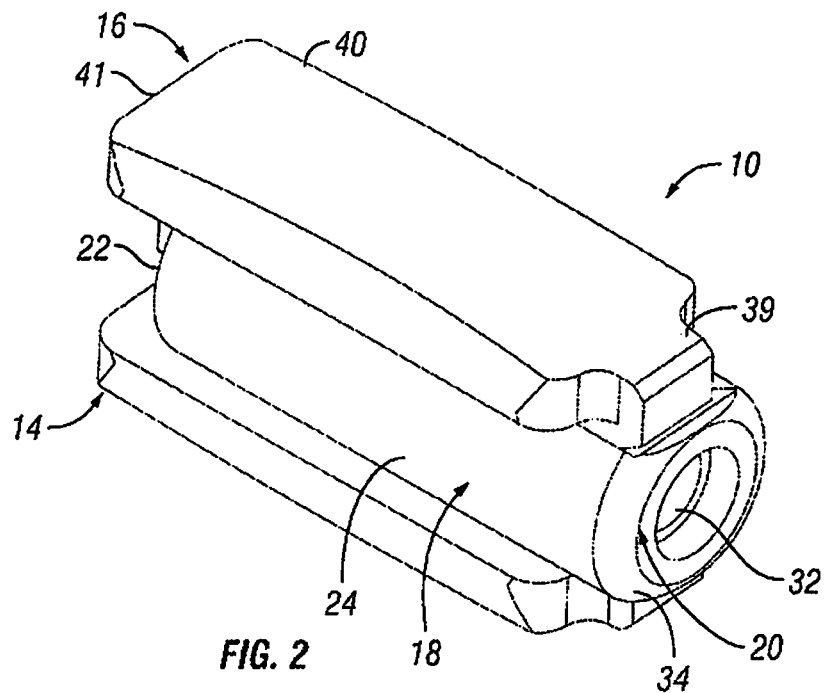
FIG. 2 is a front perspective view of the expandable fusion device of FIG. 1 shown in an unexpanded position in accordance with one embodiment of the present invention.
Figure 3:
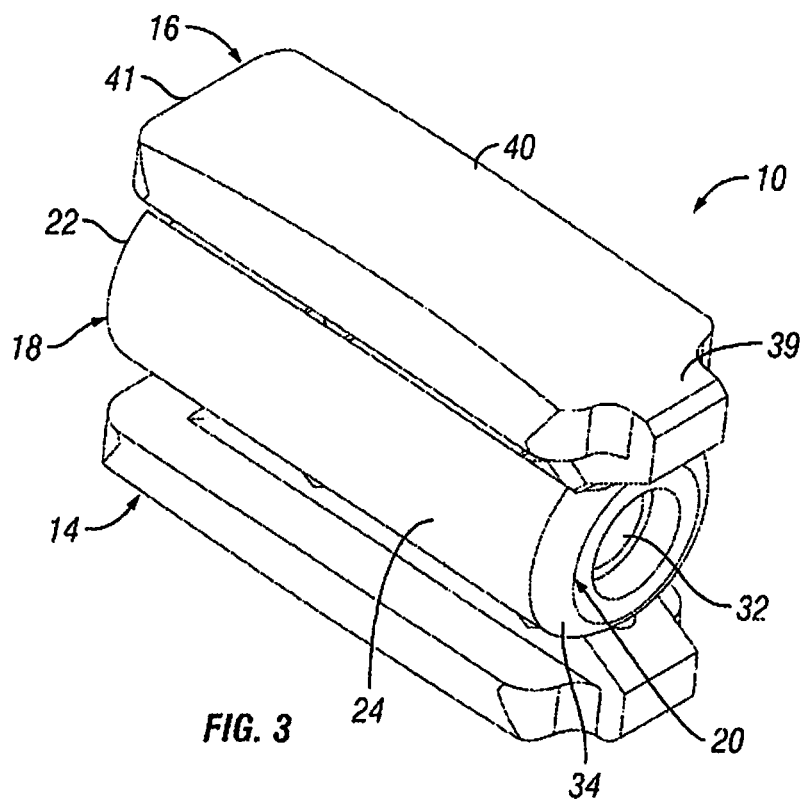
FIG. 3 is a front perspective view of the expandable fusion device of FIG. 1 shown in an expanded position in accordance with one embodiment of the present invention.
Figure 4:
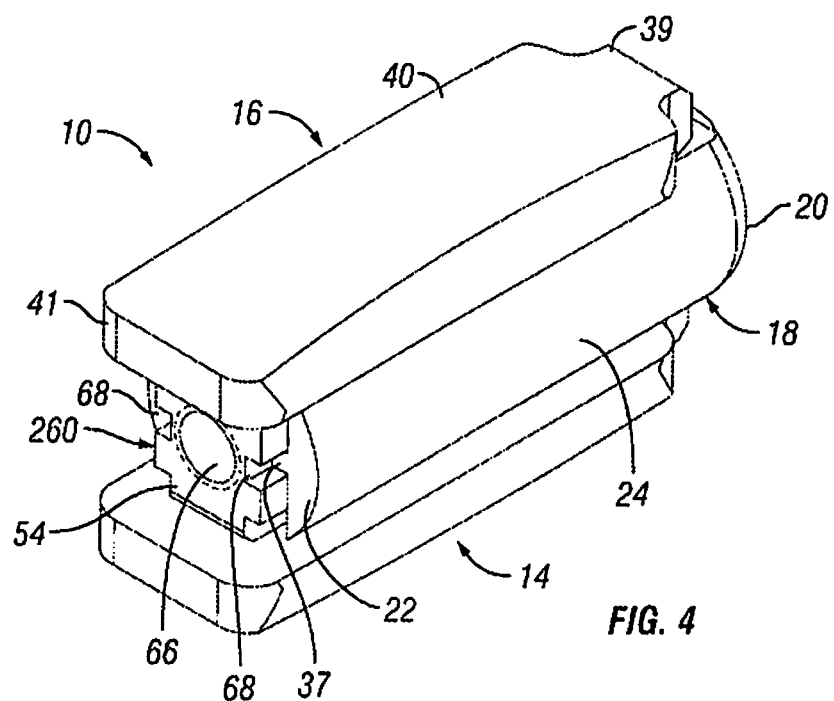
FIG. 4 is a rear perspective view of the expandable fusion device of FIG. 1 shown in an unexpanded position in accordance with one embodiment of the present invention.
Figure 5:
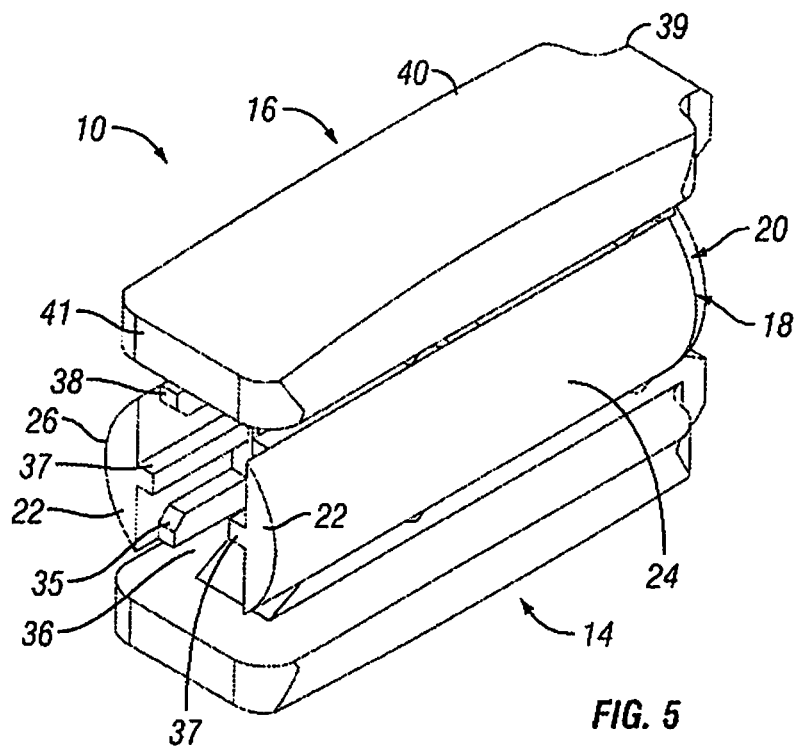
FIG. 5 is a rear perspective view of the expandable fusion device of FIG. 1 shown in an expanded position in accordance with one embodiment of the present invention.
Figure 6:
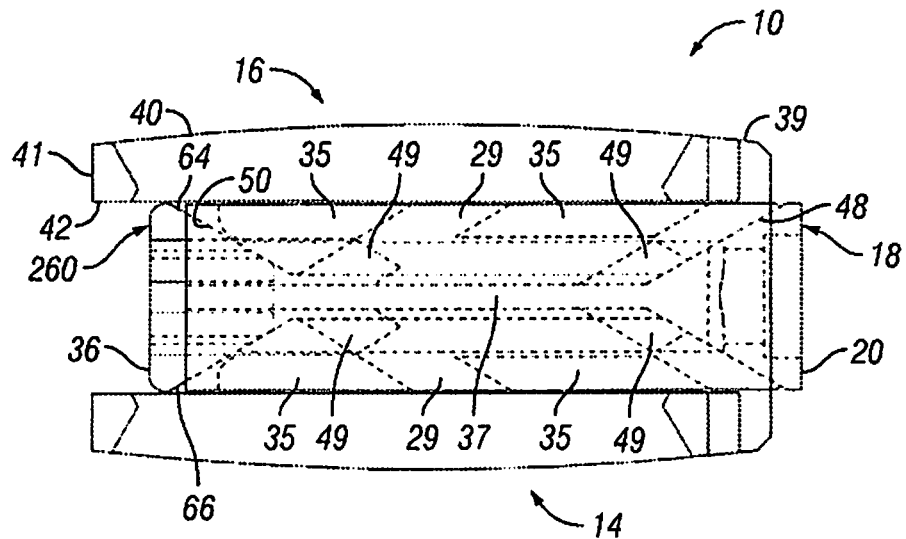
FIG. 6 is a side view of the expandable fusion device of FIG. 1 shown in an unexpanded position in accordance with one embodiment of the present invention.

The following description of the preferred embodiment(s) is merely exemplary in nature and is in no way intended to limit the invention, its application, or uses.

A spinal fusion is typically employed to eliminate pain caused by the motion of degenerated disk material. Upon successful fusion, a fusion device becomes permanently fixed within the intervertebral disc space. Looking at FIG. 1, an exemplary embodiment of an expandable fusion device 10 is shown between adjacent vertebral bodies 2 and 3. The fusion device 10 engages the endplates 4 and 5 of the adjacent vertebral bodies 2 and 3 and, in the installed position, maintains normal intervertebral disc spacing and restores spinal stability, thereby facilitating an intervertebral fusion. The expandable fusion device 10 can be manufactured from a number of materials including titanium, stainless steel, titanium alloys, non-titanium metallic alloys, polymeric materials, plastics, plastic composites, PEEK, ceramic, and elastic materials. In an embodiment, the expandable fusion device 10 can be configured to be placed down an endoscopic tube and into the disc space between the adjacent vertebral bodies 2 and 3.

In an exemplary embodiment, bone graft or similar bone growth inducing material can be introduced around and within the fusion device 10 to further promote and facilitate the intervertebral fusion. The fusion device 10, in one embodiment, is preferably packed with bone graft or similar bone growth inducing material to promote the growth of bone through and around the fusion device. Such bone graft may be packed between the endplates of the adjacent vertebral bodies prior to, subsequent to, or during implantation of the fusion device.

With reference to FIGS. 2-7, an embodiment of the fusion device 10 is shown. In an exemplary embodiment, the fusion device 10 includes a first endplate 14, a second endplate 16, a central ramp 18, and a driving ramp 260. In an embodiment, the expandable fusion device 10 can be configured to be placed down an endoscopic tube and into the disc space between the adjacent vertebral bodies 2 and 3. One or more components of the fusion device 10 may contain features, such as through bores, that facilitate placement down an endoscopic tube. In an embodiment, components of the fusion device 10 are placed down the endoscopic tube with assembly of the fusion device 10 in the disc space.

Although the following discussion relates to the second endplate 16, it should be understood that it also equally applies to the first endplate 14 as the second endplate 16 is substantially identical to the first endplate 14 in embodiments of the present invention. Turning now to FIGS. 2-7 and 10, in an exemplary embodiment, the second endplate 16 has a first end 39 and a second end 41. In the illustrated embodiment, the second endplate 16 further comprise an upper surface 40 connecting the first end 39 and the second end 41, and a lower surface 42 connecting the first end 39 and the second end 41. In an embodiment, the second endplate 16 further comprises a through opening 44, as seen on FIG. 11. The through opening 44, in an exemplary embodiment, is sized to receive bone graft or similar bone growth inducing material and further allow the bone graft or similar bone growth inducing material to be packed in the central opening in the central ramp 18.

Figure 7:
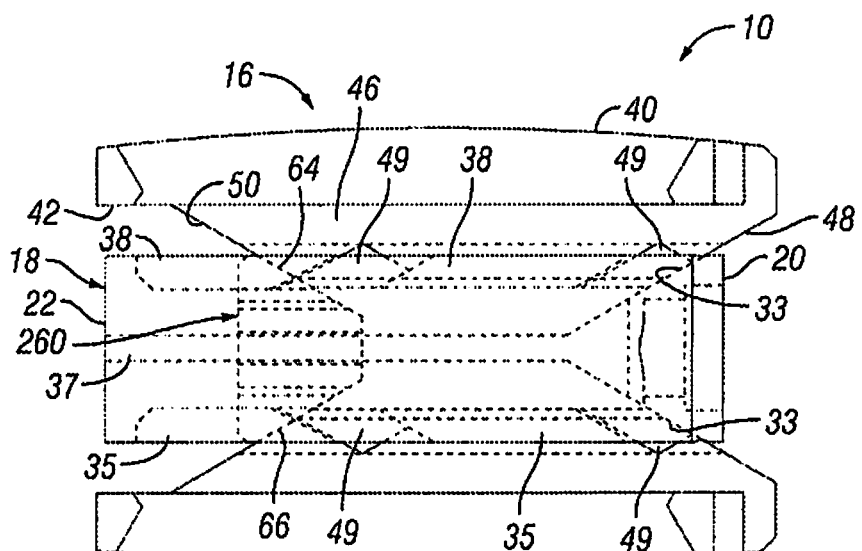
FIG. 7 is a side view of the expandable fusion device of FIG. 1 shown in an expanded position in accordance with one embodiment of the present invention.
Figure 10:
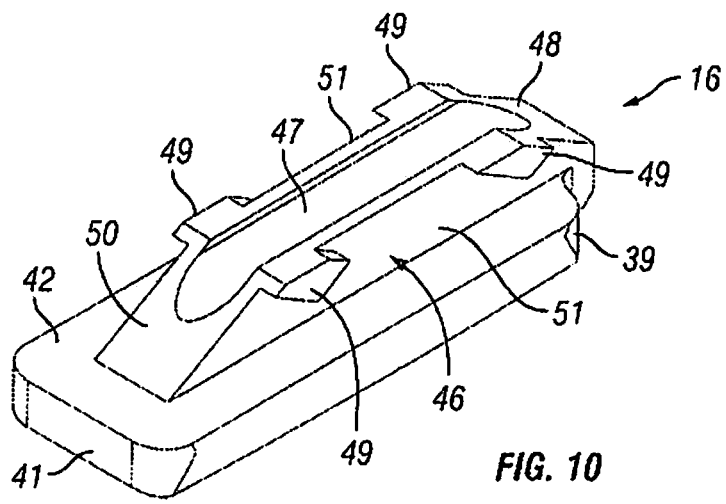
FIG. 10 is a perspective of an endplate of the expandable fusion device of FIG. 1 in accordance with one embodiment of the present invention.

As best seen in FIGS. 7 and 10, the lower surface 42 includes at least one extension 46 extending along at least a portion of the lower surface 42, in an embodiment. In an exemplary embodiment, the extension 46 can extend along a substantial portion of the lower surface 42, including, along the center of the lower surface 42. In the illustrated embodiment, the extension 46 includes a generally concave surface 47. The concave surface 47 can form a through bore with the corresponding concave surface 47 (not illustrated) of the first endplate 14, for example, when the device 10 is in an unexpanded configuration. In another exemplary embodiment, the extension 46 includes at least one ramped surface 48. In another exemplary embodiment, there are two ramped surfaces 48, 50 with the first ramped surface 48 facing the first end 39 and the second ramped surface facing the second end 41. In an embodiment, the first ramped surface 48 can be proximate the first end 39, and the second ramped surface 50 can be proximate the second end 41. It is contemplated that the slope of the ramped surfaces 48, 50 can be equal or can differ from each other. The effect of varying the slopes of the ramped surfaces 48, 50 is discussed below.

In one embodiment, the extension 46 can include features for securing the endplate 16 when the expandable fusion device 10 is in an expanded position. In an embodiment, the extension 46 includes one or more protuberances 49 extending from the lateral sides 51 of the extension. In the illustrated embodiment, there are two protuberances 49 extending from each of the lateral sides 51 with each of the sides 53 having one of the protuberances 49 extending from a lower portion of either end. As will be discussed in more detail below, the protuberances 49 can be figured to engage the central ramp 18 preventing and/or restricting longitudinal movement of the endplate 16 when the device 10 is in an expanded position.

Figure 15:
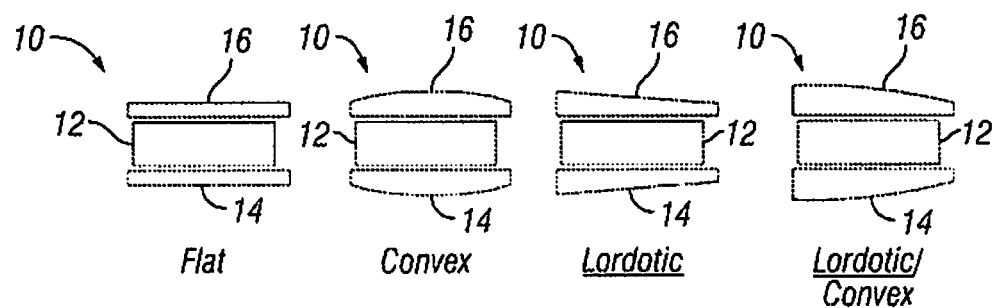
FIG. 15 is a side schematic view of the expandable fusion device of FIG. 1 having different endplates.

As illustrated in FIGS. 2-5, in one embodiment, the upper surface 40 of the second endplate 16 is flat and generally planar to allow the upper surface 40 of the endplate 16 to engage with the adjacent vertebral body 2. Alternatively, as shown in FIG. 15, the upper surface 40 can be curved convexly or concavely to allow for a greater or lesser degree of engagement with the adjacent vertebral body 2. It is also contemplated that the upper surface 40 can be generally planar but includes a generally straight ramped surface or a curved ramped surface. The ramped surface allows for engagement with the adjacent vertebral body 2 in a lordotic fashion. While not illustrated, in an exemplary embodiment, the upper surface 40 includes texturing to aid in gripping the adjacent vertebral bodies. Although not limited to the following, the texturing can include teeth, ridges, friction increasing elements, keels, or gripping or purchasing projections.

Referring now to FIGS. 2-8, in an exemplary embodiment, the central ramp 18 has a first end 20, a second end 22, a first side portion 24 connecting the first end 20 and the second end 22, and a second side portion 26 (best seen on FIG. 5) on the opposing side of the central ramp 12 connecting the first end 20 and the second end 22. The first side portion 24 and the second side portion 26 may be curved, in an exemplary embodiment. The central ramp 18 further includes a lower end 28, which is sized to receive at least a portion of the first endplate 14, and an upper end 30, which is sized to receive at least a portion of the second endplate 16.

The first end 20 of the central ramp 18, in an exemplary embodiment, includes an opening 32. The opening 32 can be configured to receive an endoscopic tube in accordance with one or more embodiments. The first end 20 of the central ramp 18, in an exemplary embodiment, includes at least one angled surface 33, but can include multiple angled surfaces. The angled surface 33 can serve to distract the adjacent vertebral bodies when the fusion device 10 is inserted into an intervertebral space.

The second end 22 of the central ramp 18, in an exemplary embodiment, includes an opening 36. The opening 36 extends from the second end 22 of the central ramp 18 into a central guide 37 in the central ramp 18.

Figure 8:
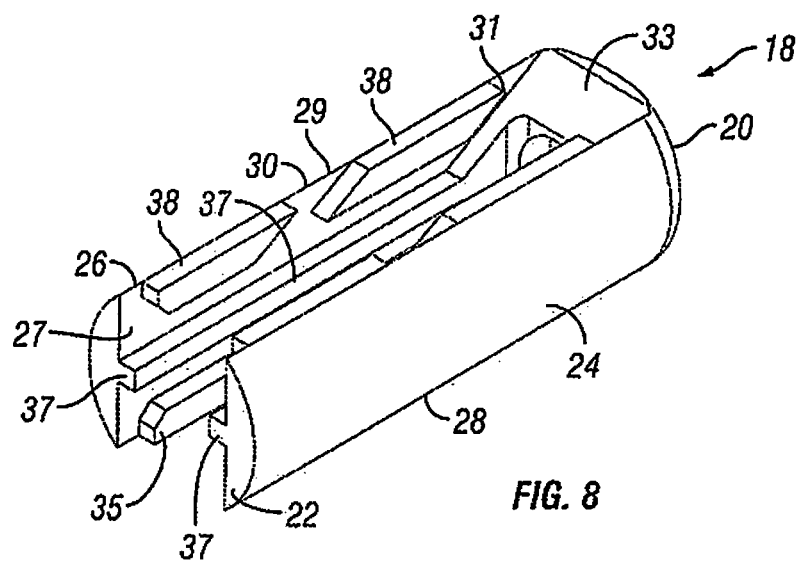
FIG. 8 is a perspective view of the central ramp of the expandable fusion device of FIG. 1 in accordance with one embodiment of the present invention.
Figure 9:
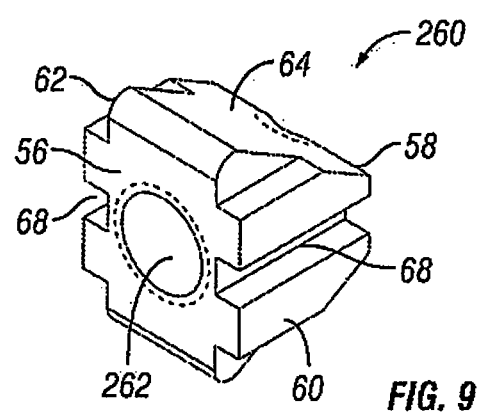
FIG. 9 is a perspective view of the driving ramp of the expandable fusion device of FIG. 1 in accordance with one embodiment of the present invention.

In an embodiment, the central ramp 18 further includes one or more ramped surfaces 33. As best seen in FIG. 8, the one or more ramped surfaces 33 positioned between the first side portion 24 and the second side portion 26 and between the central guide 37 and the second end 22. In an embodiment, the one or more ramped surfaces 33 face the second end 22 of the central ramp 18. In one embodiment, the central ramp 18 includes two ramped surfaces 33 with one of the ramped surfaces 33 being sloped upwardly and the other of the ramped surfaces 33 being sloped downwardly. The ramped surfaces 33 of the central ramp can be configured and dimensioned to engage the ramped surface 48 in each of the first and second endplates 14, 16.

Although the following discussion relates to the second side portion 26 of the central ramp 18, it should be understood that it also equally applies to the first side portion 24 in embodiments of the present invention. In the illustrated embodiment, the second side portion 26 includes an inner surface 27. In an embodiment, the second side portion 26 further includes a lower guide 35, a central guide 37, and an upper guide 38. In the illustrated embodiment, the lower guide 35, central guide 37, and the upper guide 38 extend out from the inner surface 27 from the second end 22 to the one or more ramped surfaces 31. In the illustrated embodiment, the second end 22 of the central ramp 18 further includes one or more guides 38. The guides 38 can serve to guide the translational movement of the first and second endplates 14, 16 with respect to the central ramp 18. For example, protuberances 49 on the second endplate 16 may be sized to be received between the central guide 37 and the upper guide 38. Protuberances 49 of the first endplate 16 may be sized to be received between the central guide 37 and the lower guide 35. A first slot 29 may be formed proximate the middle of the upper guide 38. A second slot 31 may be formed between end of the upper guide 38 and the one or more ramped surfaces 33. The protuberances 49 may be sized to be received within the first slot 29 and/or the second slot 31 when the device 10 is in the expanded position.

Referring now to FIGS. 4-7 and 9, the driving ramp 260 has a through bore 262. In an embodiment, the driving ramp 260 is generally wedge-shaped. As illustrated, the driving ramp 260 may comprise a wide end 56, a narrow end 58, a first side portion 60 connecting the wide end 56 and the narrow end 58, and a second side portion 62 connecting the wide end 56 and the narrow end 58. The driving ramp 260 further may comprise ramped surfaces, including an upper ramped surface 64 and an opposing lower ramped surface 66. The upper ramped surface 64 and the lower ramped surface 66 may be configured and dimensioned to engage the ramped surface 50 proximate the second end 41 in of the first and the second endplates 14, 16. The first and second side portions 60, 62 may each include grooves 68 that extend, for example, in a direction parallel to the longitudinal axis of the through bore 262. The grooves 68 may be sized to receive the central guide 37 on the interior surface 27 of each of the side portions 24, 26 of the central ramp 18. In this manner, the grooves 68 together with the central guide 37 can surface to guide the translational movement of the driving ramp 260 in the central ramp 18.

A method of installing the expandable fusion device 10 of FIG. 1 is now discussed in accordance with one embodiment of the present invention. Prior to insertion of the fusion device 10, the intervertebral space is prepared. In one method of installation, a discectomy is performed where the intervertebral disc, in its entirety, is removed. Alternatively, only a portion of the intervertebral disc can be removed. The endplates of the adjacent vertebral bodies 2, 3 are then scraped to create an exposed end surface for facilitating bone growth across the intervertebral space. One or more endoscopic tubes can then be inserted into the disc space. The expandable fusion device 10 can then be introduced into the intervertebral space down an endoscopic tube and seated in an appropriate position in the intervertebral disc space.

After the fusion device 10 has been inserted into the appropriate position in the intervertebral disc space, the fusion device 10 can then be expanded into the expanded position. To expand the fusion device 10, the driving ramp 260 may moved in a first direction with respect to the central ramp 18. Translational movement of the driving ramp 260 through the central ramp 18 may be guided by the central guide 37 on each of the first and second side portions 24, 26 of the central ramp 18. As the driving ramp 260 moves, the upper ramped surface 64 pushes against the ramped surface 50 proximate the second end 41 of the second endplate 16, and the lower ramped surface 66 pushes against the ramped surface 50 proximate the second end 41 of the first endplate 14. In addition, the ramped surfaces 33 in the central ramp 18 push against the ramped surface 48 proximate the first end 41 of the first and second endplates 14, 16. In this manner, the first and second endplates 14, 16 are pushed outwardly into an expanded configuration. As discussed above, the central ramp 16 includes locking features for securing the endplates 14, 16.

Figure 16:
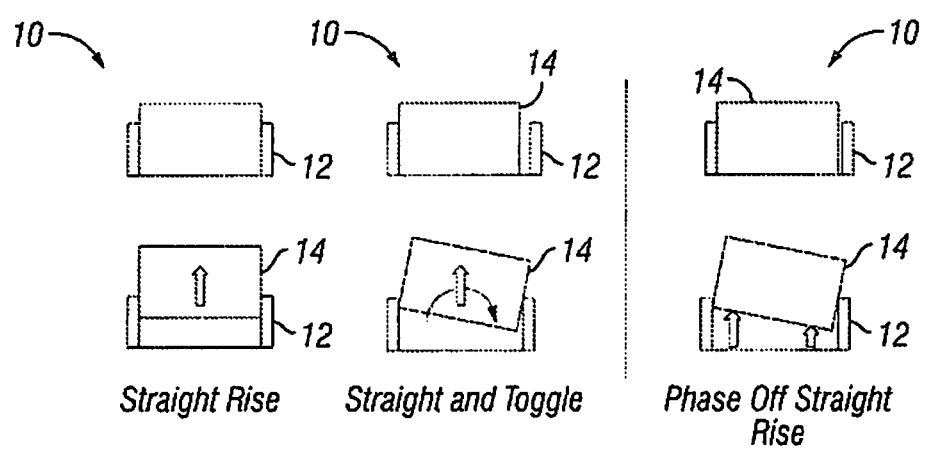
FIG. 16 is a partial side schematic view of the expandable fusion device of FIG. 1 showing different modes of endplate expansion.

It should also be noted that the expansion of the endplates 14, 16 can be varied based on the differences in the dimensions of the ramped surfaces 48, 50 and the angled surfaces 62, 64. As best seen in FIG. 16, the endplates 14, 16 can be expanded in any of the following ways: straight rise expansion, straight rise expansion followed by a toggle into a lordotic expanded configuration, or a phase off straight rise into a lordotic expanded configuration.

Turning back to FIGS. 2-7, in the event the fusion device 10 needs to be repositioned or revised after being installed and expanded, the fusion device 10 can be contracted back to the unexpanded configuration, repositioned, and expanded again once the desired positioning is achieved. To contract the fusion device 10, the central ramp 18 is moved with respect to the central ramp 260 away from the central ramp 260. As the central ramp 18 moves, the ramped surfaces 33 in the central ramp 18 ride along the ramped surfaces 48 of the first and second endplates 14, 16 with the endplates 14, 16 moving inwardly into the unexpanded position.

Figure 17:
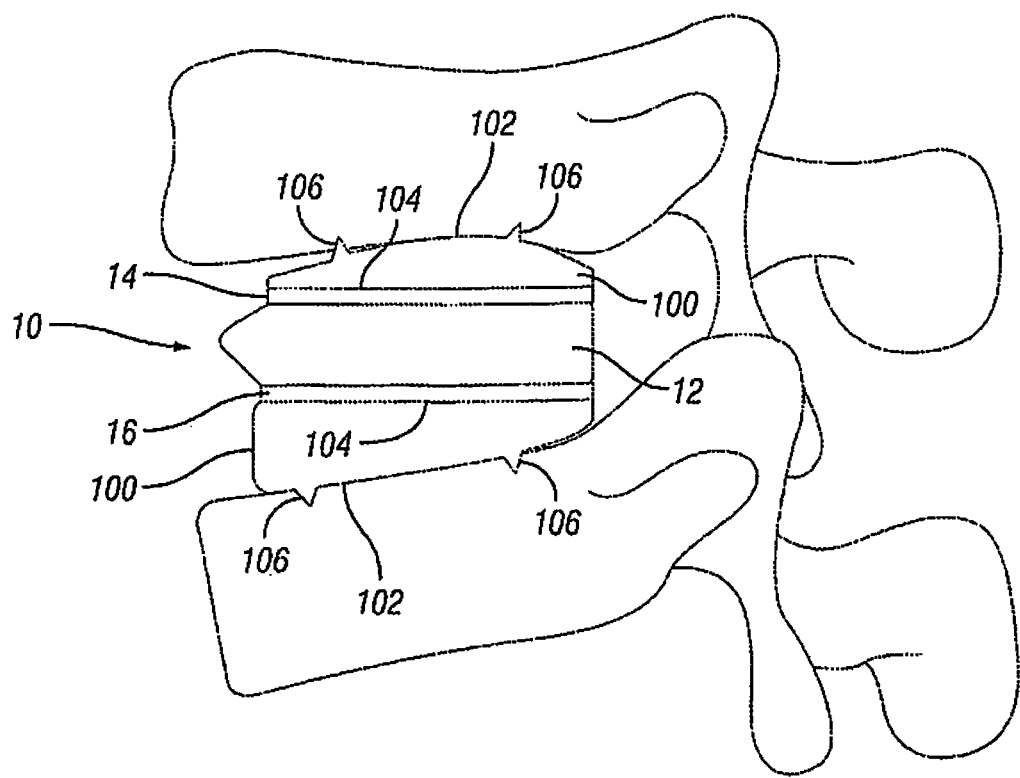
FIG. 17 is a side schematic view of the expandable fusion device of FIG. 1 with artificial endplates shown between adjacent vertebrae.
Figure 18:
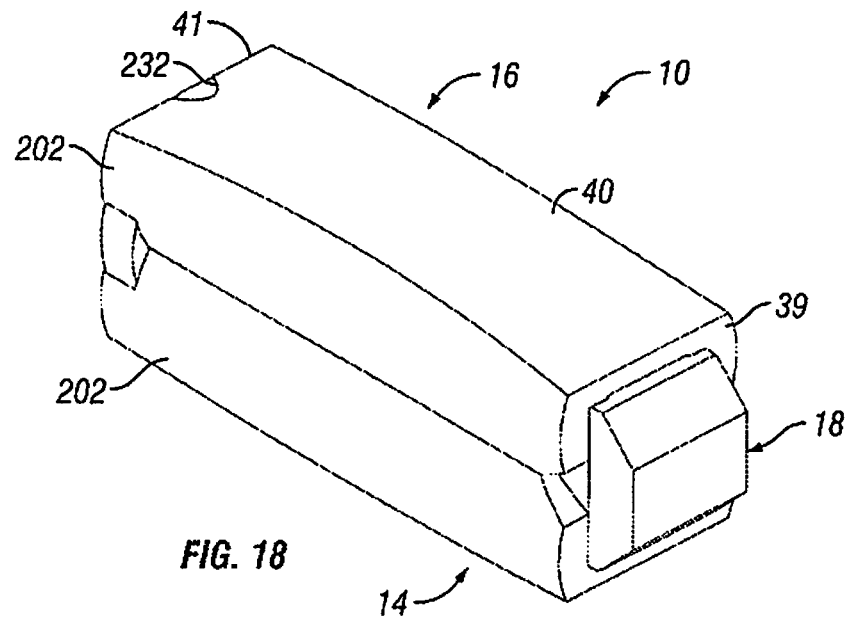
FIG. 18 is a front perspective view of an alternative embodiment of an expandable fusion device shown in an unexpanded position in accordance with one embodiment of the present invention.

With reference now to FIG. 17, fusion device 10 is shown with an exemplary embodiment of artificial endplates 100. Artificial endplates 100 allows the introduction of lordosis even when the endplates 14 and 16 of the fusion device 10 are generally planar. In one embodiment, the artificial endplates 100 have an upper surface 102 and a lower surface 104. The upper surfaces 102 of the artificial endplates 100 have at least one spike 106 to engage the adjacent vertebral bodies. The lower surfaces 104 have complementary texturing or engagement features on their surfaces to engage with the texturing or engagement features on the upper endplate 14 and the lower endplate 16 of the fusion device 10. In an exemplary embodiment, the upper surface 102 of the artificial endplates 100 have a generally convex profile and the lower surfaces 104 have a generally parallel profile to achieve lordosis. In another exemplary embodiment, fusion device 10 can be used with only one artificial endplate 100 to introduce lordosis even when the endplates 14 and 16 of the fusion device 10 are generally planar. The artificial endplate 100 can either engage endplate 14 or engage endplate 16 and function in the same manner as described above with respect to two artificial endplates 100.

Figure 11:
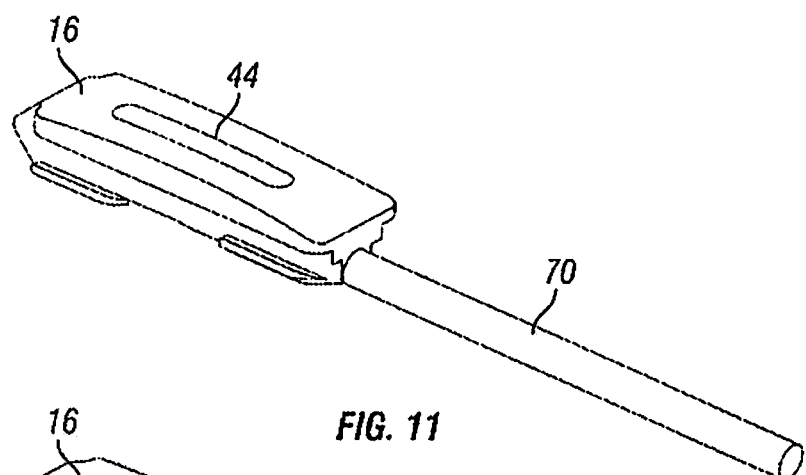
FIG. 11 a perspective view showing placement of the first endplate of an embodiment of an expandable fusion device down an endoscopic tube and into the disc space in accordance with one embodiment of the present invention.
Figure 12:
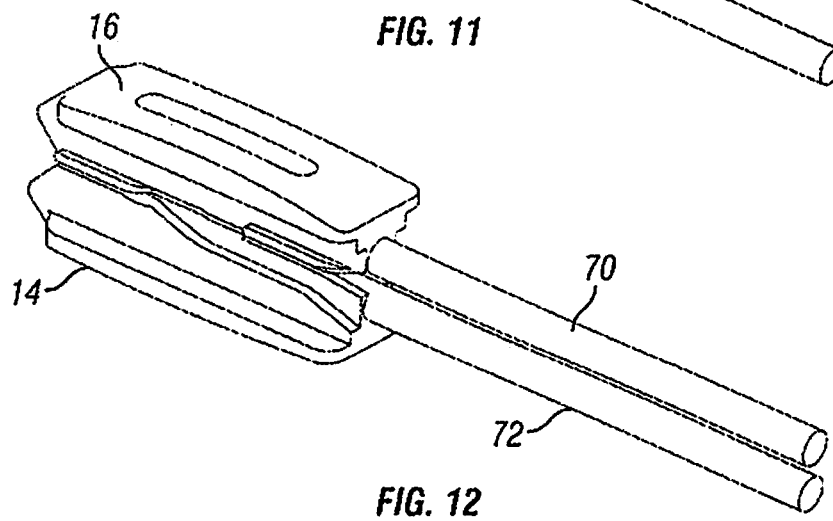
FIG. 12 is a perspective view showing placement of the second endplate of the expandable fusion device down an endoscopic tube and into the disc space in accordance with one embodiment of the present invention.
Figure 13:
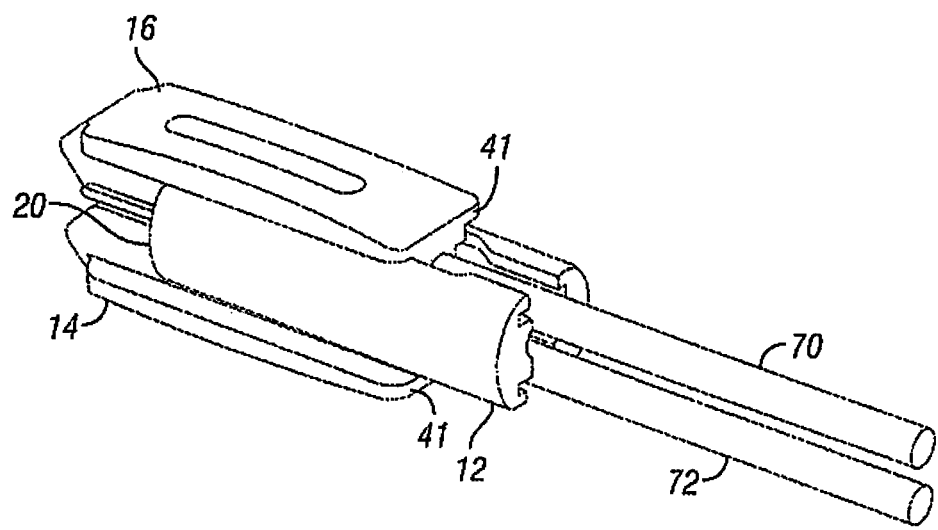
FIG. 13 is a perspective view showing placement of the central ramp of the expandable fusion device down an endoscopic tube and into the disc space in accordance with one embodiment of the present invention.
Figure 14:
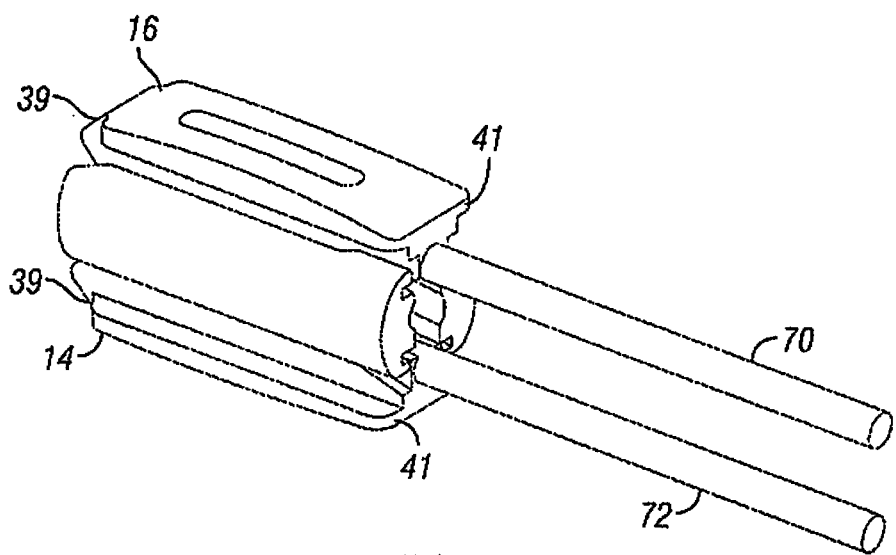
FIG. 14 is a perspective view showing expansion of the expandable fusion device in accordance with one embodiment of the present invention.

With reference to FIGS. 11-14, an embodiment for placing an expandable fusion device 10 into an intervertebral disc space is illustrated. The expandable fusion device 10 can be introduced into the intervertebral space down an endoscopic tube utilizing a tool 70 that is attached to endplate 16, with the second endplate 16 being first placed down the tube with tool 70 and into the disc space, as seen in FIG. 11. After insertion of the second endplate 16, the first endplate 14 can be placed down the same endoscopic tube with tool 72 and into the disc space, as shown on FIG. 12. Following the first endplate 14, the central ramp 12 can be placed down the same endoscopic tube and into the disc space guided by tools 70 and 72, as shown on FIGS. 13 and 14.

Referring now to FIGS. 18-23, an alternative embodiment of the expandable fusion device 10 is shown. In an exemplary embodiment, the fusion device 10 includes a first endplate 14, a second endplate 16, a central ramp 18, and an actuator assembly 200. As will be discussed in more detail below, the actuator assembly 200 drives the central ramp 18 which forces apart the first and second endplates 14, 16 to place the expandable fusion device in an expanded position. One or more components of the fusion device 10 may contain features, such as through bores, that facilitate placement down an endoscopic tube. In an embodiment, components of the fusion device 10 are placed down the endoscopic tube with assembly of the fusion device 10 in the disc space.

Although the following discussion relates to the second endplate 16, it should be understood that it also equally applies to the first endplate 14 as the second endplate 16 is substantially identical to the first endplate 14 in embodiments of the present invention. With additional reference to FIG. 24, in an exemplary embodiment, the second endplate 16 has a first end 39 and a second end 41. In the illustrated embodiment, the second endplate 16 further comprise an upper surface 40 connecting the first end 39 and the second end 41, and a lower surface 42 connecting the first end 39 and the second end 41. While not illustrated, in an embodiment, the second endplate 16 further comprises a through opening. The through opening, in an exemplary embodiment, is sized to receive bone graft or similar bone growth inducing material.

In one embodiment, the upper surface 40 of the second endplate 16 is flat and generally planar to allow the upper surface 40 of the endplate 16 to engage with the adjacent vertebral body 2. Alternatively, as shown in FIG. 15, the upper surface 40 can be curved convexly or concavely to allow for a greater or lesser degree of engagement with the adjacent vertebral body 2. It is also contemplated that the upper surface 40 can be generally planar but includes a generally straight ramped surface or a curved ramped surface. The ramped surface allows for engagement with the adjacent vertebral body 2 in a lordotic fashion. While not illustrated, in an exemplary embodiment, the upper surface 40 includes texturing to aid in gripping the adjacent vertebral bodies. Although not limited to the following, the texturing can include teeth, ridges, friction increasing elements, keels, or gripping or purchasing projections.

In one embodiment, the second endplate 16 further comprises a first side portion 202 connecting the first end 39 and the second end 41, and a second side portion 204 connecting the first end 39 and the second end 41. In the illustrated embodiment, the first and second side portions 202, 204 are extensions from the lower surface 42. In an exemplary embodiment, the first and second side portions 202, 204 each include ramped surfaces 206, 208. In the illustrated embodiment, the ramped surfaces 206, 208 extend from the first end 39 of the second endplate 16 to bottom surfaces 210, 212 of each of the side portions 202, 204. In one embodiment, the ramped surfaces 206, 208 are forward facing in that the ramped surfaces 206, 208 face the first end 39 of the second endplate. As previously discussed, the slope of the ramped surfaces 206, 208 may be varied as desired for a particular application.

Figure 24:
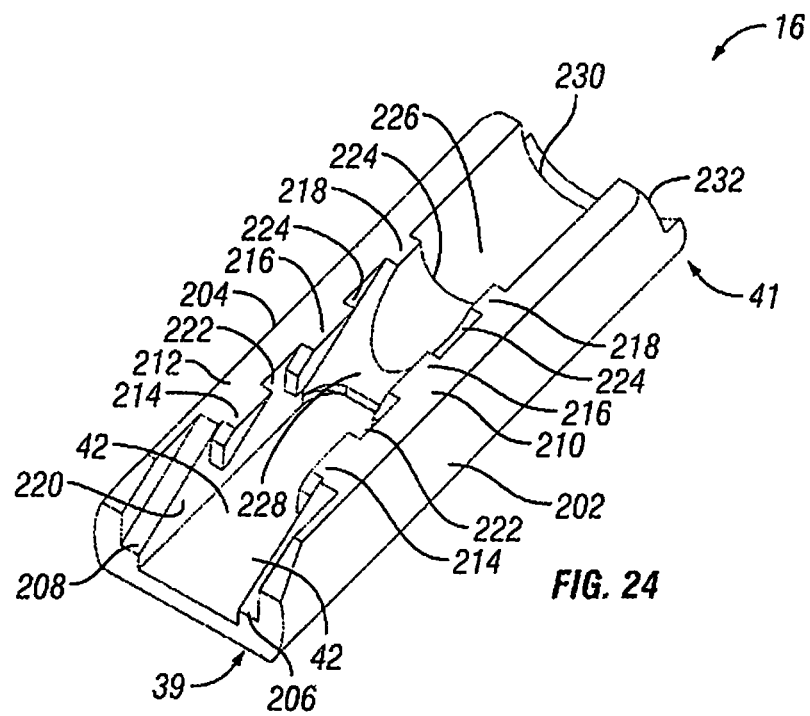
FIG. 24 is a perspective of an endplate of the expandable fusion device of FIG. 18 in accordance with one embodiment of the present invention.

In an embodiment, the first and second side portions 202, 204 each comprise at least one protuberance 214. In an exemplary embodiment, the first and second side portions 202, 204 each comprise a first protuberance 214, a second protuberance 216, and a third protuberance 218. In one embodiment, the protuberances 214, 216, 218 extend from the interior surface 220 of the first and second side portions 202, 204. In an exemplary embodiment, the protuberances 214, 216, 218 extend at the lower side of the interior surface 220. As best seen in FIG. 24, the first and the second protuberances 214, 216 form a first slot 222, and the second and third protuberances 216, 218 form a second slot 224.

As best seen in FIG. 24, the lower surface 42 of the second endplate 16, in an embodiment, includes a central extension 224 extending along at least a portion of the lower surface. In the illustrated embodiment, the central extension 224 extends between the first and second side portions 202 and 204. In an exemplary embodiment, the central extension 224 can extend from the second end 41 of the endplate 16 to the central portion of the endplate. In one embodiment, the central extension 224 includes a generally concave surface 226 configured and dimensioned to form a through bore with the corresponding concave surface 226 (not illustrated) of the first endplate 14. The central extension 224 can further include, in an exemplary embodiment, a ramped surface 228. In the illustrated embodiment, the ramped surface 228 faces the first end 39 of the endplate 16. The ramped surface 228 can be at one end of the central extension 224. In an embodiment, the other end of the central extension 224 forms a stop 230. In the illustrated embodiment, the stop 230 is recessed from the second end 41 of the second endplate 16.

Figure 25:
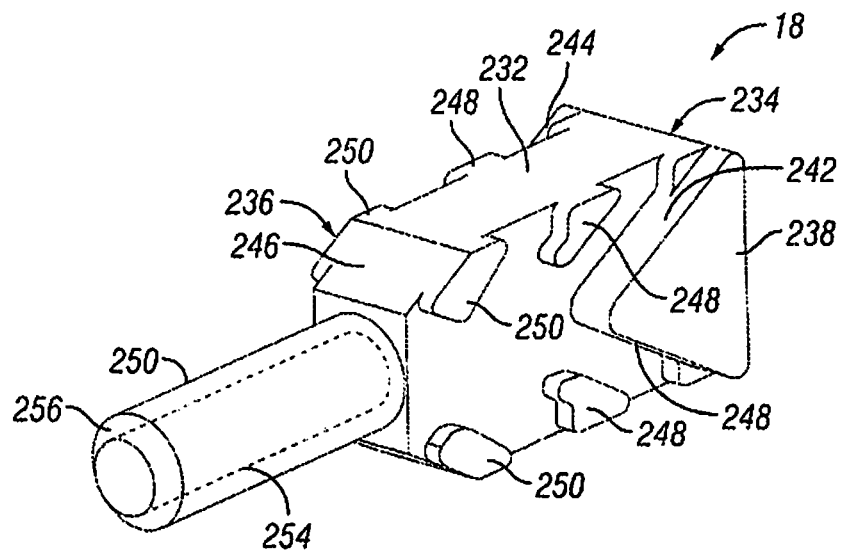
FIG. 25 is a perspective view of the central ramp of the expandable fusion device of FIG. 18 in accordance with one embodiment of the present invention.
Figure 26:
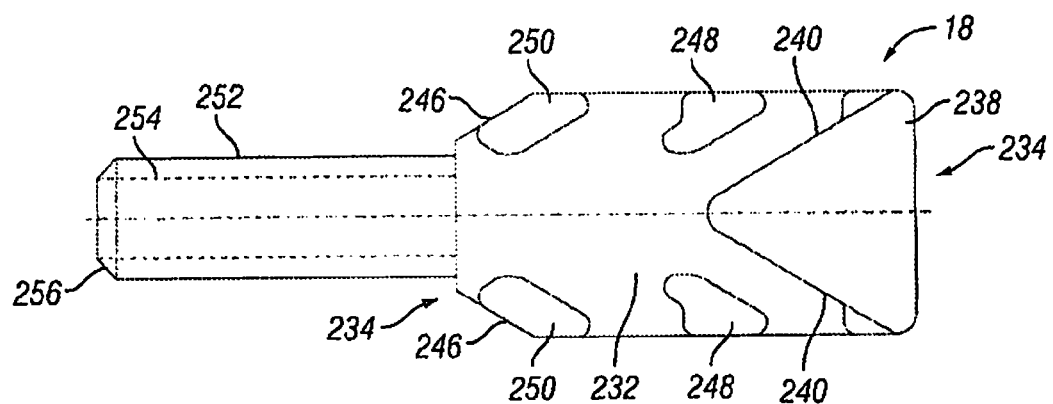
FIG. 26 is a side view of the central ramp of the expandable fusion device of FIG. 18 in accordance with one embodiment of the present invention.
Figure 27:
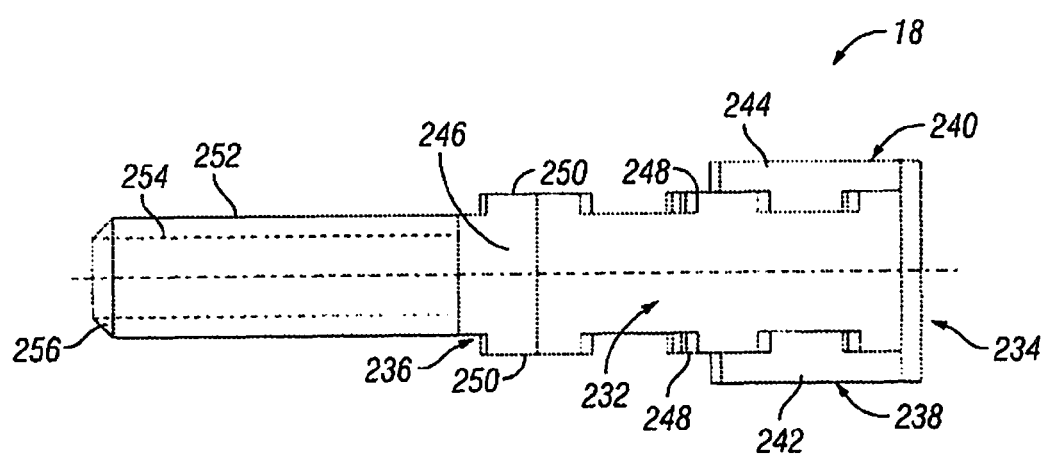
FIG. 27 is a top view of the central ramp of the expandable fusion device of FIG. 18 in accordance with one embodiment of the present invention.

Referring to FIGS. 25-27, in an exemplary embodiment, the central ramp 18 includes a body portion 232 having a first end 234 and a second end 236. In an embodiment, the body portion 232 includes at least a first expansion portion 238. In an exemplary embodiment, the body portion 232 includes a first expansion portion 238 and a second expansion portion 240 extending from opposing sides of the body portion with each of the first and second expansion portions 238, 240 having a generally triangular cross-section. In one embodiment, the expansion portions 238, 240 each have angled surfaces 242, 244 configured and dimensioned to engage the ramped surfaces 206, 208 of the first and second endplates 14, 16 and force apart the first and second endplates 14, 16. In an embodiment, the engagement between the angled surfaces 242, 244 of the expansion portions 238, 240 with the ramped surfaces 206, 208 of the first and second endplates 14, 16 may be described as a dovetail connection.

The second end 236 of the central ramp 18, in an exemplary embodiment, includes opposing angled surfaces 246. The angled surfaces 246 can be configured and dimensioned to engage the ramped surface 228 in the central extension 224 in each of the first and second endplates 14, 16. In other words, one of the angled surfaces 246 can be upwardly facing and configured, in one embodiment, to engage the ramped surface 228 in the central extension 224 in the second endplate 16. In an embodiment, the engagement between the angled surfaces 246 of the second end 236 of the central ramp 18 with the ramped surface 228 in the first and second endplates 14, 16 may be described as a dovetail connection.

The second end 236, in an exemplary embodiment, can further include an extension 252. In the illustrated embodiment, the extension 252 is generally cylindrical in shape with a through bore 254 extending longitudinally therethrough. In one embodiment, the extension 252 can include a beveled end 256. While not illustrated, at least a portion of the extension 252 can be threaded.

Figure 19:
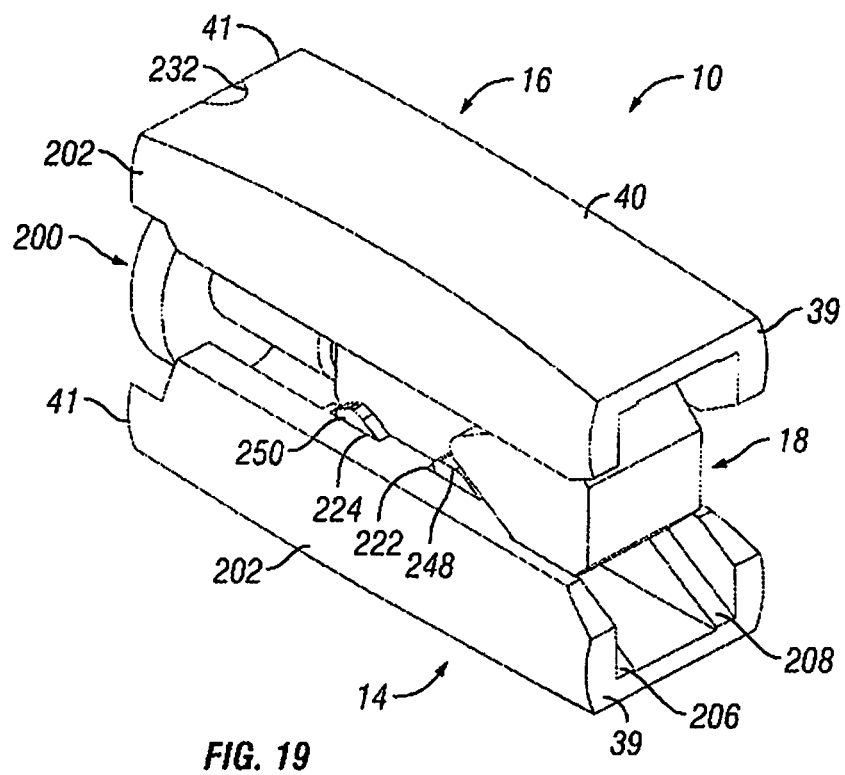
FIG. 19 is a front perspective view of the expandable fusion device of FIG. 18 shown in an expanded position in accordance with one embodiment of the present invention.
Figure 20:
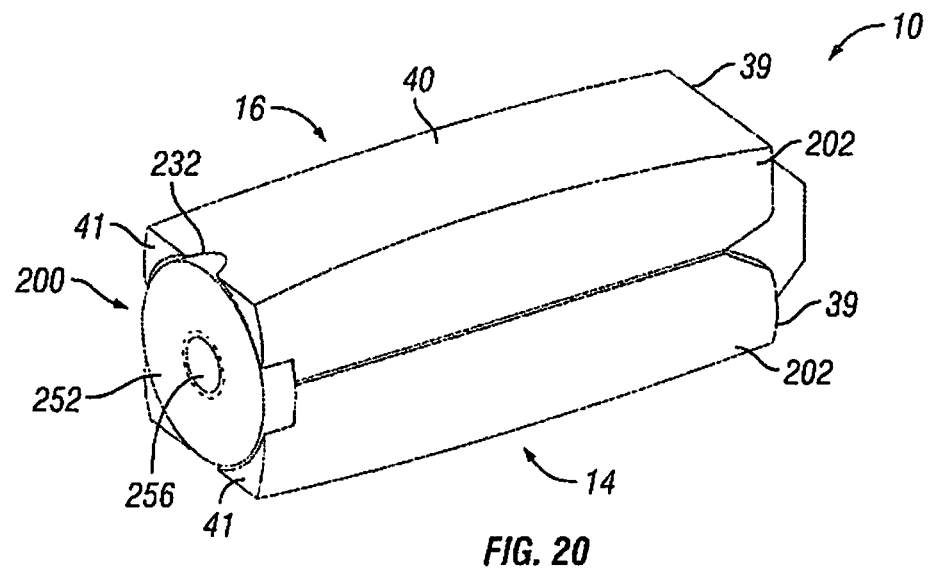
FIG. 20 is a rear perspective view of the expandable fusion device of FIG. 18 shown in an unexpanded position in accordance with one embodiment of the present invention.
Figure 21:
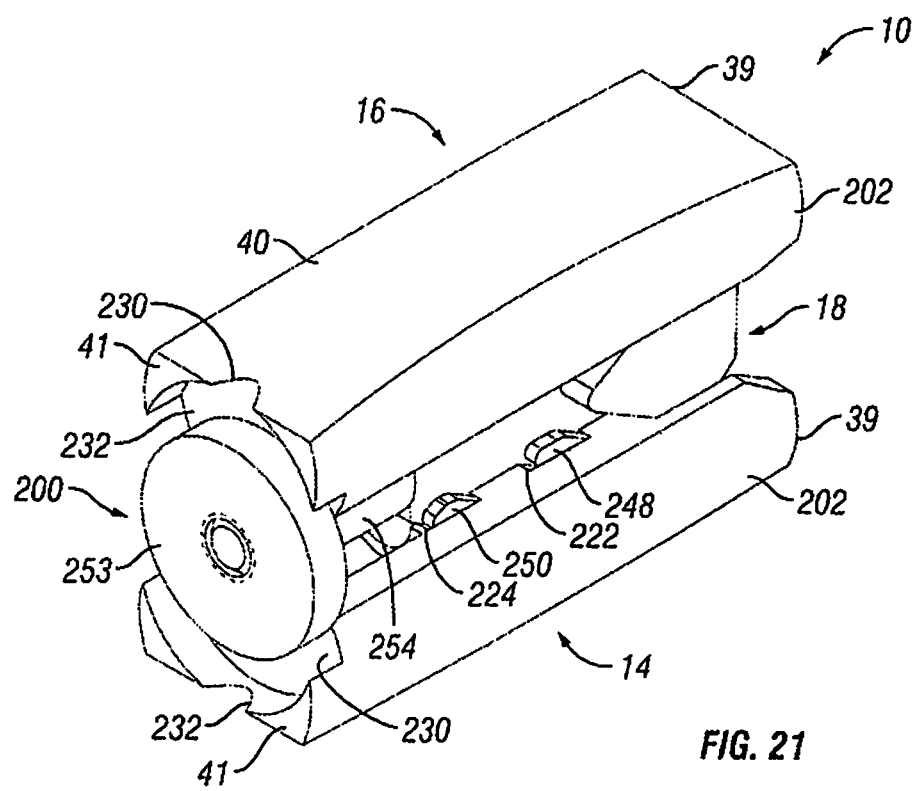
FIG. 21 is a rear perspective view of the expandable fusion device of FIG. 18 shown in an expanded position in accordance with one embodiment of the present invention.

Referring still to FIGS. 25-27, the central ramp 18 can further include features for securing the first and second endplates 14, 16 when the expandable fusion device 10 is in an expanded position. In an embodiment, the body portion 232 of the central ramp 18 includes one or more protuberances 248, 250 extending from opposing sides of the body portion 232. As illustrated, the protuberances 248, 250, in one embodiment, can be spaced along the body portion 232. In an exemplary embodiment, the protuberances 248, 250 can be configured and dimensioned for insertion into the corresponding slots 222, 224 in the first and second endplates 14, 16 when the device 10 is in an expanded position, as best seen in FIGS. 19 and 21. The protuberances 248, 250 can engage the endplates 14, 16 preventing and/or restricting movement of the endplates 14, 16 with respect to the central ramp 18 after expansion of the device 10.

With reference to FIGS. 20-23, in an exemplary embodiment, the actuator assembly 200 has a flanged end 253 configured and dimensioned to engage the stop 232 in the central extension 224 of the first and the second endplates 14, 16. In an embodiment, the actuator assembly 200 further includes an extension 254 that extends from the flanged end 253. In a further embodiment, the actuator assembly 200 includes a threaded hole 256 that extends through the actuator assembly 200. It should be understood that, while the threaded hole 256 in the actuator assembly 200 is referred to as threaded, the threaded hole 256 may only be partially threaded in accordance with one embodiment. In an exemplary embodiment, the threaded hole 256 is configured and dimensioned to threadingly receive the extension 252 of the central ramp 18.

Figure 28:
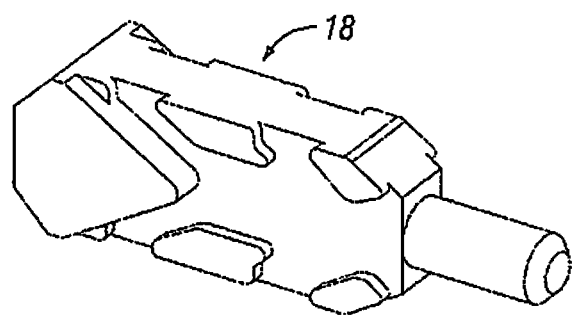
FIG. 28 a perspective view showing placement of the central ramp of the expandable fusion device of FIG. 18 in accordance with one embodiment of the present invention.
Figure 29:
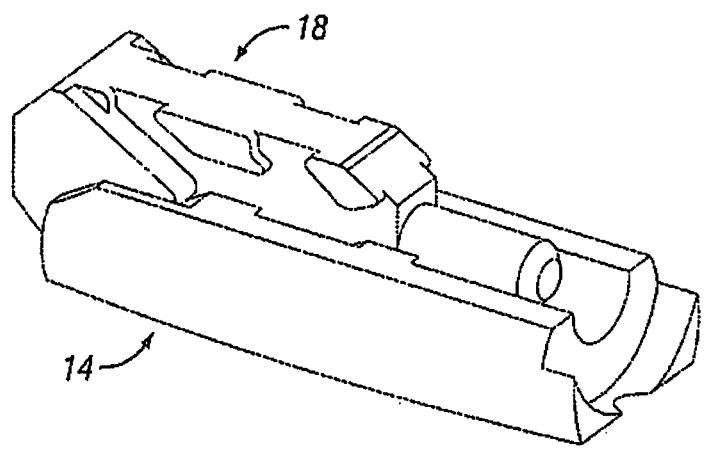
FIG. 29 is a perspective view showing placement of the first endplate of the expandable fusion device of FIG. 18 in accordance with one embodiment of the present invention.
Figure 30:
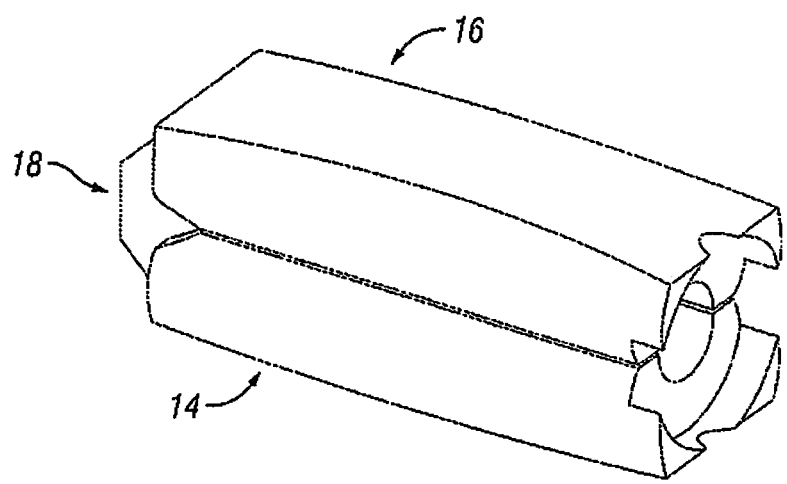
FIG. 30 is a perspective view showing placement of the second endplate of the expandable fusion device of FIG. 18 in accordance with one embodiment of the present invention.
Figure 31:
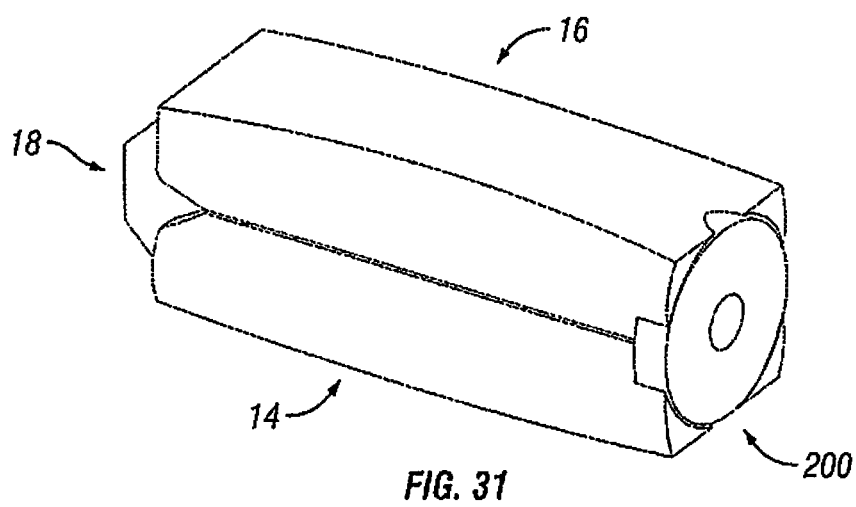
FIG. 31 is a perspective view showing placement of the actuation member of the expandable fusion device of FIG. 18 in accordance with one embodiment of the present invention.
Figure 32:
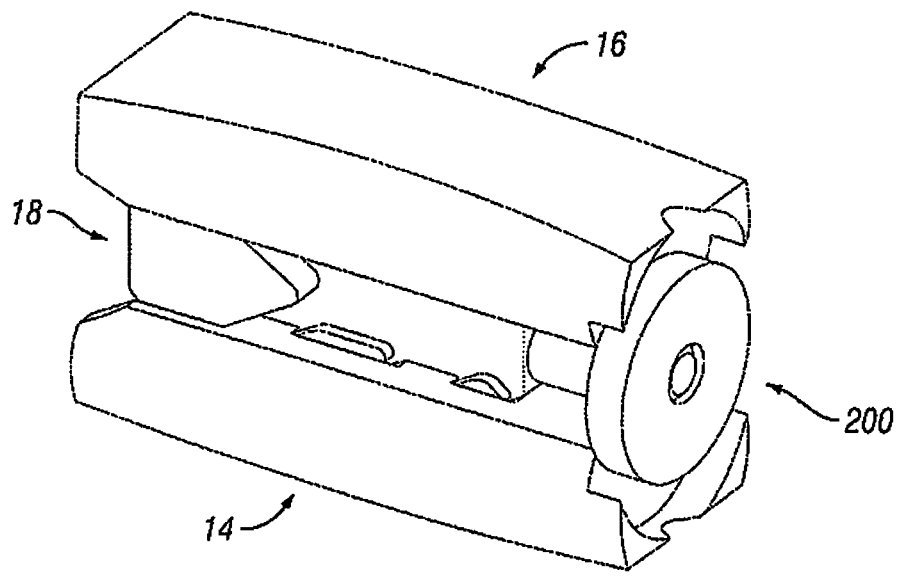
FIG. 32 is a perspective view showing expansion of the expandable fusion device of FIG. 18 in accordance with one embodiment of the present invention.
Figure 33:
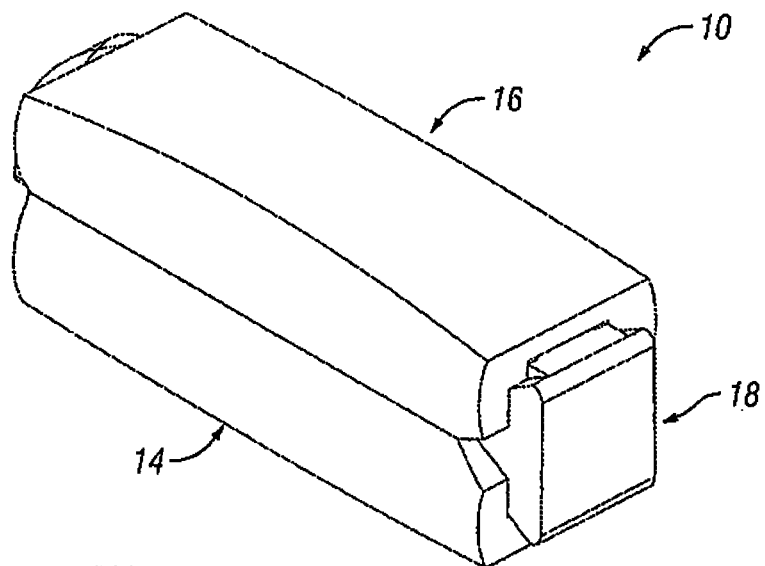
FIG. 33 is a front perspective view of an alternative embodiment of an expandable fusion device shown in an unexpanded position in accordance with one embodiment of the present invention.
Figure 34:
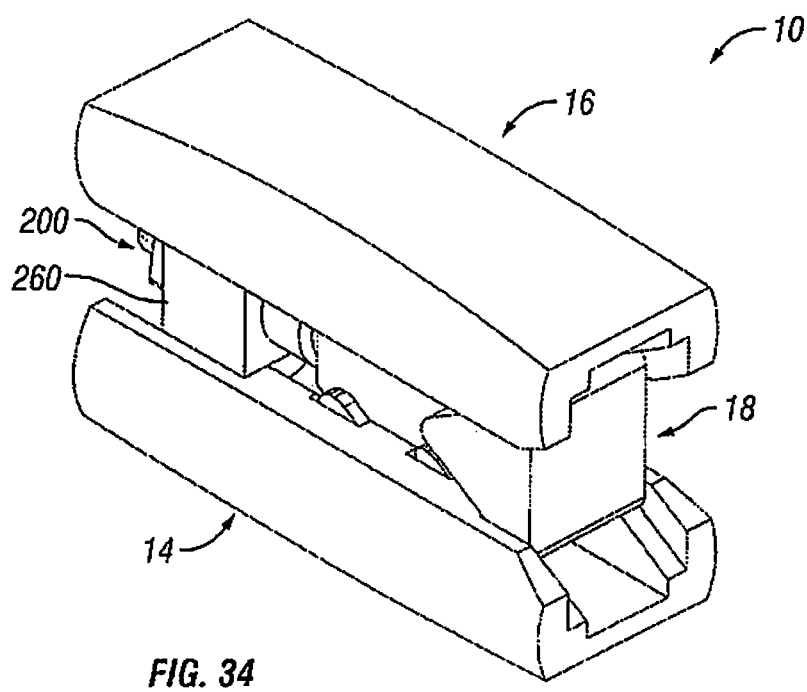
FIG. 34 is a front perspective view of the expandable fusion device of FIG. 33 shown in an expanded position in accordance with one embodiment of the present invention.
Figure 35:
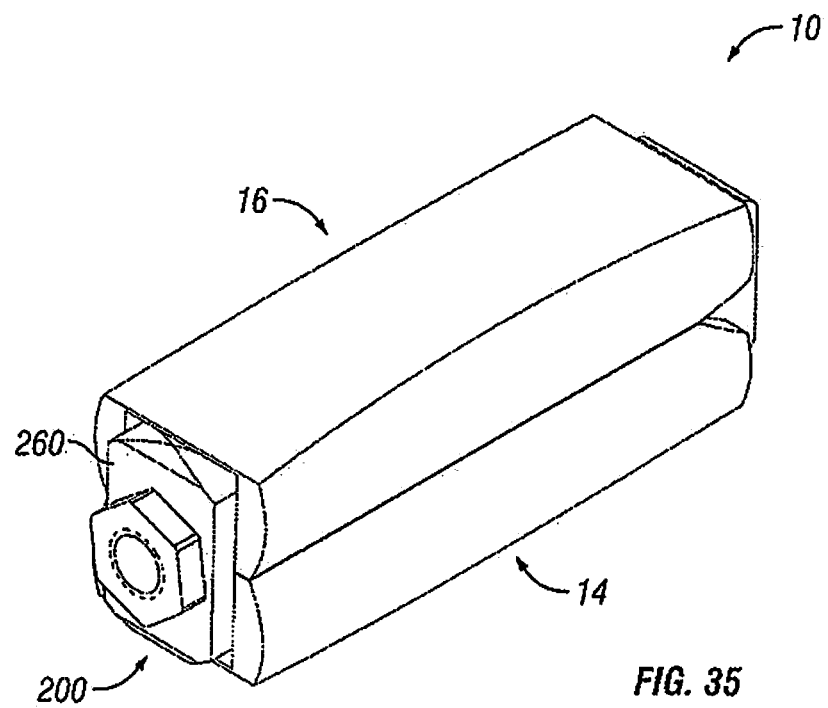
FIG. 35 is a rear perspective view of the expandable fusion device of FIG. 33 shown in an unexpanded position in accordance with one embodiment of the present invention.
Figure 36:
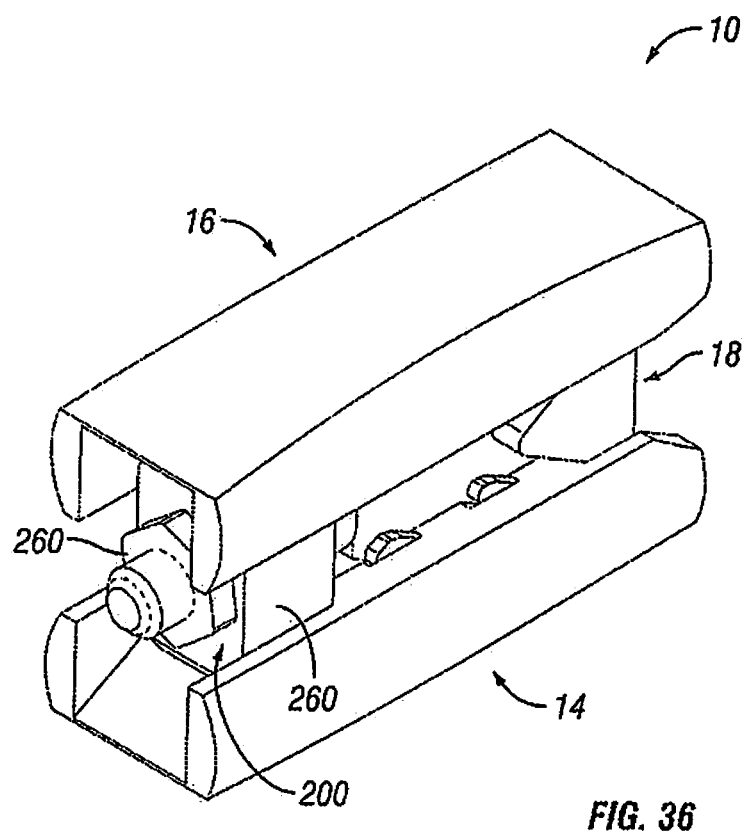
FIG. 36 is a rear perspective view of the expandable fusion device of FIG. 33 shown in an expanded position in accordance with one embodiment of the present invention.
Figure 37:
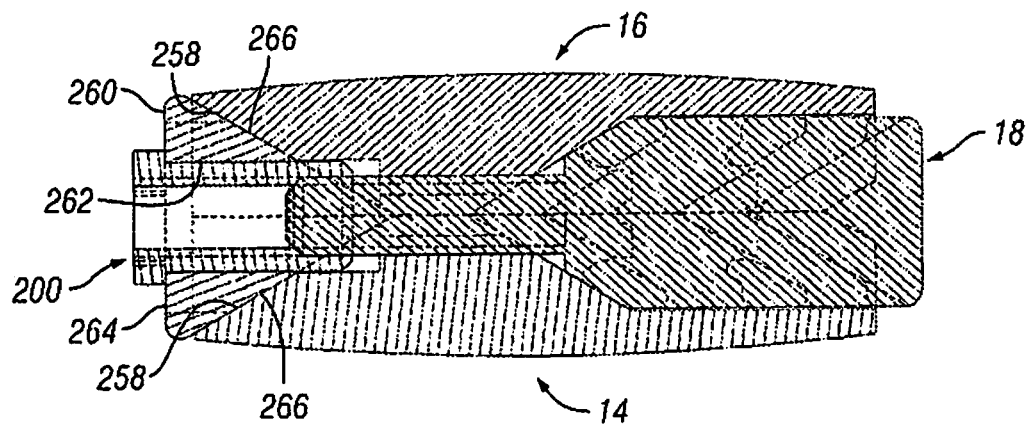
FIG. 37 is a side cross-sectional view of the expandable fusion device of FIG. 33 shown in an unexpanded position in accordance with one embodiment of the present invention.
Figure 38:
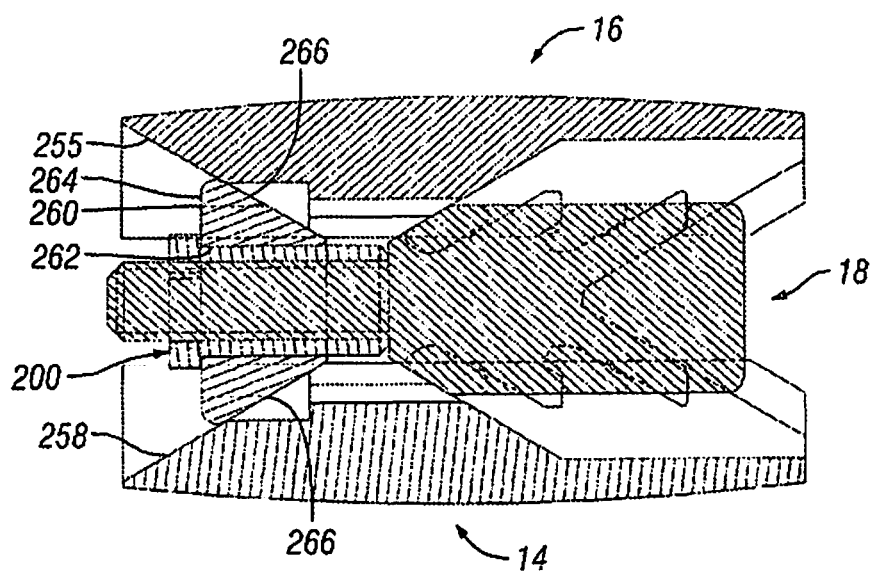
FIG. 38 is a side cross-sectional view of the expandable fusion device of FIG. 33 shown in an expanded position in accordance with one embodiment of the present invention.

With additional reference to FIGS. 28-32, a method of installing the expandable fusion device 10 of FIGS. 18-27 is now discussed in accordance with one embodiment of the present invention. Prior to insertion of the fusion device, the disc space may be prepared as described above and then one or more endoscopic tubes may then inserted into the disc space. The expandable fusion device 10 can then be inserted into and seated in the appropriate position in the intervertebral disc space, as best seen in FIGS. 28-32. The expandable fusion device 10 can be introduced into the intervertebral space down an endoscopic tube (not illustrated), with the central ramp 18 being first placed down the tube and into the disc space, as seen in FIG. 28. After insertion of the central ramp, the first endplate 14 can be placed down an endoscopic tube, as shown on FIG. 29, followed by insertion of the second endplate 16, as shown on FIG. 30. After the second endplate 16, the actuator assembly 200 can then be inserted to complete assembly of the device 10, as best seen in FIG. 31.

Figure 22:
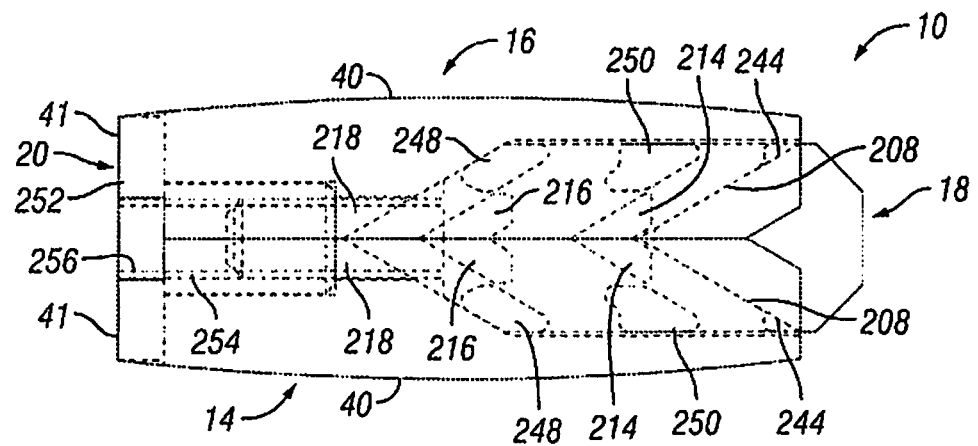
FIG. 22 is a side view of the expandable fusion device of FIG. 18 shown in an unexpanded position in accordance with one embodiment of the present invention.
Figure 23:
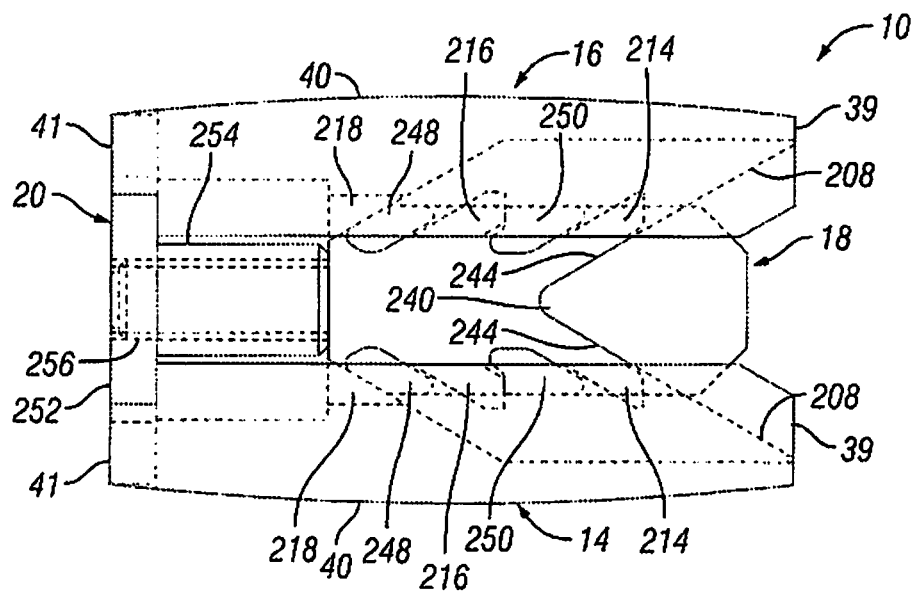
FIG. 23 is a side view of the expandable fusion device of FIG. 18 shown in an expanded position in accordance with one embodiment of the present invention.

After the fusion device 10 has been inserted into and assembled in the appropriate position in the intervertebral disc space, the fusion device 10 can then be expanded into the expanded position. To expand the fusion device 10, the actuator assembly 200 can be rotated. As discussed above, the actuator assembly 200 is in threaded engagement with the extension 250 of the central ramp 18. Thus, as the actuator assembly 200 is rotated in a first direction, the central ramp 18 moves toward the flanged end 253 of the actuator assembly 200. In another exemplary embodiment, the actuator assembly 200 can be moved in a linear direction with the ratchet teeth as means for controlling the movement of the central ramp 18. As the central ramp 18 moves, the angled surfaces 242, 244 in the expansion portions 238, 240 of the central ramp 18 push against the ramped surfaces 206, 208 in the first and second side portions 202, 204 of the first and second endplates 14, 16. In addition, the angled surfaces 246 in the second end 236 of the central ramp 18 also push against the ramped surfaces 228 in the central extension 224 of each of the endplates 14, 16. This is best seen in FIGS. 22-23.

Since the expansion of the fusion device 10 is actuated by a rotational input, the expansion of the fusion device 10 is infinite. In other words, the endplates 14, 16 can be expanded to an infinite number of heights dependent on the rotational advancement of the actuator assembly 200. As discussed above, the central ramp 16 includes locking features for securing the endplates 14, 16.

In the event the fusion device 10 needs to be repositioned or revised after being installed and expanded, the fusion device 10 can be contracted back to the unexpanded configuration, repositioned, and expanded again once the desired positioning is achieved. To contract the fusion device 10, the actuator assembly 200 can be rotated in a second direction. As discussed above, actuator assembly 200 is in threaded engagement with the extension 250 of the central ramp 18; thus, as the actuator assembly 200 is rotated in a second direction, opposite the first direction, the central ramp 18 moves with respect to the actuator assembly 200 and the first and second endplates 14, 16 away from the flanged end 253. As the central ramp 18 moves, the first and second endplates are pulled inwardly into the unexpanded position.

Referring now to FIGS. 33-38, an alternative embodiment of the expandable fusion device 10 is shown. In the illustrated embodiment, the fusion device includes a first endplate 14, a second endplate 16, a central ramp 18, and an actuator assembly 200. The fusion device 10 of FIGS. 33-38 and its individual components are similar to the device 10 illustrated on FIGS. 18-23 with several modifications. The modifications to the device 10 will be described in turn below.

Figure 39:
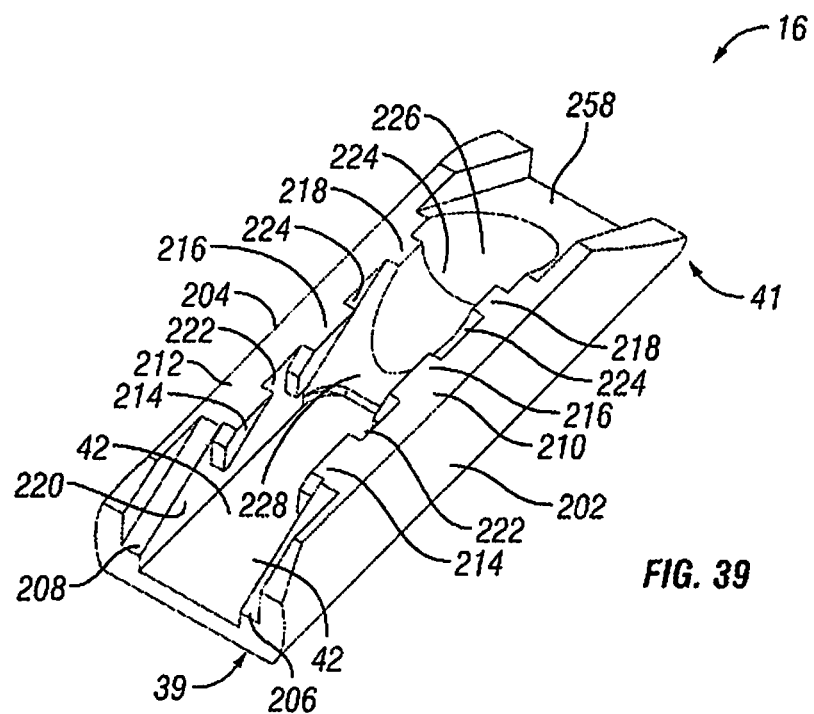
FIG. 39 is a perspective of an endplate of the expandable fusion device of FIG. 33 in accordance with one embodiment of the present invention.

Although the following discussion relates to the second endplate 16, it should be understood that it also equally applies to the first endplate 14 as the second endplate 16 is substantially identical to the first endplate 14 in embodiments of the present invention. With additional reference to FIG. 39, in an exemplary embodiment, the lower surface 42 of the second endplate 16 has been modified. In one embodiment, the central extension 224 extending from the lower surface 42 has been modified to include a second ramped surface 258 rather than a stop. In an exemplary embodiment, the second ramped surface 258 faces the second end 41 of the second endplate 16. In contrast, ramped surface 228 on the central extension 228 faces the first end 39 of the second endplate. The concave surface 228 connects the ramped surface 228 and the second ramped surface 258.

With reference to FIGS. 35-38, in an exemplary embodiment, the actuator assembly 200 has been modified to further include a driving ramp 260. In the illustrated embodiment, the driving ramp 260 has a through bore 262 through which the extension 254 extends. In an embodiment, the driving ramp 260 is generally wedge-shaped. As illustrated, the driving ramp 260 may comprise a blunt end 264 in engagement with the flanged end 253. In an exemplary embodiment, the driving ramp 260 further comprises angled surfaces 266 configured and dimensioned to engage the second ramped surface 258 of each of the endplates 14, 16 and force apart the first and second endplates 14, 16.

Referring now to FIGS. 40-44, an alternative embodiment of the expandable fusion device 10 is shown. In the illustrated embodiment, the fusion device 10 includes a first endplate 14, a second endplate 16, a central ramp 18, an actuator assembly 200, and a driving ramp 300. As will be discussed in more detail below, the actuator assembly 200 functions, in an embodiment, to pull the central ramp 18 and the driving ramp 300 together, which forces apart the first and second endplates 14, 16. In an embodiment, the expandable fusion device Although the following discussion relates to the first endplate 14, it should be understood that it also equally applies to the second endplate 16 as the second endplate 16 is substantially identical to the first endplate 14 in embodiments of the present invention. With reference to FIGS. 40-45, in an exemplary embodiment, the first endplate 14 has a first end 39 and a second end 41. In the illustrated embodiment, the first endplate 14 further comprises an upper surface 40 connecting the first end 39 and the second end 41, and a lower surface 42 connecting the first end 39 and the second end 41. While not illustrated, in an embodiment, the first endplate 14 may comprise further comprises a through opening. The through opening, in an exemplary embodiment, is sized to receive bone graft or similar bone growth inducing material.

In one embodiment, the upper surface 40 of the first endplate 14 is flat and generally planar to allow the upper surface 40 of the endplate 14 to engage with the adjacent vertebral body 2. Alternatively, as shown in FIG. 15, the upper surface 40 can be curved convexly or concavely to allow for a greater or lesser degree of engagement with the adjacent vertebral body 2. It is also contemplated that the upper surface 40 can be generally planar but includes a generally straight ramped surface or a curved ramped surface. The ramped surface allows for engagement with the adjacent vertebral body 2 in a lordotic fashion. While not illustrated, in an exemplary embodiment, the upper surface 40 includes texturing to aid in gripping the adjacent vertebral bodies. Although not limited to the following, the texturing can include teeth, ridges, friction increasing elements, keels, or gripping or purchasing projections.

In one embodiment, the first endplate 14 further comprises a first side portion 202 connecting the first end 39 and the second end 41, and a second side portion 204 connecting the first end 39 and the second end 41. In the illustrated embodiment, the first and second side portions 202, 204 are extensions from the lower surface 42. In an embodiment, the first and second side portions each have an interior surface 302 and an exterior surface 304. In an exemplary embodiment, the first and second side portions 202, 204 each include one or more ramped portions. In the illustrated embodiment, the first and second side portions 202, 204 include first ramped portions 306, 308 at the first end 39 of the endplate 14 and second ramped portions 310, 312 at the second end 41 of the endplate. The first and second side portions 202, 204 each can include a bridge portion 314 connecting the first ramped portions 306, 308 and the second ramped portions 310, 312. In an embodiment, the first ramped portions 306, 308 abut the exterior surface 304 of the respective side portions 202, 204, and the second ramped portions 310, 312 abut the interior surface 302 of the respective side portions 202, 204. As illustrated, the first ramped portions 306, 308 may include tongue portions 316, 318 with the tongue portions 316, 318 extending in an oblique direction with respect to the upper surface 40 of the endplate 14. As further illustrated, the second ramped portions 310, 312 may include tongue portions 320, 322 that extend in an oblique direction with respect to the upper surface 40 of the endplate 14.

Figure 45:
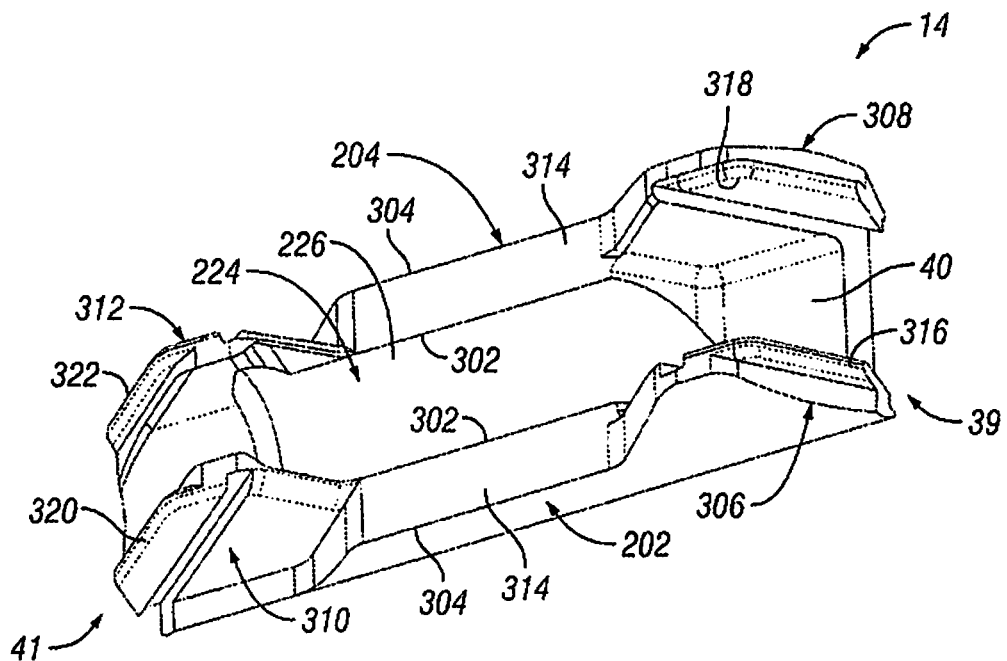
FIG. 45 is a perspective view of an endplate of the expandable fusion device of FIG. 40 in accordance with one embodiment of the present invention.

As best seen in FIG. 45, the lower surface 42 of the second endplate 16, in an embodiment, includes a central extension 224 extending along at least a portion of the lower surface. In the illustrated embodiment, the central extension 224 extends between the first and second side portions 202 and 204. In an exemplary embodiment, the central extension 224 can extend generally between the first ramped portions 306, 308 and the second ramped portions 310, 312. In one embodiment, the central extension 224 includes a generally concave surface 226 configured and dimensioned to form a through bore with the corresponding concave surface 226 (not illustrated) of the second endplate 16.

Figure 43:
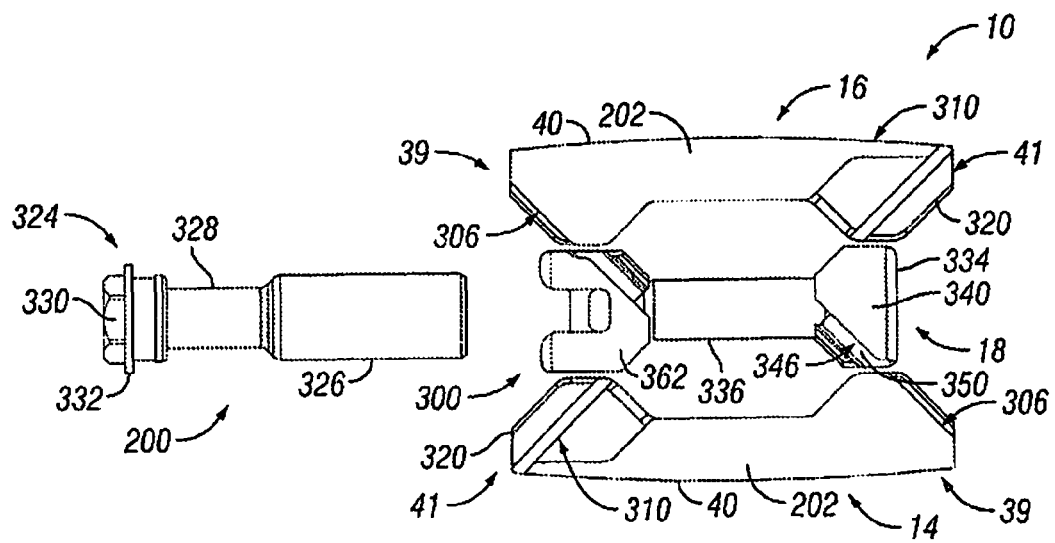
FIG. 43 is a side exploded view of the expandable fusion device of FIG. 40 in accordance with one embodiment of the present invention.
Figure 44:
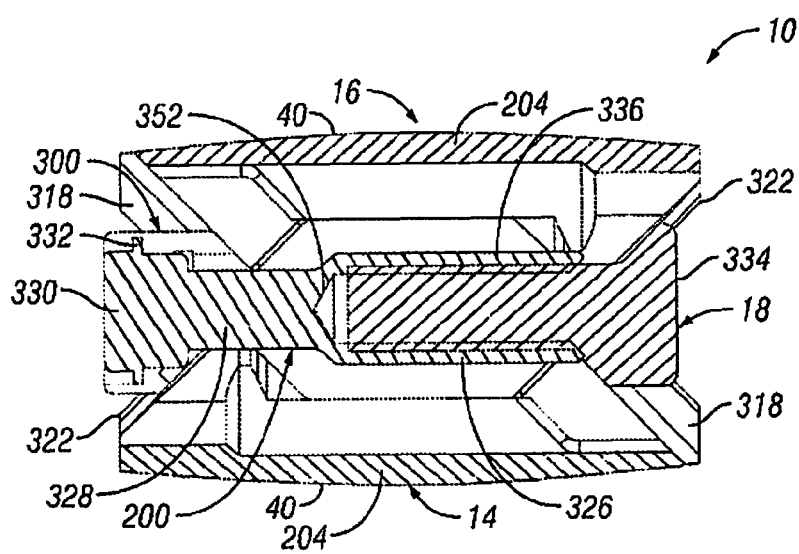
FIG. 44 is a side cross-sectional view of the expandable fusion device of FIG. 40 shown in an unexpanded position in accordance with one embodiment of the present invention.

With reference to FIGS. 43 and 44, the actuator assembly 200 includes a head portion 324, a rod receiving extension 326, and a connecting portion 328 that connecting portions that connects the head portion 324 and the rod receiving extension 326. As illustrated, the head portion 324 may include one or more instrument gripping features 330 that can allow it to be turned by a suitable instrument. In addition, the head portion 324 has a larger diameter than the other components of the actuator assembly 200 to provide a contact surface with the driving ramp 300. In the illustrated embodiment, the head portion 324 includes a rim 332 that provides a surface for contacting the driving ramp 300. As can be seen in FIG. 44, in an exemplary embodiment, the rod receiving extension 326 includes an opening sized and dimensioned to receive the extension 336 of the central ramp 18. In an embodiment, the rod receiving extension 326 includes threading for threadingly engaging the extension 336. In another embodiment, the rod receiving extension 326 includes ratchet teeth for engaging the extension 336. In the illustrated embodiment, the head portion 324 and the rod receiving extension 326 are connected by connecting portion 328 which can be generally cylindrical in shape.

Figure 46:
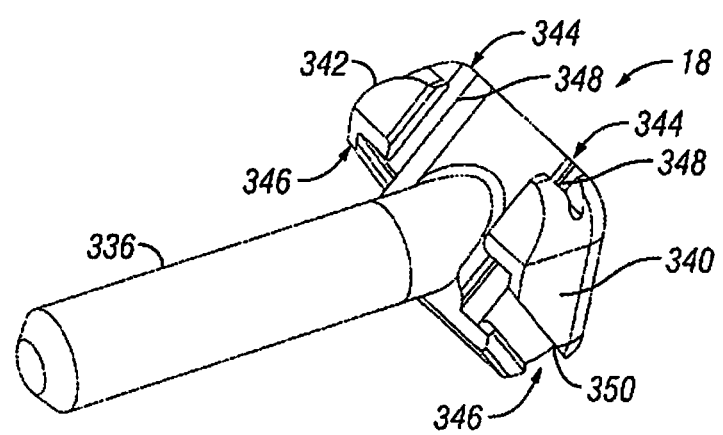
FIG. 46 is a perspective view of the central ramp of the expandable fusion device of FIG. 40 in accordance with one embodiment of the present invention.

With reference to FIGS. 43, 44, and 46, the central ramp 18 includes expansion portion 334 and extension 336. As best seen in FIG. 46, the expansion portion 334 may include an upper portion 338 and side portions 340, 342 that extend down from the upper portion 338. In an embodiment, each of the side portions 340, 342 include dual, overlapping ramped portions. For example, side portions 340, 342 each include a first ramped portion 344 that overlaps a second ramped portion 346. In the illustrated embodiment, the first ramped portion 344 faces the extension 336 while the second ramped portion 344 faces away from the extension 336. In one embodiment, angled grooves 348, 350 are formed in each of the first and second ramped portions 344, 346. In another embodiment, the angled grooves 348, 350 are sized to receive the corresponding tongues 316, 318, 320, 322 in the first and second endplates with angled grooves 348 receiving tongues 320, 322 in the second endplate 16 and angled grooves 350 receiving tongues 316, 318 in the first endplate 14. Although the device 10 is described with tongues 316, 318, 320, 322 on the endplates 14, 16 and angled grooves 348, 350 on the central ramp 18, it should be understood that that device 10 can also be configured with grooves on the endplates 14, 16 and tongues on the central ramp 18, in accordance with one embodiment of the present invention.

In an exemplary embodiment, the extension 336 is sized to be received within the rod receiving extension 326 of the actuator assembly 200. In one embodiment, the extension 336 has threading with the extension 336 being threadingly received within the rod receiving extension 326. In another embodiment, the extension 336 has ratchet teeth with the extension 336 being ratcheted into the rod receiving extension 336. In an embodiment, the extension 336 include nose 352 at the end of the extension 336.

Figure 47:
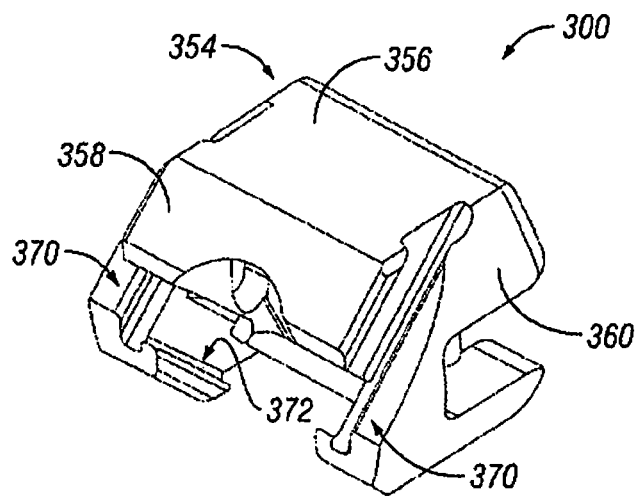
FIGS. 47-49 are perspective views of the driving ramp of the expandable fusion device of FIG. 40 in accordance with one embodiment of the present invention.
Figure 48:
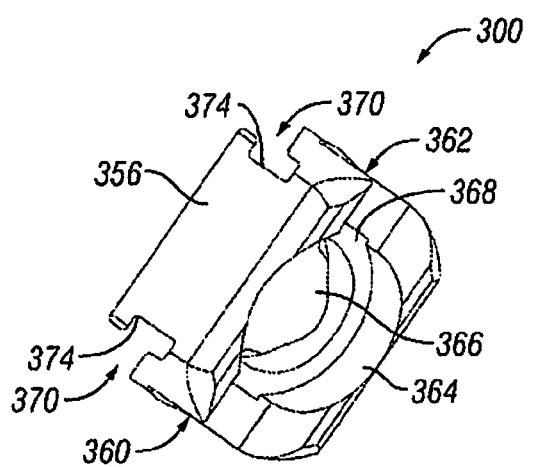
Figure 49:
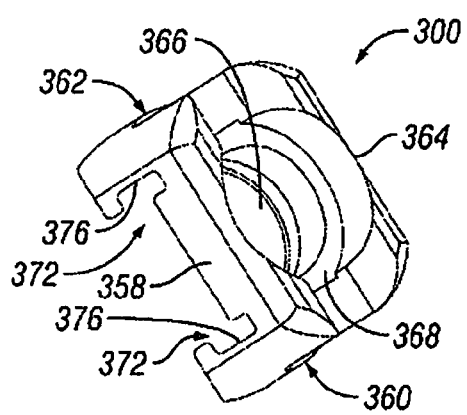
Figure 50:
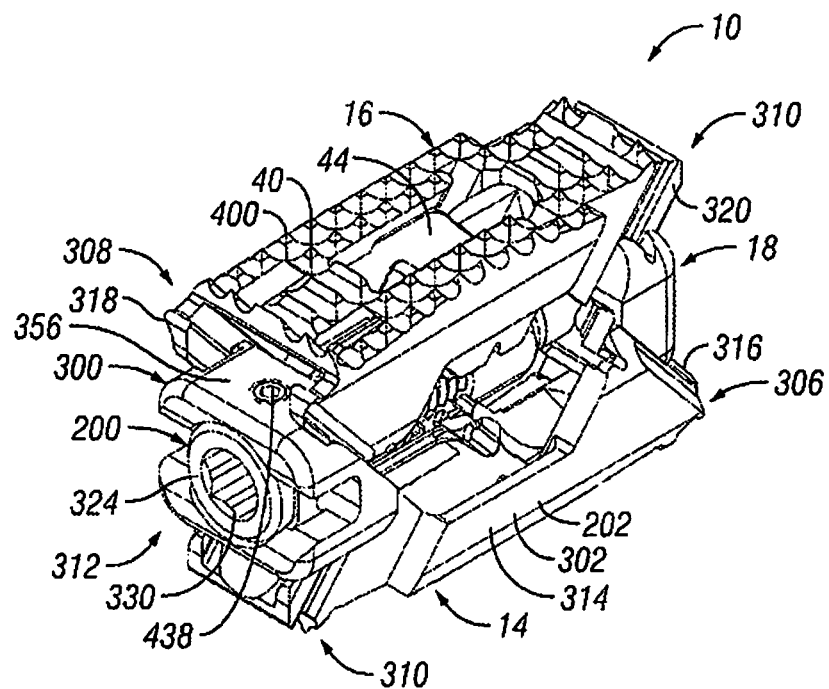
FIG. 50 is a rear perspective view of an alternative embodiment of an expandable fusion device shown in an expanded position in accordance with one embodiment of the present invention.

With reference to FIGS. 47-49, in an exemplary embodiment, the driving ramp 300 includes an upper portion 354 having an upper surface 356 and an oblique surface 358. In an embodiment, the driving ramp 300 further includes side portions 360, 362 that extend from the upper portion 354 connecting the upper portion 354 with the lower portion 364 of the driving ramp 300. As best seen in FIGS. 48-49, the driving ramp 300 further includes a bore 366, in an exemplary embodiment, sized to receive the connection portion 328 of the actuator assembly 200. In one embodiment, the driving ramp 300 moves along the connection portion 328 when the actuator assembly 200 is pushing the driving ramp 300. In an exemplary embodiment, the driving ramp 300 further includes contact surface 368 that engages the rim 332 of the head portion 324 of the actuator assembly 200. In the illustrated embodiment, the contact surface 368 has a generally annular shape.

In an exemplary embodiment, the side portions 360, 362 of the driving ramp 300 each include overlapping ramped portions. For example, the side portions 360, 362 each include first ramped portions 370 that overlap second ramped portions 372. In the illustrated embodiment, the first ramped portions 370 face central ramp 18 while the second ramped portions 372 face the opposite direction. In one embodiment, angled grooves 374, 376 are formed in each of the first and second ramped portions 370, 372. FIG. 48 is a perspective view of the driving ramp 300 that shows the top ends of the angled grooves 374 in ramped portions 370. FIG. 49 is a perspective view of the driving ramp 300 that shows the top ends of the angled grooves 376 in ramped portions 372. In an exemplary embodiment, the angled grooves 374, 376 are sized to receive corresponding tongues 316, 318, 320, 322 in the first and second endplates 14, 16 with angled grooves 370 receiving tongues 316, 318 in the second endplate 16 and angled grooves 372 receiving tongues 320, 322 in the first endplate 14. Although the device 10 is described with tongues 316, 318, 320, 322 in the first and second endplates 14, 16 and angled grooves 370, 372, 374, 376 on the driving ramp 300, it should be understood that that device 10 can also be configured with grooves on the second endplate 16 and tongues on the driving ramp 300, in accordance with one embodiment of the present invention.

Figure 40:
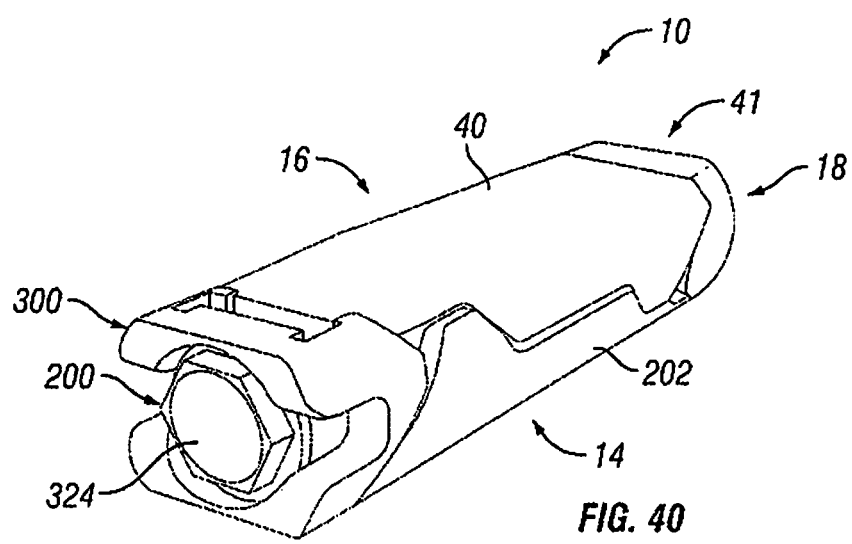
FIG. 40 is a rear perspective view of an alternative embodiment of an expandable fusion device shown in an unexpanded position in accordance with one embodiment of the present invention.
Figure 41:
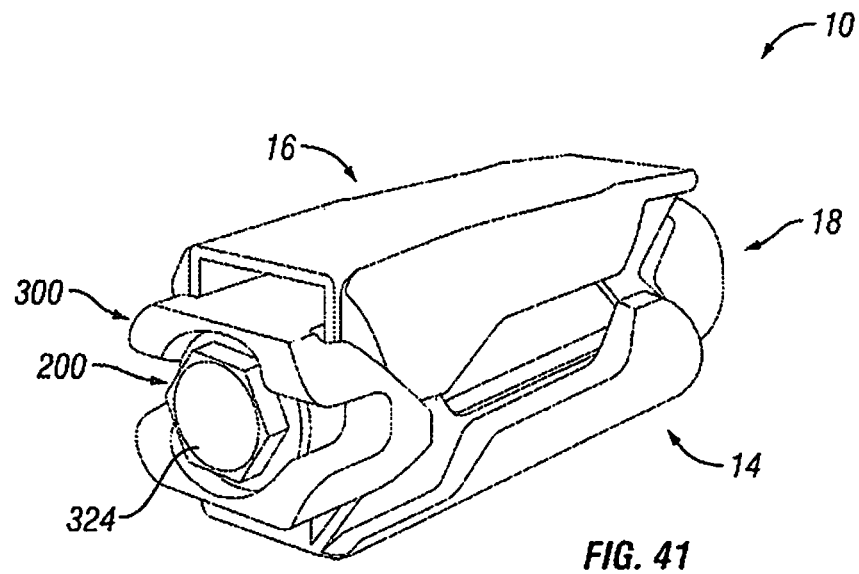
FIG. 41 is a rear perspective view of the expandable fusion device of FIG. 40 shown in a partially expanded position in accordance with one embodiment of the present invention.
Figure 42:
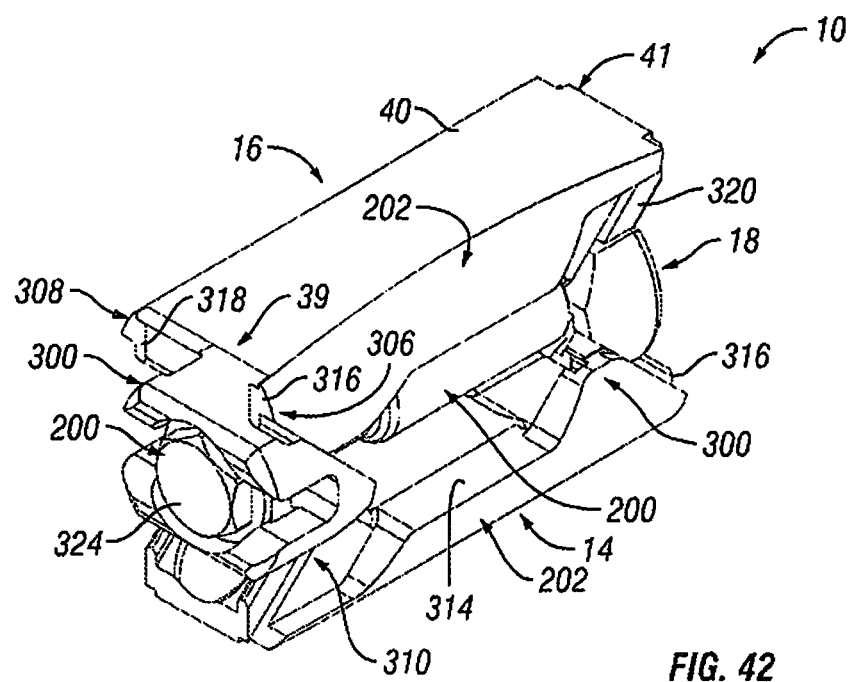
FIG. 42 is a rear perspective view of the expandable fusion device of FIG. 40 shown in an expanded position in accordance with one embodiment of the present invention.

Turning now to FIGS. 40-42, a method of installing the expandable fusion device 10 of FIGS. 40-49 is now discussed in accordance with one embodiment of the present invention. Prior to insertion of the fusion device, the disc space may be prepared as described above. The expandable fusion device 10 can then be inserted into and seated in the appropriate position in the intervertebral disc space. The expandable fusion device 10 is then introduced into the intervertebral space, with the end having the expansion portion 334 of the central ramp 18 being inserted. In an exemplary method, the fusion device 10 is in the unexpanded position when introduced into the intervertebral space. In an exemplary method, the intervertebral space may be distracted prior to insertion of the fusion device 10. The distraction provide some benefits by providing greater access to the surgical site making removal of the intervertebral disc easier and making scraping of the endplates of the vertebral bodies 2, 3 easier.

With the fusion device 10 inserted into and seated in the appropriate position in the intervertebral disc space, the fusion device can then expanded into the expanded position, as best seen in FIG. 42. To expand the fusion device 10, an instrument is engaged with the head portion 324 of the actuator assembly 200. The instrument is used to rotate actuator assembly 200. As discussed above, actuator assembly 200 is threadingly engaged with the extension 336 of the central ramp 18; thus, as the actuator assembly 200 is rotated in a first direction, the central ramp 18 is pulled toward the actuator assembly 200. In an exemplary embodiment, the actuator assembly 200 is moved in a linear direction with the ratchet teeth engaging as means for controlling the movement of the actuator assembly 200 and the central ramp 18. As the central ramp 18 is pulled towards the actuator assembly 200, the first ramped portions 344 of the central ramp 18 push against the second ramped portions 310, 312 of the second endplate 16 and the second ramped portions 346 of the central ramp 18 push against first ramped portions 306, 308 of the first endplate 14. In this manner, the central ramp 18 acts to push the endplates 14, 16 outwardly into the expanded position. This can best be seen in FIGS. 40-42. As the endplates 14, 16 move outwardly the tongues 316, 318, 320, 322 in the endplates 14, 16 ride in the angled grooves 348, 350 with the tongues 320, 322 in the second endplate 16 riding in angled grooves 348 and the tongues 316, 318 in the first endplate 14 riding in angled grooves 350.

As discussed above, the actuator assembly 200 also engages driving ramp 300; thus, as the actuator assembly 200 is rotated in a first direction, the actuator assembly 200 pushes the driving ramp 300 towards the central ramp 18 in a linear direction. As the driving ramp 300 is pushed towards the central ramp 18, the first ramped portions 370 of the driving ramp 300 push against the first ramped portions 306, 308 of the second endplate 16 and the second ramped portions 372 of the driving ramp 300 push against the second ramped portions 310, 312 of the first endplate 14. In this manner, the driving ramp 300 also acts to push the endplates 14, 16 outwardly into the expanded position. This can best be seen in FIGS. 40-42.

As the endplates 14, 16 move outwardly the tongues 316, 318, 320, 322 in the endplates 14, 16 ride in the angled grooves 370, 372 with the tongues 316, 318 in the second endplate 16 riding in angled grooves 370 and the tongues 320, 322 in the first endplate 14 riding in angled grooves 372.

Since the expansion of the fusion device 10 is actuated by a rotational input, the expansion of the fusion device 10 is infinite. In other words, the endplates 14, 16 can be expanded to an infinite number of heights dependent on the rotational advancement of the actuator assembly 200.

Referring now to FIGS. 50-54, an alternative embodiment of the expandable fusion device 10 is shown. In the illustrated embodiment, the fusion device 10 includes a first endplate 14, a second endplate 16, a central ramp 18, an actuator assembly 200, and a driving ramp 300. As will be discussed in more detail below, the actuator assembly 200 functions, in an embodiment, to pull the central ramp 18 and the driving ramp 300 together, which forces apart the first and second endplates 14, 16. In an embodiment, the expandable fusion device may contain features, such as a through bore, that facilitate placement down an endoscopic tube. In an embodiment, the assembled fusion device 10 may be placed down the endoscopic tube and then expanded.

Figure 54:
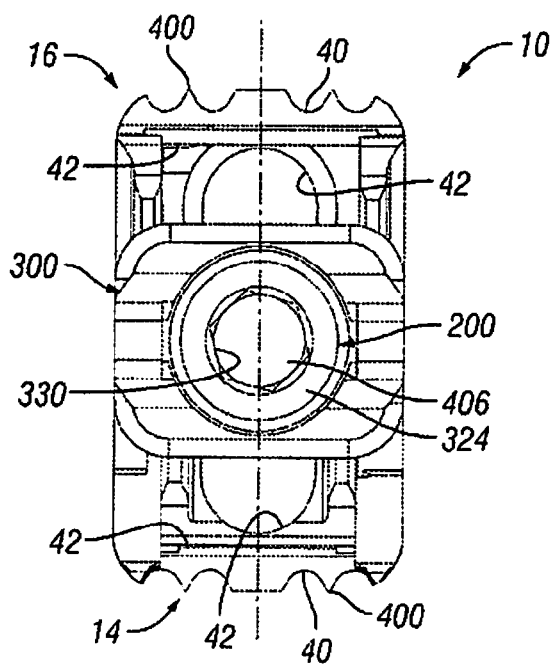
FIG. 54 is a read end view of the expandable fusion device of FIG. 50 shown in an expanded position in accordance with one embodiment of the present invention.
Figure 55:
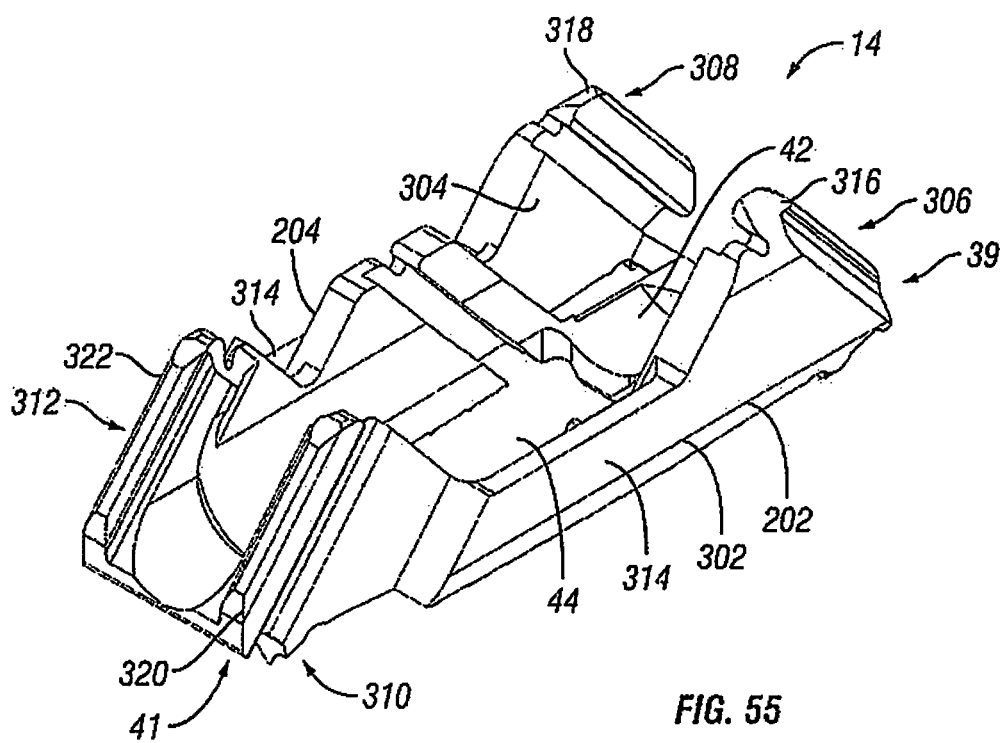
FIG. 55 is a perspective view of an endplate of the expandable fusion device of FIG. 50 in accordance with one embodiment of the present invention.

Although the following discussion relates to the first endplate 14, it should be understood that it also equally applies to the second endplate 16 as the second endplate 16 is substantially identical to the first endplate 14 in embodiments of the present invention. It should be understood that, in an embodiment, the first endplate 14 is configured to interlock with the second endplate 16. With additional reference to FIG. 55, in an exemplary embodiment, the first endplate 14 has a first end 39 and a second end 41. As illustrated, the first end 39 may be wider than the second end 41. In the illustrated embodiment, the first endplate 14 further comprises an upper surface 40 connecting the first end 39 and the second end 41, and a lower surface 42 connecting the first end 39 and the second end 41. As best seen in FIG. 54, the lower surface 42 can be curved concavely such that the first and second endplates 14, 16 form a through bore when the device 10 is in a closed position. In an embodiment, the first endplate 14 may comprise a through opening 44. The through opening 44, in an exemplary embodiment, is sized to receive bone graft or similar bone growth inducing material.

In one embodiment, the upper surface 40 of the first endplate 14 is flat and generally planar to allow the upper surface 40 of the endplate 14 to engage with the adjacent vertebral body 2. Alternatively, as shown in FIG. 15, the upper surface 40 can be curved convexly or concavely to allow for a greater or lesser degree of engagement with the adjacent vertebral body 2. It is also contemplated that the upper surface 40 can be generally planar but includes a generally straight ramped surface or a curved ramped surface. The ramped surface allows for engagement with the adjacent vertebral body 2 in a lordotic fashion. As illustrated, in an exemplary embodiment, the upper surface 40 includes texturing to aid in gripping the adjacent vertebral bodies. For example, the upper surface 40 may further comprise texturing 400 to engage the adjacent vertebral bodies. Although not limited to the following, the texturing can include teeth, ridges, friction increasing elements, keels, or gripping or purchasing projections.

In one embodiment, the first endplate 14 further comprises a first side portion 202 connecting the first end 39 and the second end 41, and a second side portion 204 connecting the first end 39 and the second end 41. In the illustrated embodiment, the first and second side portions 202, 204 are extensions from the lower surface 42. In an embodiment, the first and second side portions 202, 204 each include an interior surface 302 and an exterior surface 304. In an embodiment, the first end 39 of the first endplate 14 is generally designed and configured to fit over the second end 41 of the second endplate 16 when the device 10 is in a closed position. As illustrated, the first and second side portions 202, 204 each may include first ramped portions 306, 308, second ramped portions 310, 312, and/or central ramped portion 402.

In an embodiment, the first ramped portions 306, 308 are proximate the first end 39 of the endplate 14. In accordance with embodiment of the present invention, the first ramped portions 306, 308 of the first endplate 14 are generally designed and configured to fit over the second ramped portions 310, 312 of the second endplate 16 when the device 10 is in a closed position. In an exemplary embodiment, the first ramped portions 306, 308 generally face the first end 39 and can extend in an oblique direction with respect to the upper surface 40, for example. As illustrated, the first ramped portions 306, 308 may include tongue portions 316, 318 extending in an oblique direction with respect to the upper surface 40 of the endplate 14.

In an embodiment, the second ramped portions 310, 312 are proximate the second end 41 of the endplate 14. In an exemplary embodiment, the second ramped portions 310, 312 can extend in an oblique direction with respect to the upper surface 40 and generally face the second end 41. The first and second side portions 202, 204, in an embodiment, each can include a bridge portion 314 connecting the first ramped portions 306, 308 and the second ramped portions 310, 312. As further illustrated, the second ramped portions 310, 312 may include tongue portions 320, 322 that extend in an oblique direction with respect to the upper surface 40 of the endplate 14.

In an embodiment, the endplate 14 further may include a central ramped portion 402 proximate the bridge portion 314. In the illustrated embodiment, the endplate 14 includes a central ramped portion 402 proximate the bridge portion 314 of the second side portion 204. In an exemplary embodiment, the central ramped portion 402 can extend in an oblique direction with respect to the upper surface 40 and face the first end 39 of the endplate 14. As illustrated, the first ramped portions 306, 308 may include tongue portions 316, 318 with the tongue portions 316, 318 extending in an oblique direction with respect to the upper surface 40 of the endplate 14.

With reference to FIGS. 50-52 and 54, in an embodiment, the actuator assembly 200 includes a head portion 324, an extension 404, and a through bore 406 that extends longitudinally through the actuator assembly 200. As illustrated, the head portion 324 may include one or more instrument gripping features 330 that can allow it to be turned by a suitable instrument. In addition, the head portion 324 has a larger diameter than the other components of the actuator assembly 200 to provide a contact surface with the driving ramp 300. In the illustrated embodiment, the head portion 324 includes a rim 332 that provides a surface for contacting the driving ramp 300. In the illustrated embodiment, the extension 404 is a generally rod-like extension. In another embodiment, the extension 404 includes ratchet teeth for engaging the extension 336.

Figure 51:
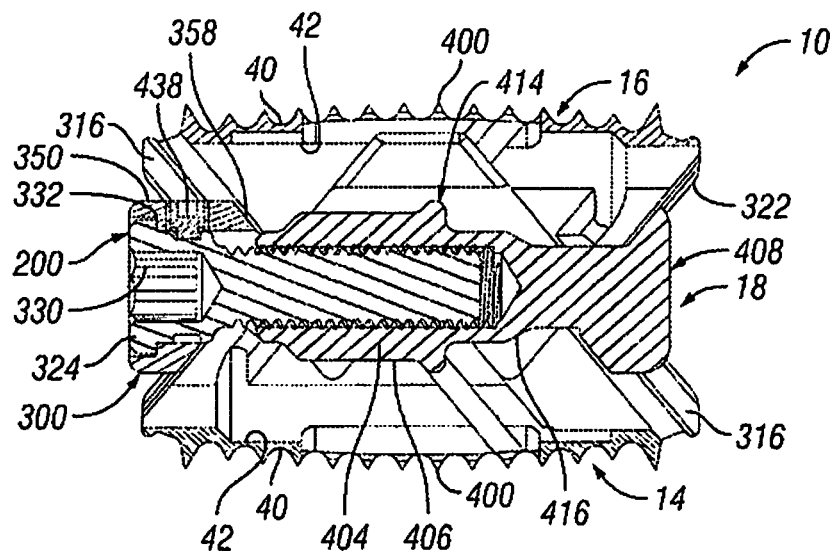
FIG. 51 is a side cross-sectional view of the expandable fusion device of FIG. 50 shown in an expanded position in accordance with one embodiment of the present invention.
Figure 52:
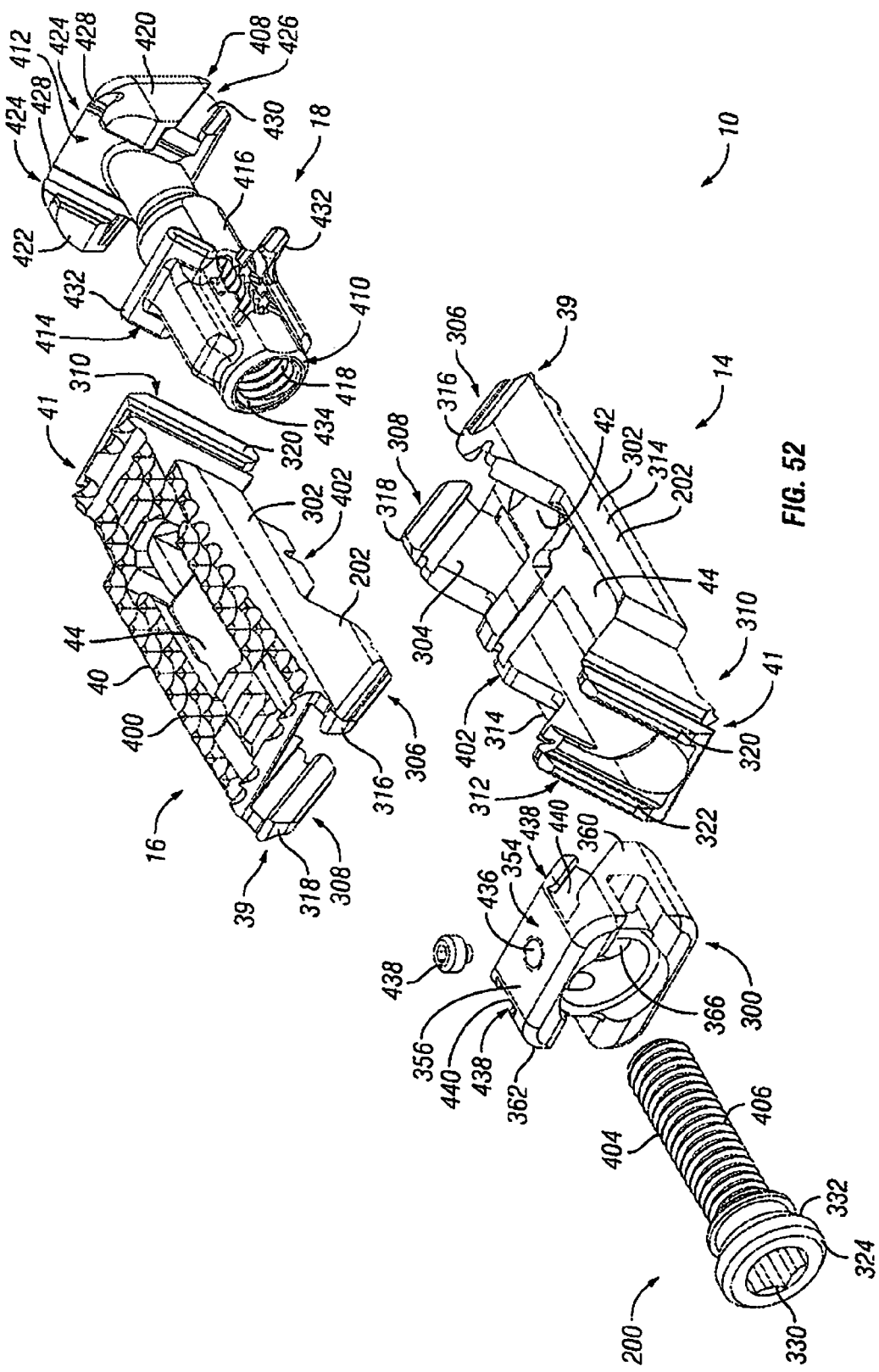
FIG. 52 is an exploded view of the expandable fusion device of FIG. 50 in accordance with one embodiment of the present invention.
Figure 53:
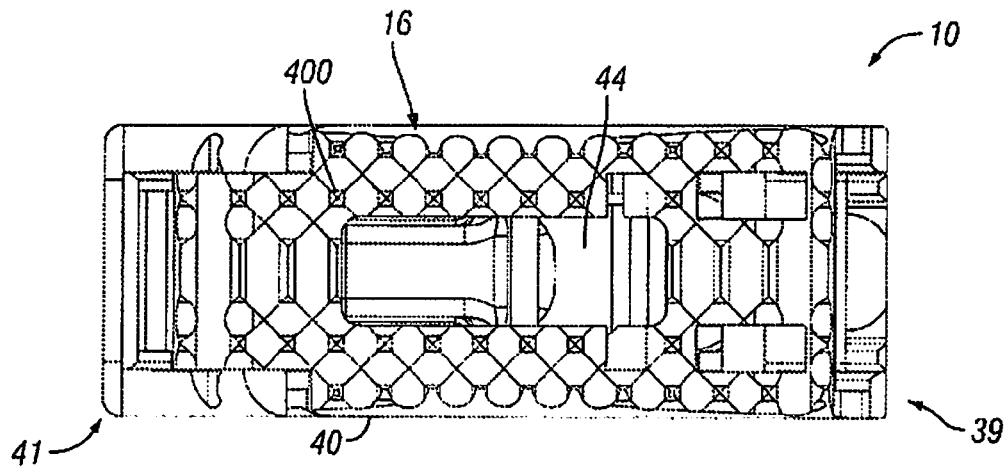
FIG. 53 is a top view of the expandable fusion device of FIG. 50 shown in an unexpanded position in accordance with one embodiment of the present invention.
Figure 56:
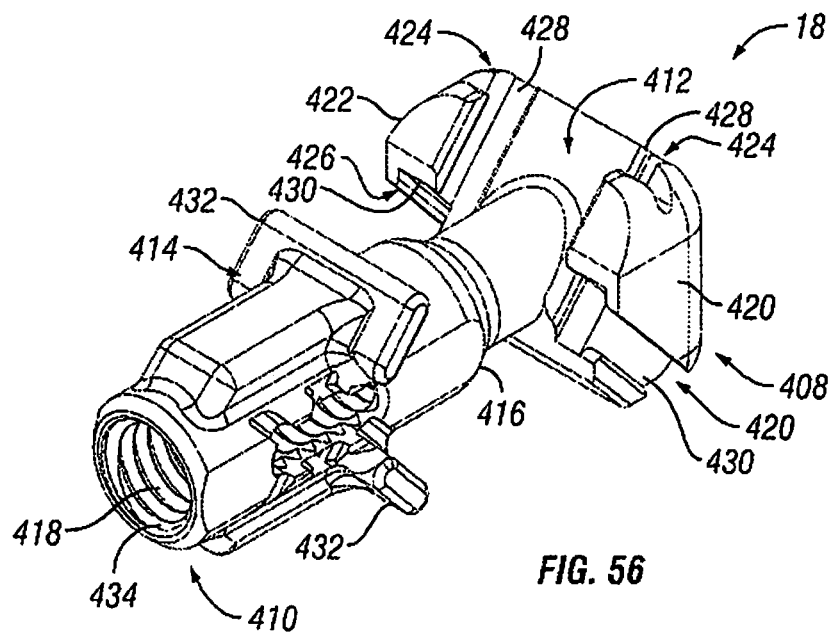
FIG. 56 is a perspective of a central ramp of the expandable fusion device of FIG. 50 in accordance with one embodiment of the present invention.
Figure 57:
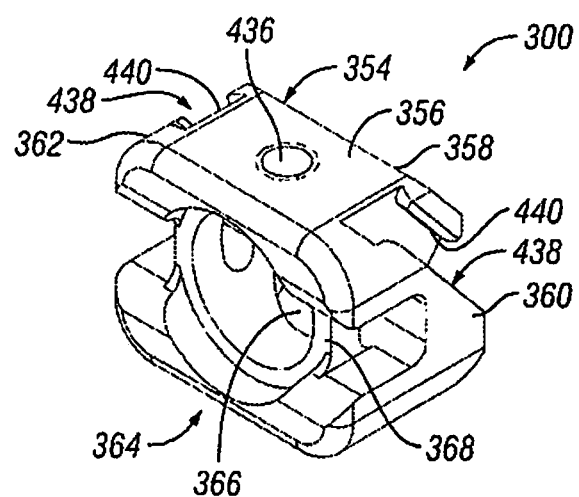
FIG. 57 is a perspective view of a driving ramp of the expandable fusion device of FIG. 50 in accordance with one embodiment of the present invention.

With reference to FIGS. 51, 52, and 56, the central ramp 18 has a first end 408 and a second end 410. In an embodiment, the central ramp 18 includes a first expansion portion 412, a second expansion portion 414, a rod-receiving extension 416, and a through bore 418 that extends longitudinally through the central ramp 18. In an exemplary embodiment, first expansion portion 412 can be proximate the first end 408 of the central ramp 18. As best seen in FIG. 56, the first expansion portion 412 may include side portions 420, 422. In an embodiment, each of the side portions 420, 422 includes dual, overlapping ramped portions that extend in oblique directions with respect to the through bore 418. For example, side portions 420, 422 each include a first ramped portion 424 that overlaps a second ramped portion 426. In the illustrated embodiment, the first ramped portion 424 faces the rod-receiving extension 416 while the second ramped portion 426 faces the opposite direction. In one embodiment, angled grooves 428, 430 are formed in each of the first and second ramped portions 424, 426. In an exemplary embodiment, the angled grooves 428, 430 are sized to receive the corresponding tongues 316, 318, 320, 322 in the first and second endplates 14, 16 with angled grooves 428 receiving tongues 320, 322 in the second endplate 16 and angled grooves 430 receiving tongues 316, 318 in the first endplate 14. Although the device 10 is described with tongues 316, 318, 320, 322 on the endplates 14, 16 and angled grooves 428, 430 on the central ramp 18, it should be understood that that device 10 can also be configured with grooves on the endplates 14, 16 and tongues on the central ramp 18, in accordance with one embodiment of the present invention.

In an embodiment, the second expansion portion 414 is located on the rod-receiving extension 416 between the first end 408 and the second end 410 of the central ramp 18. In an exemplary embodiment, the second expansion portion 414 includes central ramped portions 432. In one embodiment, the second expansion portion 414 includes two central ramped portions 432 on opposite sides of the rod-receiving extension 416. In an exemplary embodiment, the central ramped portions 424 extend in an oblique direction with respect to the through bore 418 and face the second end 410 of the central ramp 18.

The rod-receiving extension 416 extends from the first expansion portion 412 and has an opening 434 at the second end of the central ramp 18. In an embodiment, the rod-receiving extension 416 is sized and configured to receive the extension 404 of the actuator assembly 200. In an embodiment, the rod-receiving extension 416 has threading with the rod-receiving extension 416 threadingly receiving extension 404 of the actuator assembly 200. In another embodiment, the rod-receiving extension 416 has ratchet teeth with the extension 404 being ratcheted into the rod-receiving extension 416.

With reference to FIGS. 50-52 and 57, in an exemplary embodiment, the driving ramp 300 includes an upper portion 354 having an upper surface 356 and an oblique surface 358. In an embodiment, the driving ramp 300 further includes a bore 366, in an exemplary embodiment, sized to receive the extension 404 of the actuator assembly 200. In the illustrated, embodiment, the upper portion 354 has a hole 436 that extends through the upper surface 356 to the bore 366. Set screw 438 may be inserted through the hole 436 to secure the driving ramp 300 to the actuator assembly 200. In one embodiment, the driving ramp 300 further includes contact surface 368 that engages the rim 332 of the head portion 324 of the actuator assembly 200. In the illustrated embodiment, the contact surface 368 has a generally annular shape.

In an embodiment, the driving ramp 300 further includes side portions 360, 362 that extend from the upper portion 354 connecting the upper portion 354 with the lower portion 364 of the driving ramp 300. In an exemplary embodiment, the side portions 360, 362 of the driving ramp 300 each include a ramped portion 438. In the illustrated embodiment, the ramped portion 438 faces central ramp 300. In an embodiment, the ramped portion 438 is configured and dimensioned to engage the ramped portions 306, 308 at the first end 39 of the second endplate 16. In one embodiment, angled grooves 440 are formed in the ramped portions 316, 318. In an exemplary embodiment, the angled grooves 440 are sized to receive the corresponding tongues 316, 318 in the second endplate 16. Although the device 10 is described with tongues 316, 318 on the second endplate 16 and angled grooves 440 on the driving ramp 300, it should be understood that that device 10 can also be configured with grooves on the second endplate 16 and tongues on the driving ramp 300, in accordance with one embodiment of the present invention.

A method of installing the expandable fusion device 10 of FIGS. 50-57 is now discussed in accordance with one embodiment of the present invention. Prior to insertion of the fusion device, the disc space may be prepared as described above. The expandable fusion device 10 can then be inserted into and seated in the appropriate position in the intervertebral disc space. In an embodiment, the device 10 is assembled prior to insertion. The expandable fusion device 10 can be introduced into the intervertebral space, with the end having the first end 408 of the central ramp 18 being inserted. In an exemplary method, the fusion device 10 is in the unexpanded position when introduced into the intervertebral space. In an exemplary method, the intervertebral space may be distracted prior to insertion of the fusion device 10. The distraction provide some benefits by providing greater access to the surgical site making removal of the intervertebral disc easier and making scraping of the endplates of the vertebral bodies 2, 3 easier.

With the fusion device 10 inserted into and seated in the appropriate position in the intervertebral disc space, the fusion device can then expand into the expanded position. To expand the fusion device 10, an instrument is engaged with the head portion 324 of the actuator assembly 200. The instrument is used to rotate actuator assembly 200. As discussed above, actuator assembly 200 is threadingly engaged with the rod receiving extension 416 of the central ramp 18; thus, as the actuator assembly 200 is rotated in a first direction, the central ramp 18 is pulled toward the actuator assembly 200. In an exemplary embodiment, the actuator assembly 200 is moved in a linear direction with the ratchet teeth engaging as means for controlling the movement of the actuator assembly 200 and the central ramp 18.

As the central ramp space 18 is pulled towards the actuator assembly 200, the central ramp 18 acts to push endplates 14, 16 outwardly into the expanded position. By way of example, the first ramped portions 424, second ramped portions 426, and central ramped portions 432 push against the corresponding ramped portions in the first and second endplates 14, 16. The first ramped portions 424 in the first expansion portion 412 of the central ramp 18 push against the second ramped portions 310, 312 of the second endplate 16 with the corresponding tongues 320, 322 in the second ramped portions 310, 312 of the second endplate 16 riding in angled grooves 428 in the first ramped portions 424 in the first expansion portion 412. The second ramped portions 426 in the first expansion portion 412 push against the first ramped portions 316, 318 of the first endplate 14 with the corresponding tongues 316, 318 in first ramped portions 316, 318 of the first endplate 14 riding in angled grooves 430 in the second ramped portions 426 in the first expansion portion 412. The central ramped portions 432 in the second expansion portion 414 push against the central ramped portion 402 in the first and second endplates 14, 16.

As discussed above, the actuator assembly 200 also engages driving ramp 300; thus, as the actuator assembly 200 is rotated in a first direction, the actuator assembly 200 pushes the driving ramp 300 towards the central ramp 18 in a linear direction. As the driving ramp 300 is pushed towards the central ramp 18, the driving ramp 300 also acts to push the endplates 14, 16 outwardly into the expanded position. By way of example, the ramped portions 438 of the driving ramp 300 push against ramped portions 306, 308 at the first end 39 of the second endplate 16. As the endplates 14, 16 move outwardly, the tongues 316, 318 in the ramped portions 306, 308 of the second endplate 16 ride in the angled grooves 440 in the ramped portions 438 of the driving ramp 300.

It should also be noted that the expansion of the endplates 14, 16 can be varied based on the differences in the dimensions of the various ramped portions in the central ramp 18, the driving ramp 300, and the first and second endplates 14, 16. As best seen in FIG. 16, the endplates 14, 16 can be expanded in any of the following ways: straight rise expansion, straight rise expansion followed by a toggle into a lordotic expanded configuration, or a phase off straight rise into a lordotic expanded configuration.

In the event the fusion device 10 needs to be repositioned or revised after being installed and expanded, the fusion device 10 can be contracted back to the unexpanded configuration, repositioned, and expanded again once the desired positioning is achieved. To contract the fusion device 10, the instrument can be used to rotate the actuator assembly 200 in a second direction that is opposite the first direction. Rotation of the actuator assembly 200 results in movement of the central ramp 18 and the driving ramp 300 away from one another. As the central ramp 18 and the driving ramp 300 move, the endplates 14, 16 move inwardly into the unexpanded position.

Although the preceding discussion only discussed having a single fusion device 10 in the intervertebral space, it is contemplated that more than one fusion device 10 can be inserted in the intervertebral space. It is further contemplated that each fusion device 10 does not have to be finally installed in the fully expanded state. Rather, depending on the location of the fusion device 10 in the intervertebral disc space, the height of the fusion device 10 may vary from unexpanded to fully expanded. It should be noted that, as well as the height being varied from an unexpanded state to an expanded state, the fusion 10 may be positioned permanently anywhere between the expanded state and the unexpanded state.

Referring now to FIGS. 58-65, an alternative embodiment of the expandable fusion device 10 is shown. In the illustrated embodiment, the fusion device 10 includes an upper endplate 480, a lower endplate 485, and actuator assembly 445. The actuator assembly 445 comprises a front sloped height actuator 450, a rear sloped height actuator 455, and a linear actuator 460. In an embodiment the linear actuator 460 functions to pull the front sloped actuator 450 and the rear sloped actuator 455 together, which forces apart the upper endplate 480 and lower endplate 485.

Figure 58:
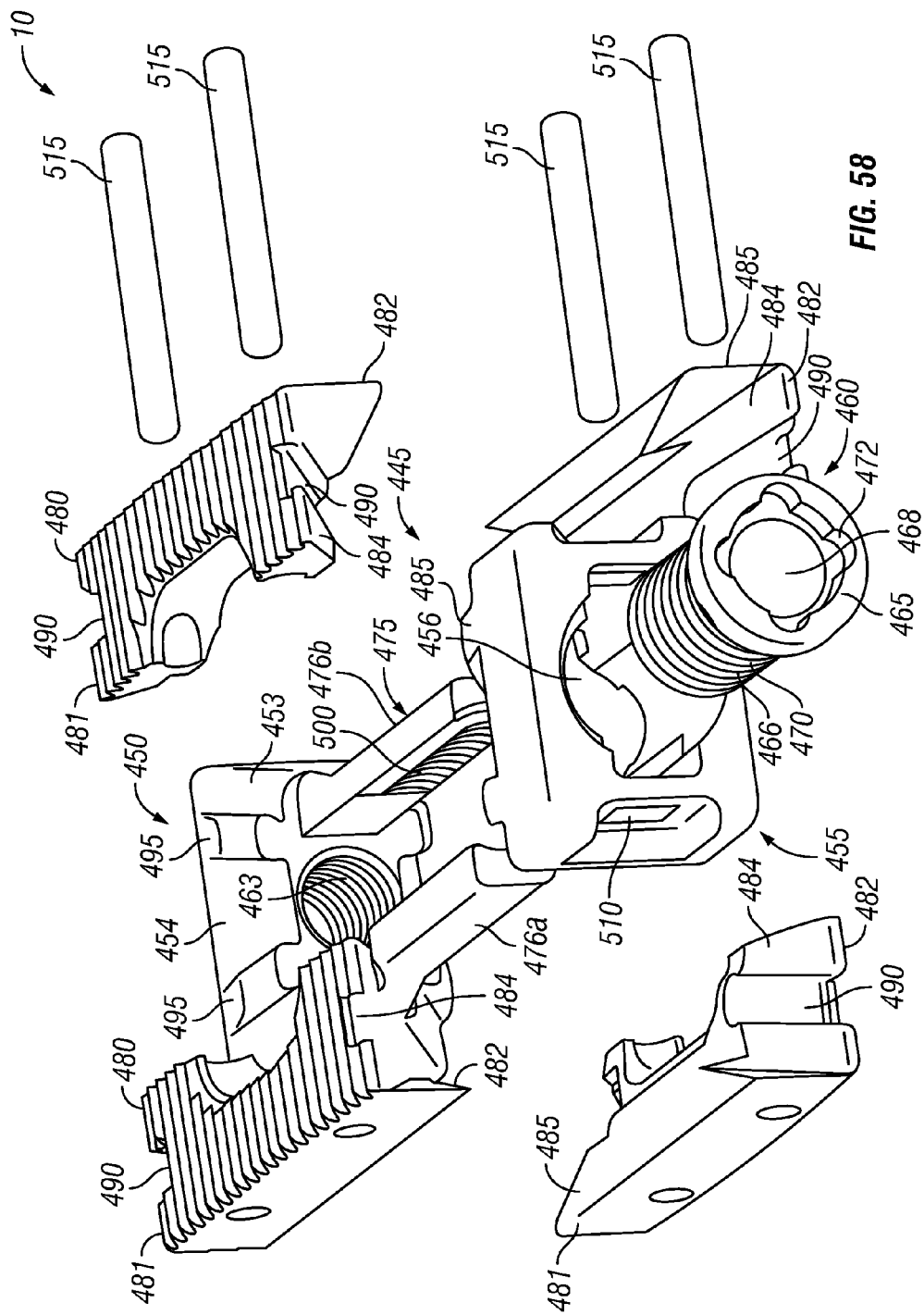
FIG. 58 is a rear perspective view of an exploded expandable fusion device in accordance with one alternative embodiment.
Figure 59:
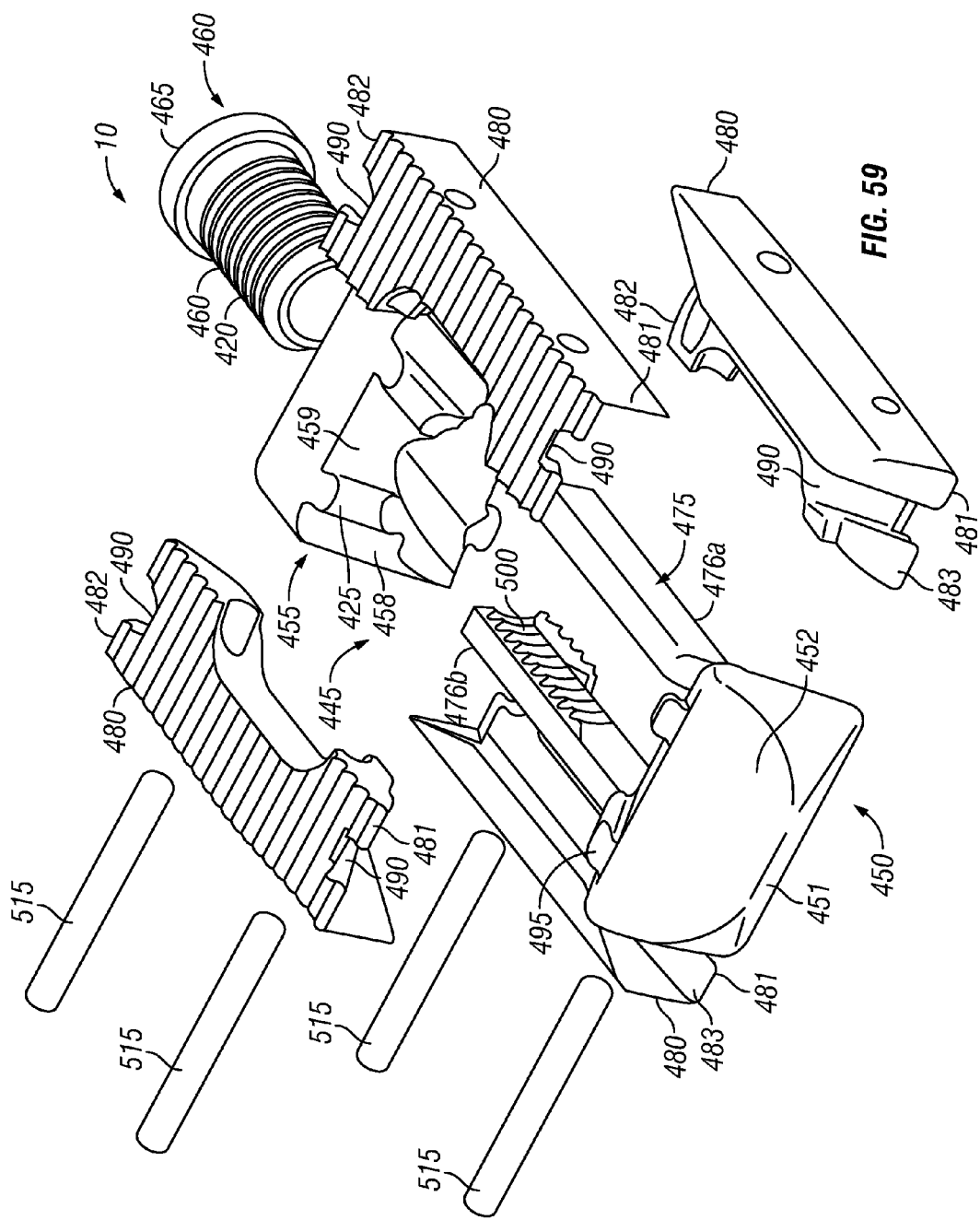
FIG. 59 is a front perspective view of an exploded expandable fusion device in accordance with one alternative embodiment.

With reference to FIGS. 58-59, in an exemplary embodiment of fusion device 10, the actuator assembly 445 comprises a front sloped actuator 450, a rear sloped actuator 455, and a linear actuator 460. As illustrated, the linear actuator 460 may comprise a head portion 465 and an extension 466. In an embodiment, the extension 466 is a generally rod-like extension that comprises surface threads 470. It should be understood that, while the surface threads 470 of the linear actuator 460 are referred to as threaded, the surface threads 470 may only be partially threaded in accordance with one embodiment. The linear actuator 460 of the actuator assembly 445 may extend through an opening 456 in the rear sloped actuator 455 where the surface threads 470 of the linear actuator 460 engage the complimentary threads 500 of the extension 475 of the front sloped actuator 450. Thus, as the linear actuator 460 is rotated in a first direction, the actuator assembly 445 pulls the front sloped actuator 450 towards the rear sloped actuator 455 and consequently also towards the head portion 465 of the linear actuator 460 in a linear direction. As the front sloped actuator 450 is pulled towards the rear sloped actuator 455, the sloped surfaces 454, 459 respectively, of the front sloped actuator 450 and the rear sloped 455 actuator push the upper 480 and lower 485 endplates outwardly into the expanded position.

Figure 63:
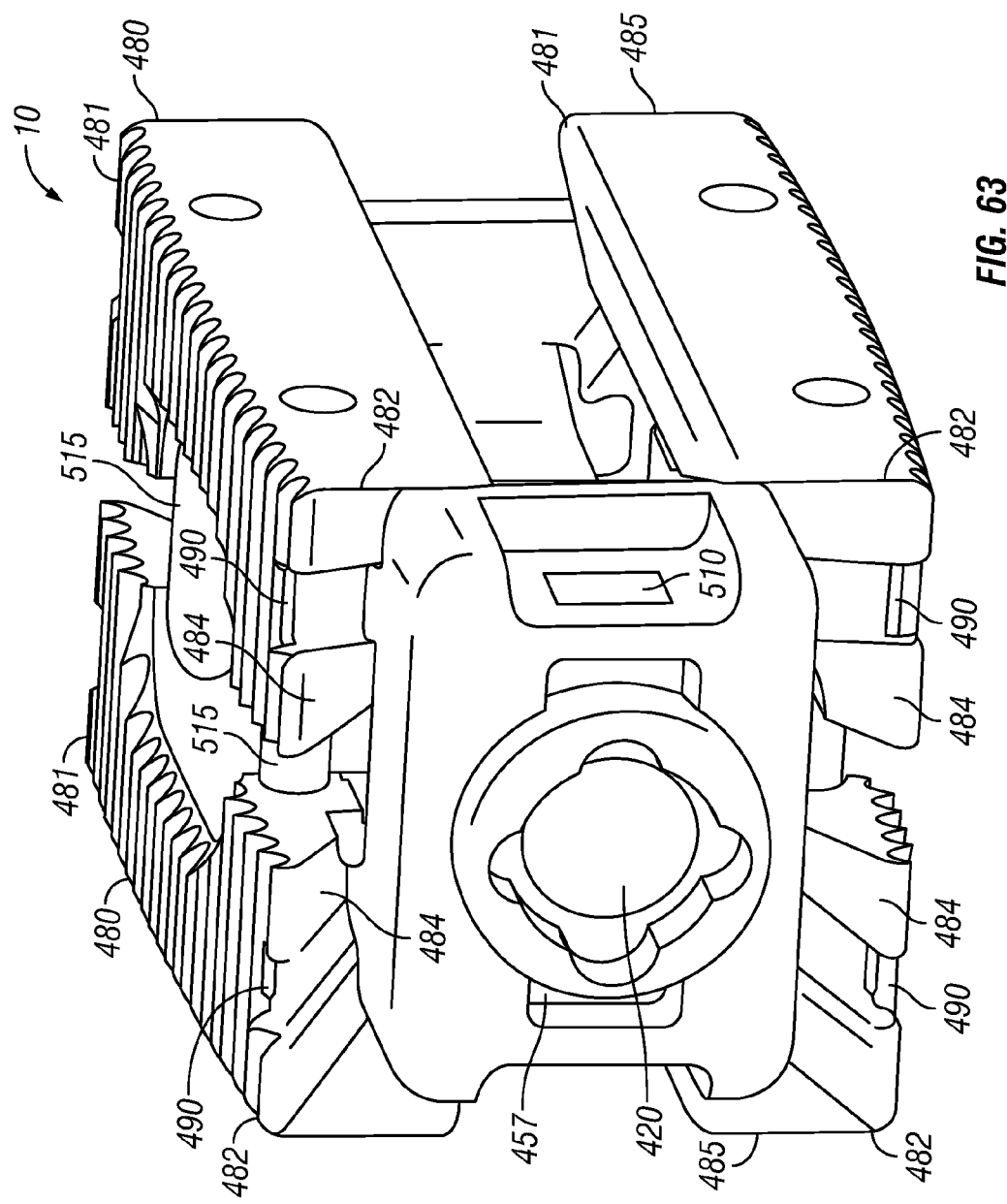
FIG. 63 is a rear perspective view of the expandable fusion device in the expanded position in accordance with one alternative embodiment.

With reference to FIGS. 58-59 and 63, in an exemplary embodiment, the upper and lower endplates 480, 485 may comprise two portions, such as two opposing mirrored halves. Both the upper endplate 480 and lower endplate 485 may comprise a front end 481 and a rear end 482. The front and rear ends 481, 482 of each portion of each endplate may be substantially similar to the front and rear ends 481, 482 of every other portion of every other endplate. It should be understood that that references to the front and rear ends 481, 482 of each endplate are with respect to the front and rear of the expandable fusion device 10, which is with respect to the direction of placement into an intervertebral disc space with the front of the expandable fusion device 10 placed into the space first, followed by the rear of the expandable fusion device 10. Each portion of the upper and lower endplates 480, 485 further may comprise front ramped surface 483 and rear ramped surface 484, as a component of the front and rear ends 481, 482 of each portion of the upper and lower endplate 480, 485. The front ramped surface 483 may be located on the front end 481 of each half of the upper and lower endplates 480, 485. The rear ramped surface 484 may be located on the rear end 482 of each half of the upper and lower endplates 485. With additional reference to FIGS. 60 and 61, in the illustrated embodiment, the front and rear ends 481, 482 of each portion of upper and lower endplates 480, 485 contains a slot 490 that engages the corresponding elevated and angled tongues 495 of the front sloped actuator 450 and the rear sloped actuator 455. The elevated and angled tongues 495 may be substantially identical in design and function for both the front sloped actuator 450 and the rear sloped actuator 455. Because the elevated and angled tongues 495 are angled at a slant that directs away from the center of the expandable fusion device, as the front sloped actuator 450 is pulled towards the rear sloped actuator 455 by rotation of the linear actuator 460, the ramped sections 454, 459 of the front and rear sloped actuators 450, 455, in conjunction with the elevated and angled tongues 495 of the front and rear sloped actuators 450, 455 pushes both portions of the upper and lower endplates 480, 485 outward simultaneously in both horizontal and vertical directions.

With reference to FIGS. 58-62, front sloped actuator 450 may comprise a front end 451 and a rear end 453. The front end 451 may comprise opposing sloped surfaces 452. In some embodiments, the front end 451 of the front sloped actuator 450 is the section of the expandable fusion device 10 that is first inserted into an intervertebral disc space. The front sloped actuator 450 may also comprise a rear end 453 connected to extension 475 from the front slope actuator 450. The rear end 453 of the front sloped actuator 450 also may comprise opposing sloped surfaces 454. The opposing sloped surfaces 454 of the rear end 453 of the front sloped actuator 450 may be sloped towards the rear sloped actuator 455. The opposing sloped surfaces 454 of the rear end 453 of the front sloped actuator 450 also comprises the elevated and angled tongues 495 that engage the slots 490 of the halves of the upper and lower endplates 480, 485, as described in the preceding paragraph. The front sloped actuator 450 also comprises a threaded screw opening 463. As illustrated, the extension 475 from the front sloped actuator 450 may comprise extending threaded prongs 476a, 476b. The extension 475 is generally located in the center of the actuator assembly 445, and with respect to the front end 451 of the front sloped actuator 450, the extension 475 extends longitudinally towards the rear sloped actuator 455 and the linear actuator 460. The extension 475 may be sized and configured to receive the extension 466 of the linear actuator 460. The extension 475 may comprise threads 500 that engage with the threads 470 of the extension 466 of the linear actuator 460. Turning the linear actuator 460, rotates the threads 470 of the linear actuator 460, which are threadingly engaged to the threads 500 of the extension 475 of the front sloped actuator 450, and consequently can push or pull the extension 475 and therefore the front sloped actuator 450 towards or away from the rear sloped actuator 455 and the linear actuator 460, dependent upon which direction the linear actuator 460 is rotated.

Figure 60:
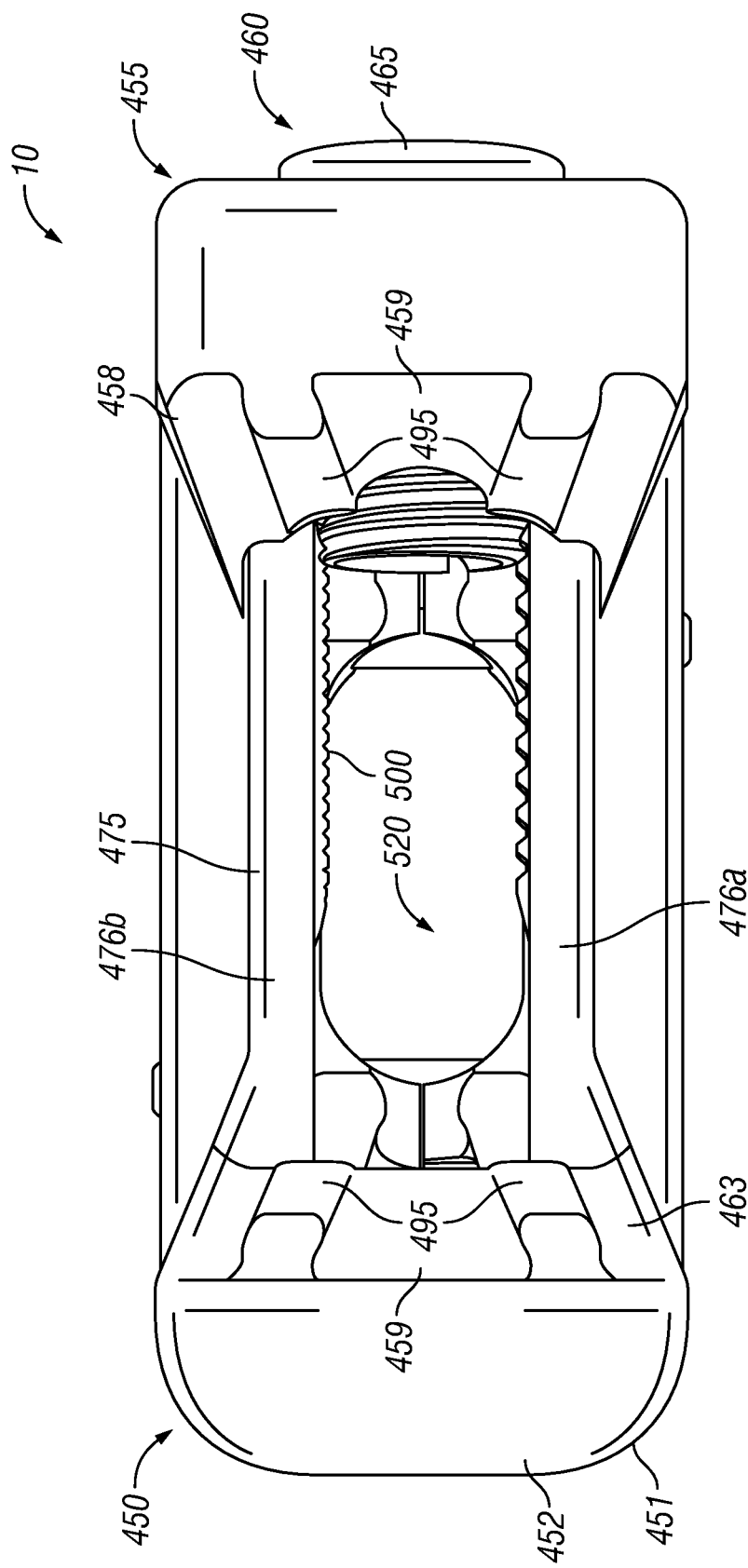
FIG. 60 is a top-down view of the expandable fusion device that lacks the top endplate, providing an interior view of the unexpanded expandable fusion device, in accordance with one embodiment of the present invention.
Figure 61:
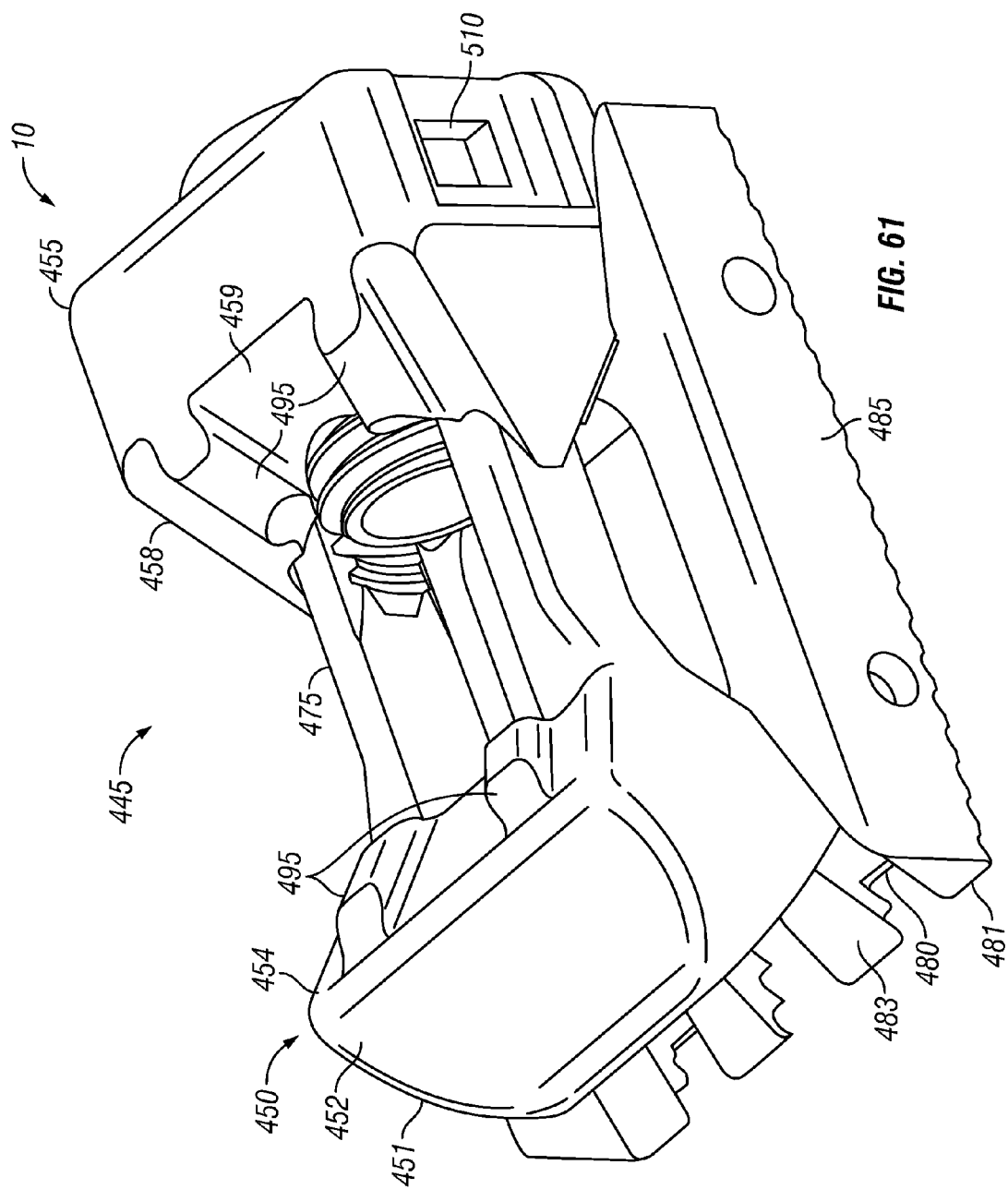
FIG. 61 is a perspective view showing placement of the tool engagement service of the expandable fusion device of FIG. 60 in accordance with one embodiment of the present invention.

With continued reference to FIGS. 58-62, rear sloped actuator 455 may comprise an opening 456. The opening 456 may be disposed in the center of the rear sloped actuator 455 and may run longitudinally throughout the entirety of the rear sloped actuator 455. The opening 456 may be sized to receive the extension of the 475 of the front sloped actuator 450 with the extension 466 of the linear actuator 460 disposed therein. The rear sloped actuator 455 also contains a front side 458 which faces the extension 475 of the front sloped actuator 450. The front side 458 of the rear sloped actuator 455 has opposing sloped surfaces 459, that are sloped towards the extension 475 and consequently the front sloped actuator 450. The front side 458 of the rear sloped actuator 455 also comprises the elevated and angled tongues 495 that engage the slots 490 of the halves of the upper 480 and lower 485 endplates, as described above. As best seen in FIGS. 61 and 63, in an exemplary embodiment, the rear sloped actuator 455 comprises tool engagement surfaces 510. Tool engagement surface 510 is a surface for engagement of a placement and positioning tool (not shown) which allows for insertion and adjustment of the fusion device 10 into an intervertebral space as best shown in FIG. 1. Tool engagement surfaces 510 may be located horizontally on opposing sides of sloped rear actuator 455.

As discussed above, the linear actuator 460 may comprise a head portion 465 and an extension 466. Surface threads 470 may be disposed on the extension 466 of the linear actuator 460. Surface threads 470 are complimentary to and engage the threads 500 of the extension 475 of the front sloped actuator 450. In another embodiment, the extension 466 includes ratchet teeth for engaging the front sloped actuator 450. Linear actuator 460 also comprises opening 468 in the head portion 465 of linear actuator 460. In the illustrated embodiment, the opening 468 includes one or more instrument gripping features 472 that can allow it to be turned by a suitable instrument. Linear actuator 460 may disposed in the opening 456 of the rear sloped actuator 455 with the extension 466 running through the opening 456. The head portion 465 may be of a diameter that is too large to pass through the opening 456 and thus allows the linear actuator 460 to reach an endpoint where it, or from another perspective the front sloped actuator 450, cannot be drawn closer through rotation of the linear actuator 460.

Figure 62:
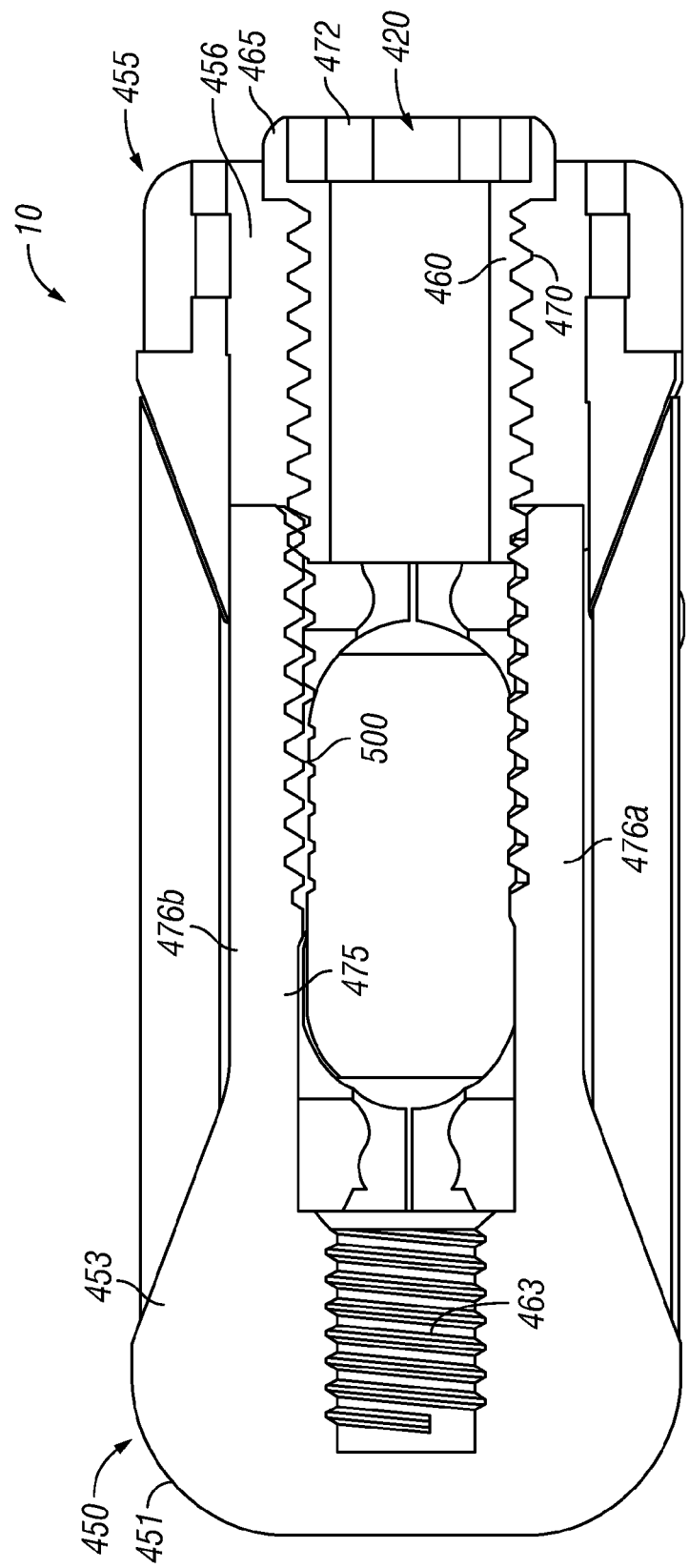
FIG. 62 is a top-down cross sectional view of an expandable fusion device shown in the unexpanded position in accordance with one embodiment of the present invention.

As best seen in FIGS. 60-62, in an exemplary embodiment, the front sloped actuator 450 comprises an extension 475 further comprising threads 500 that engage the surface threads 470 of the linear actuator 460. Thus, as the linear actuator 460 is rotated in a first direction by a threaded instrument (not shown), the front sloped actuator 450 moves toward the flanged end 465 of the linear actuator 460. In the event the fusion device 10 needs to be repositioned or revised after being installed and expanded, the fusion device 10 can be contracted back to the unexpanded configuration, repositioned, and expanded again once the desired positioning is achieved. To contract the fusion device 10, the thread locking screw 460 can be rotated in a second direction. As discussed above, actuator assembly 445 is in threaded engagement with the extension 475 of the front sloped actuator 450; thus, as linear actuator 460 is rotated in a second direction, opposite the first direction, the front sloped actuator 450 moves with respect to the actuator assembly 445 and the upper and lower endplates 480, 485 away from the flanged end 465.

Figure 64A:
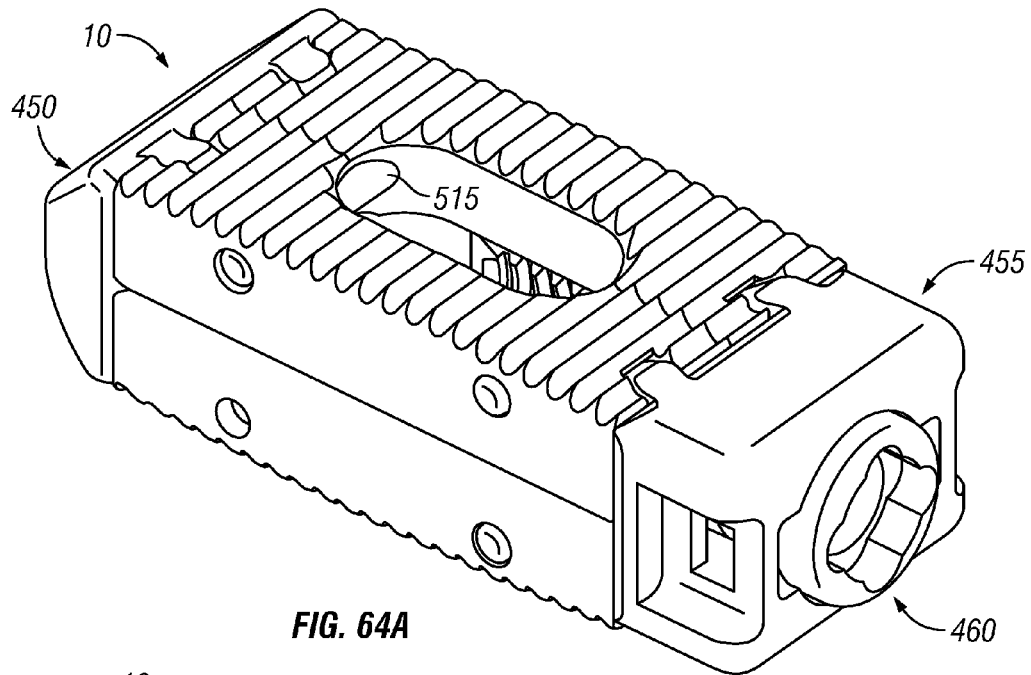
FIG. 64(a) is an angled side perspective view of the expandable fusion device in the unexpanded position in accordance with one alternative embodiment.
Figure 64B:
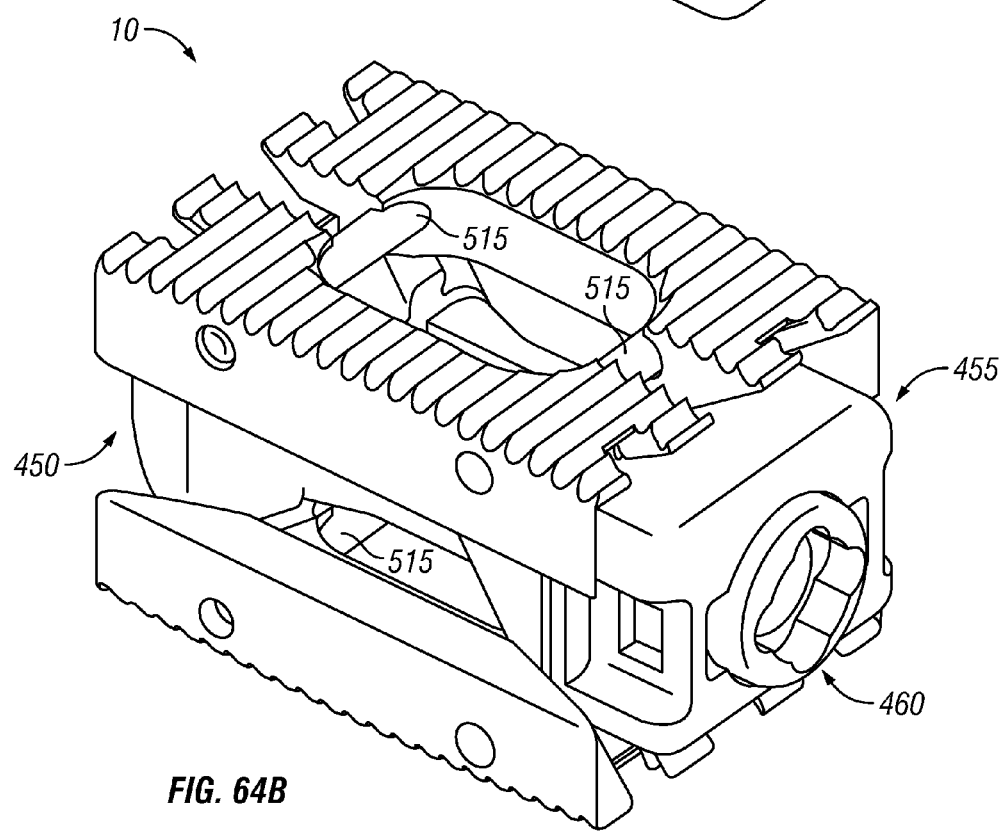
FIG. 64(b) is an angled side perspective view of the expandable fusion device in the expanded position in accordance with one alternative embodiment.

With reference to FIGS. 58-59, and 63, in an exemplary embodiment the upper and lower endplates 480, 485 may further comprise endplate pins 515. As illustrated, the upper and lower endplates 480, 485 may each comprise two endplate pins 515. Endplate pins 515 may rest in slots disposed in each portion of the upper and lower endplates 480, 485. In the illustrated embodiment, the endplate pins 515 connect the portions of the upper endplate 480 and the portions of the lower endplate 485. Endplate pins 515 can provide for even and simultaneous movement of endplate portions. With specific reference to FIGS. 64(*a*) and 64(*b*), endplate pins 515 can be seen in both the unexpanded fusion device configuration as shown in FIG. 64(*a*) and the expanded fusion device configuration as shown in FIG. 64(*b*).

Figure 65:
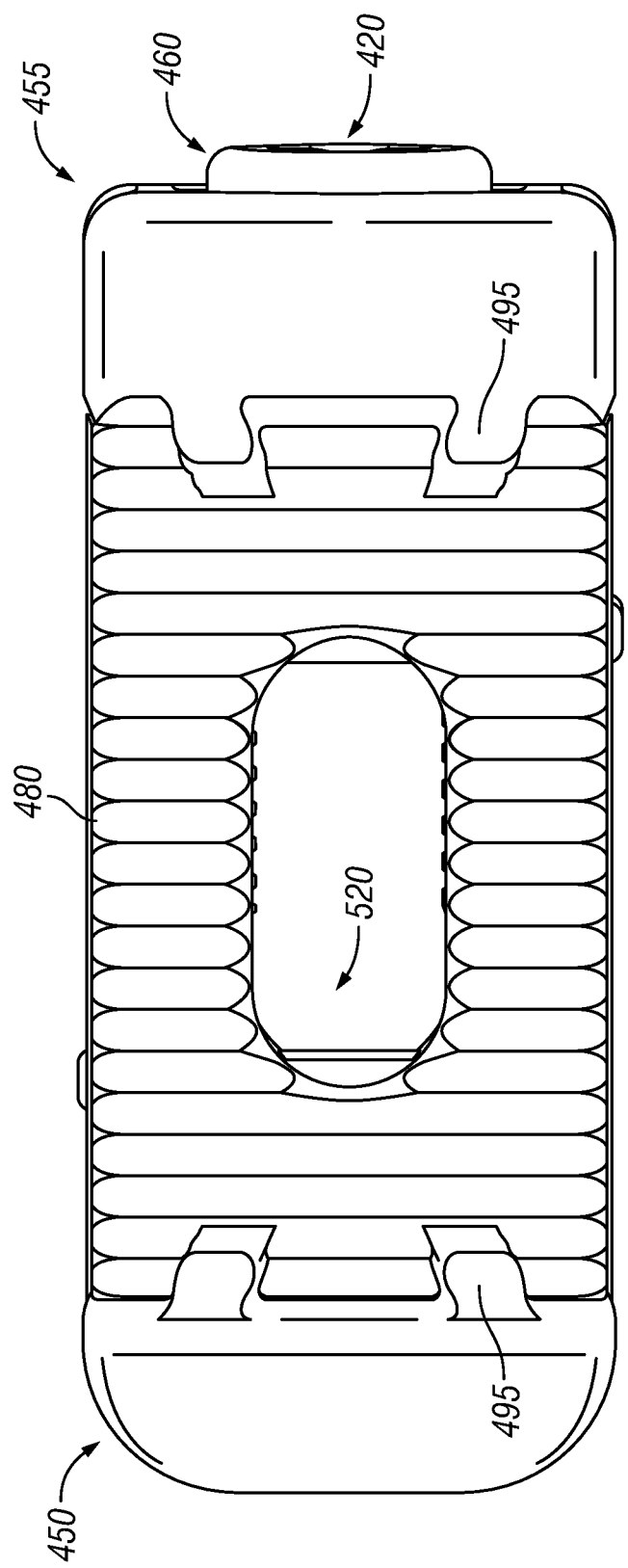
FIG. 65 is a top-down perspective view of the expandable fusion device in the unexpanded position in accordance with one alternative embodiment.

In an exemplary embodiment, FIG. 65 depicts bone graft hole 520, which is shown disposed in upper endplate 480. Bone graft hole 520 in conjunction with threaded hole 470 of the linear actuator 460 provides space for bone grafts that may be used in the intervertebral fusion procedure.

A method of installing the expandable fusion device 10 of FIGS. 58-65 is now discussed in accordance with one embodiment of the present invention. Prior to insertion of the fusion device 10, the disc space may be prepared as described above. The expandable fusion device 10 can then be inserted into and seated in the appropriate position in the intervertebral disc space. In an embodiment, the device 10 is assembled prior to insertion. The expandable fusion device 10 can be introduced into the intervertebral space, with the end having the first end of the front sloped actuator 450 being inserted. In an exemplary method, the fusion device 10 is in the unexpanded position when introduced into the intervertebral space. In an exemplary method, the intervertebral space may be distracted prior to insertion of the fusion device 10. The distraction provide some benefits by providing greater access to the surgical site making removal of the intervertebral disc easier and making scraping of the endplates of the vertebral bodies 2, 3 easier as depicted in FIG. 1.

With the fusion device 10 inserted into and seated in the appropriate position in the intervertebral disc space, the fusion device 10 can then expand into the expanded position. To expand fusion device 10, an instrument may be engaged with the instrument gripping features 472 the linear actuator 460. The threaded instrument may rotate the linear actuator 460 in the first direction, drawing the front sloped actuator 450 and the rear sloped actuator 455 together and contracting the actuator assembly 455. In an exemplary embodiment the front sloped actuator 450 and the linear actuator 460 may be drawn together in a linear fashion with the threads 500 of the extension 475 of the front sloped actuator 450 engaging the surface threads 470 of the linear actuator 460 as a means for controlling the movement of the contraction of the actuator assembly 445 and consequently the expansion of the upper and lower endplates 480, 485, which expand horizontally and vertically with contraction of the actuator assembly 445.

It should also be noted that the expansion of the upper and lower endplates 480, 485 may be varied based on the differences in the dimensions of the sloped surfaces 454 and 459 and the direction of the angle in the elevated and angled tongues 495. As best seen in FIG. 16, the upper and lower endplates 480 and 485 can be expanded in any of the following ways: straight rise expansion, straight rise expansion followed by a toggle into a lordotic expanded configuration, or a phase off straight rise into a lordotic expanded configuration.

Although the preceding discussion only discussed having a single fusion device 10 in the intervertebral space, it is contemplated that more than one fusion device 10 can be inserted in the intervertebral space. It is further contemplated that each fusion device 10 does not have to be finally installed in the fully expanded state. Rather, depending on the location of the fusion device 10 in the intervertebral disc space, the height of the fusion device 10 may vary from unexpanded to fully expanded. It should be noted that, as well as the height being varied from an unexpanded state to an expanded state, the fusion 10 may be positioned permanently anywhere between the expanded state and the unexpanded state.

Referring now to FIGS. 66-73, an alternative embodiment of the expandable fusion device 10 is shown. In the illustrated embodiment, the fusion device 10 includes an upper endplate 570, a lower endplate 580, and a collective actuator assembly 520. The collective actuator assembly 520 comprises a front sloped actuator assembly 530, a rear sloped actuator assembly 540, and threaded locking screws 550. In an embodiment a threaded instrument 560 functions to pull the front sloped actuator assembly 530 and the rear sloped actuator assembly 540 together, which forces apart the upper endplate 570 and lower endplate 580.

With reference to FIGS. 66-68 and 71, in an exemplary embodiment of fusion device 10, the collective actuator assembly 520 comprises a front sloped actuator assembly 530, a rear sloped actuator assembly 540, and threaded locking screws 550. The threaded locking screws 550 have flanged ends 551 and surface threads 552 that extend at least partially through the collective actuator assembly 520. It should be understood that, while the surface threads 552 of the threaded locking screws 550 are referred to as threaded, the surface threads 552 may only be partially threaded in accordance with one embodiment. The threaded locking screws 550 of the collective actuator assembly 520 may rest in an opening 541 in the rear width actuator 542 of the rear sloped actuator assembly 540 where the surface threads 552 of the threaded locking screws 550 engage threaded screw openings 595 of the front height actuator 532 of the front sloped actuator assembly 530. The threaded instrument 560 (FIG. 72) may extend through an instrument opening 561 in the rear width actuator 542 of the rear sloped actuator assembly 540. As the threaded instrument 560 is rotated in a first direction, the collective actuator assembly 520 pulls the front sloped actuator assembly 530 towards the rear sloped actuator assembly 540 and consequently also towards the flanged ends 551 of the threaded locking screws 550 in a linear direction. As the front sloped actuator assembly 530 is pulled towards the rear sloped actuator assembly 540, the front width actuator 536 and the rear width actuator 542 are pulled together. As they are pulled together, the front and rear width actuators 536, 542 drive apart the portions of the upper endplate 570 and the portions of the lower endplate 575. More particularly, the front and rear width actuators 536 542 engage the front height actuators 532 and the rear height actuators 546 to force them horizontally outward, which in turn engage the upper and lower endplates 570, 575 to force them horizontally outward. The front stop pins 533 may have one end disposed in the retaining bores 534 of the front height actuator 532 and opposite ends disposed in the front stop pint track 535 of the front width actuator 536. The front stop pins 533 may slide in the front stop pin track 535 of the front width actuator 536 until they reach the end of the front stop pin track 535 and movement of the front width actuator 536 is stopped, thus restricting lateral expansion of the device 10, as best seen on FIG. 68. Simultaneously, the rear stop pins 543 disposed in the retaining bores 544 of the rear width actuator 542, slide in the rear stop pin tracks 545 of the rear height actuators 546 until they reach the end of the rear stop pin tracks 545 and movement of the rear width actuator 542 is stopped, as best seen on FIGS. 68 and 71. When the front width actuator 536 is stopped, the front sloped actuator assembly 530 may be pulled towards the rear sloped actuator assembly 540, by simultaneously turning threaded locking screws 550. As threaded locking screws 550 are rotated simultaneously in a first direction, the sloped surfaces 537, 547 respectively, of the front height actuators 532 and the rear height actuator 546 push the upper 570 and lower 580 endplates vertically outward into the expanded position.

Figure 66:
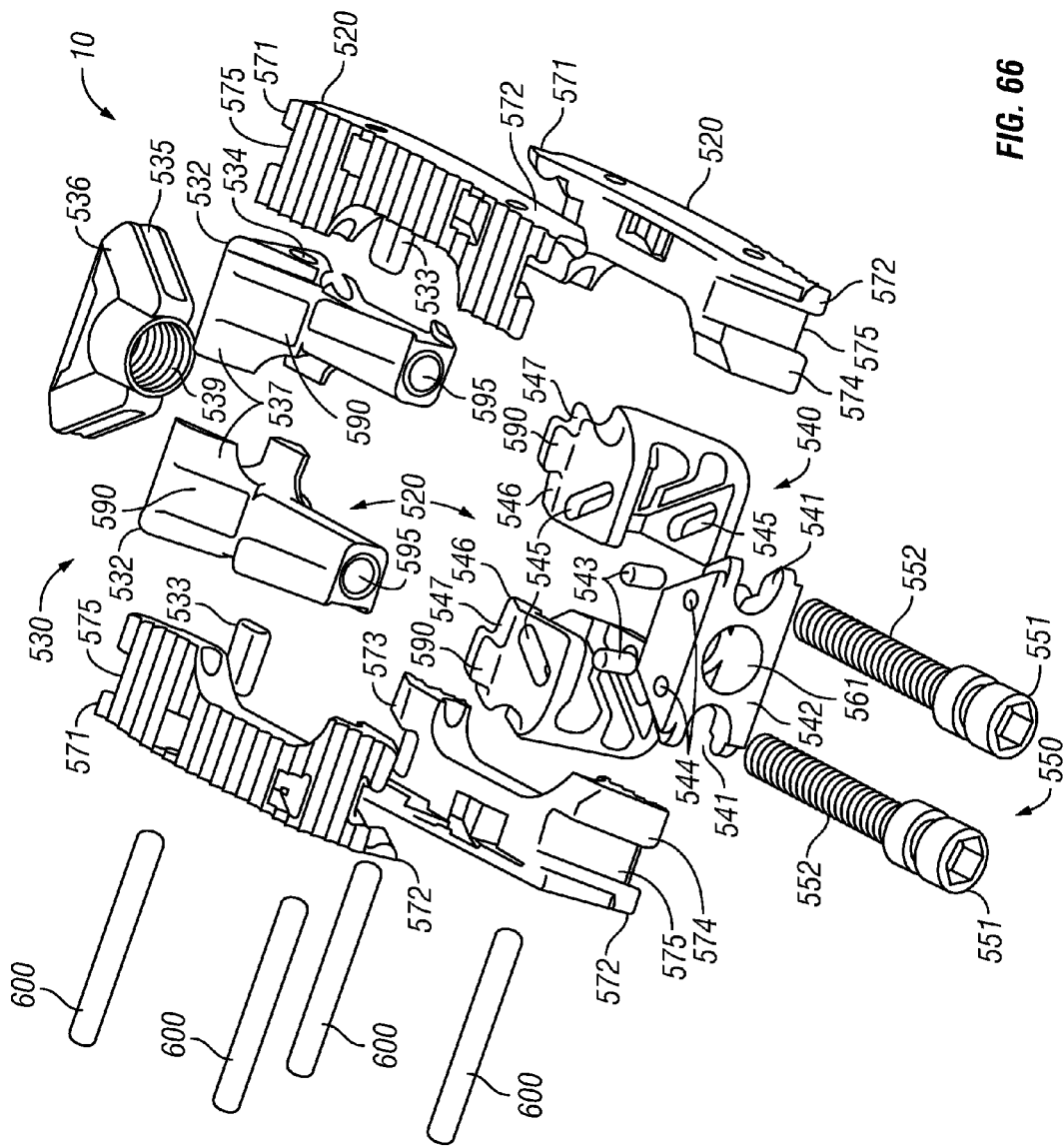
FIG. 66 is a rear perspective view of an exploded expandable fusion device in accordance with one alternative embodiment.
Figure 67:
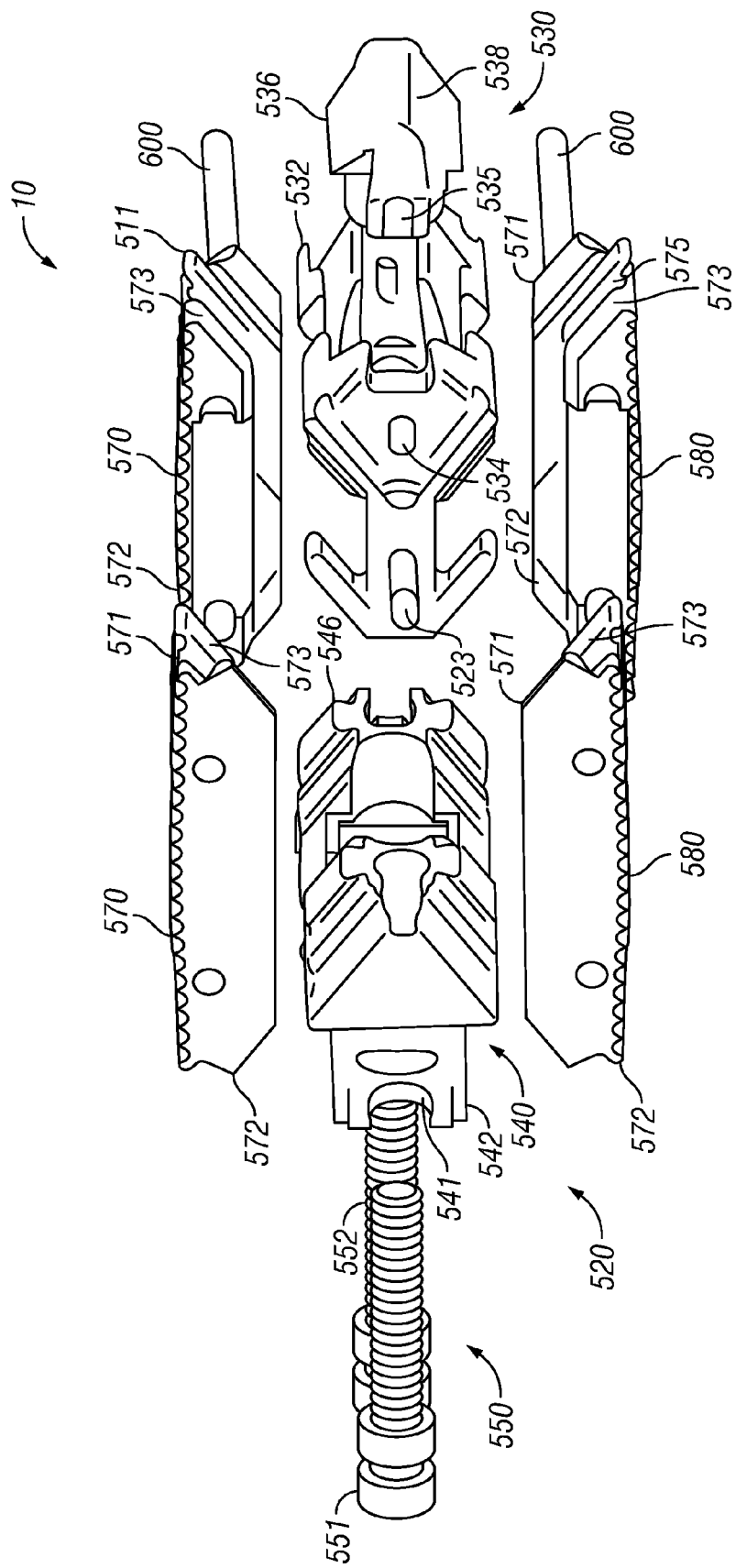
FIG. 67 is side view of an exploded expandable fusion device in accordance with one embodiment of the present invention.
Figure 68:
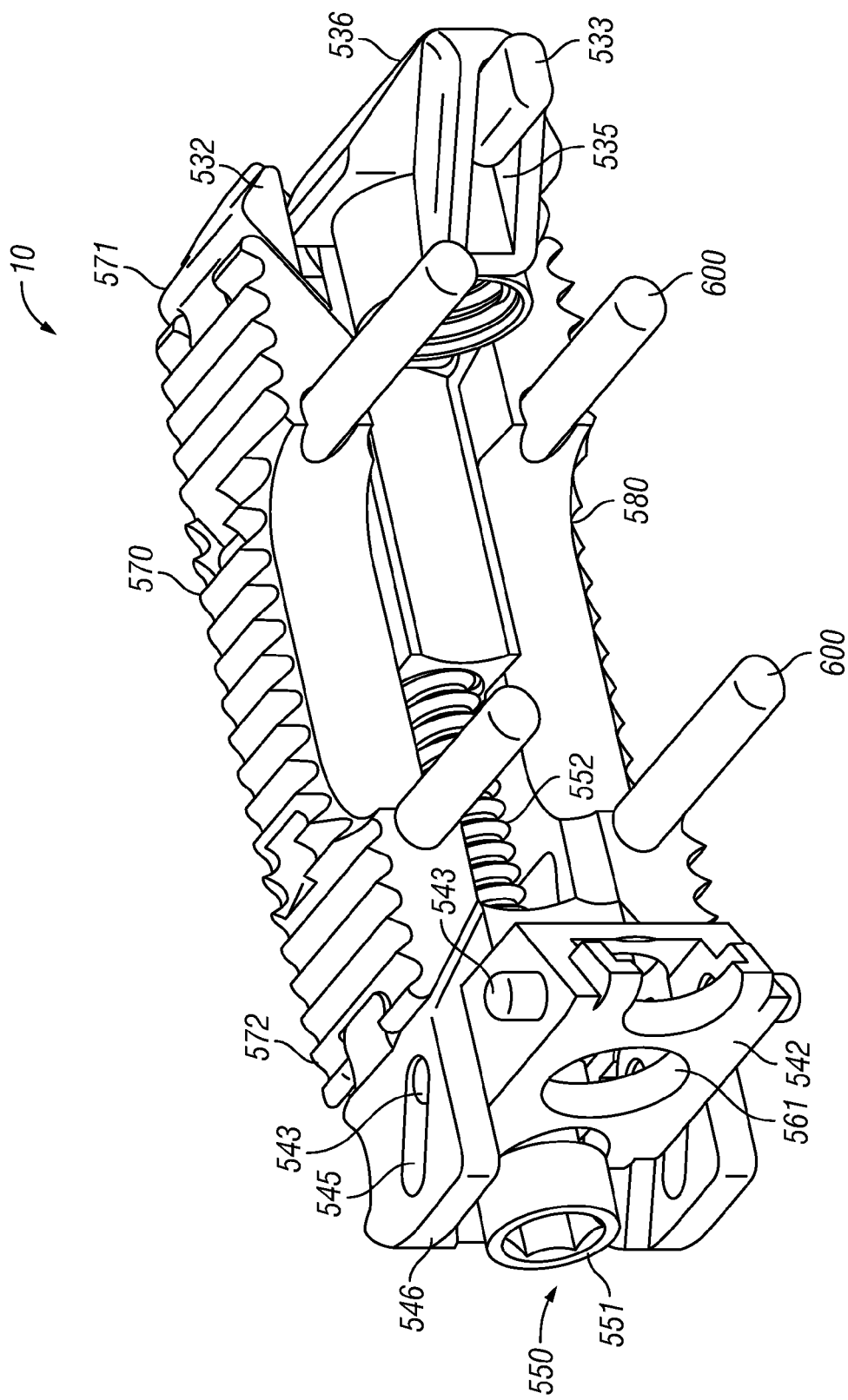
FIG. 68 is a side cross-sectional view that lacks one front height actuator and one rear height actuator as well as one half of the upper and lower endplates, in order to show the interior of the expandable fusion device of FIG. 66 in accordance with one embodiment of the present invention.

With reference to FIGS. 66-68, in an exemplary embodiment, the upper and lower endplates 570, 580 may split into two portions, such as being bifurcated into two opposing mirrored halves. The portions of the upper endplate 570 maybe substantially identical to the portions of the lower endplate 580 in embodiments of the present invention. Both the upper and lower endplates 570, 580 may comprise front and rear ends 571, 572. The front and rear ends 571, 572 of each portion of each endplate may be substantially similar to the front and rear ends 571, 572 of every other portion of every other endplate. It should be understood that that references to the front and rear ends 571, 572 of each endplate are with respect to the front and rear of the expandable fusion device 10, which is with respect to the direction of placement into an intervertebral disc space with the front of the expandable fusion device 10 placed into the space first, followed by the rear of the expandable fusion device 10. Each portion of the upper and lower endplates 570, 580 further comprises front and rear ramped surface portions 573, 574, as a component of the front and rear ends 571, 572 of each portion of the upper and lower endplate 570, 580 respectively. The front ramp surface 573 is located on the front end 571 of each portion of the upper and lower endplates 570, 580. The rear ramp surface 574 is located on the rear end 572 of each portion of the upper and lower endplates 570, 580. The front and rear ends 571, 572 of each half of upper endplate 570 contains a slot 575 that engages the corresponding elevated tongues 590 of the front height actuator 532 and the rear height actuator 546 of the front sloped actuator assembly 530 and the rear sloped actuator assembly 540 respectively. The elevated tongues 590 may be substantially identical in design and function for both the front height actuator 532 and the rear height actuator 546.

Figure 69:
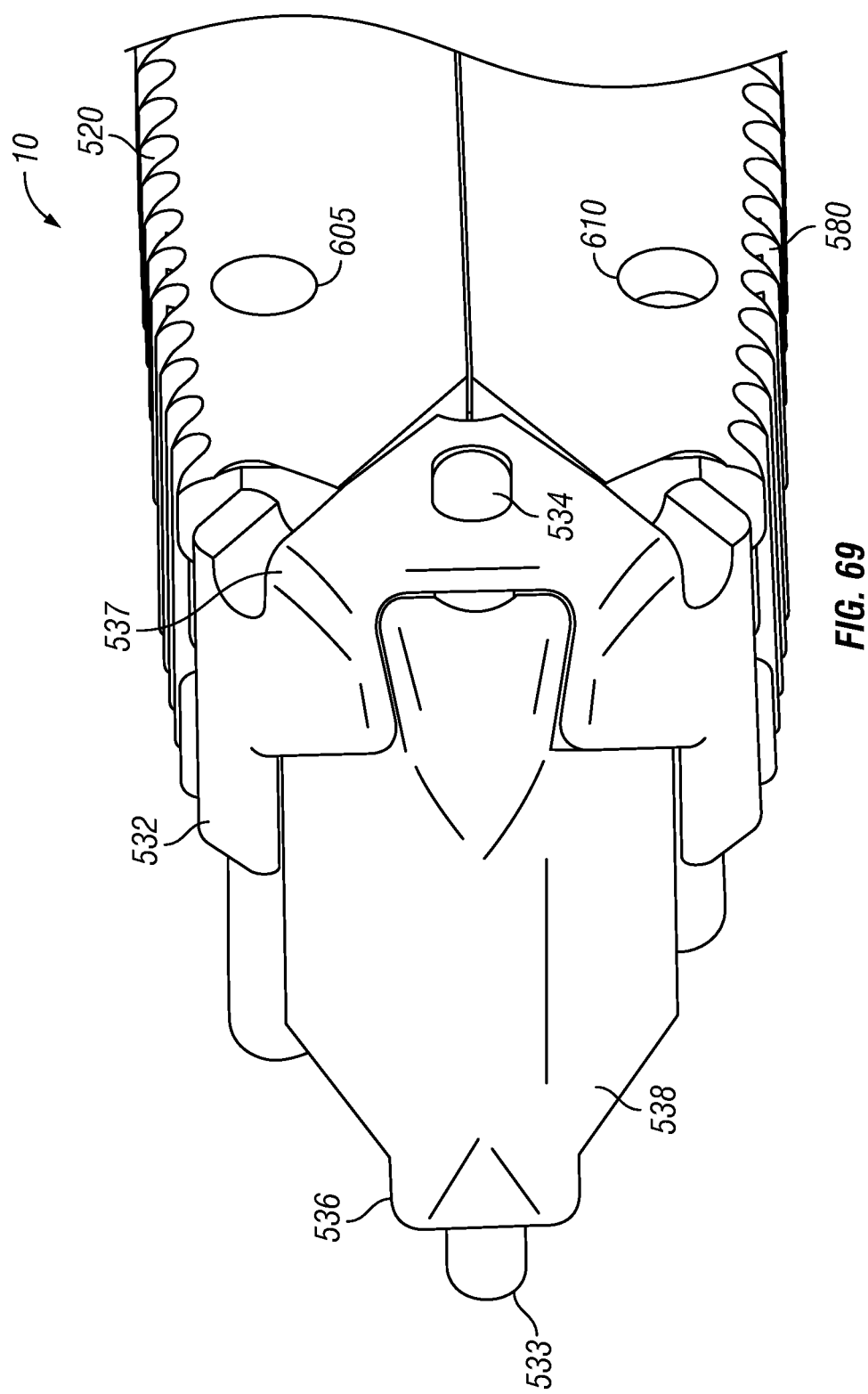
FIG. 69 is a front perspective view of an expandable fusion device shown in the unexpanded position in accordance with one embodiment of the present invention.
Figure 70:
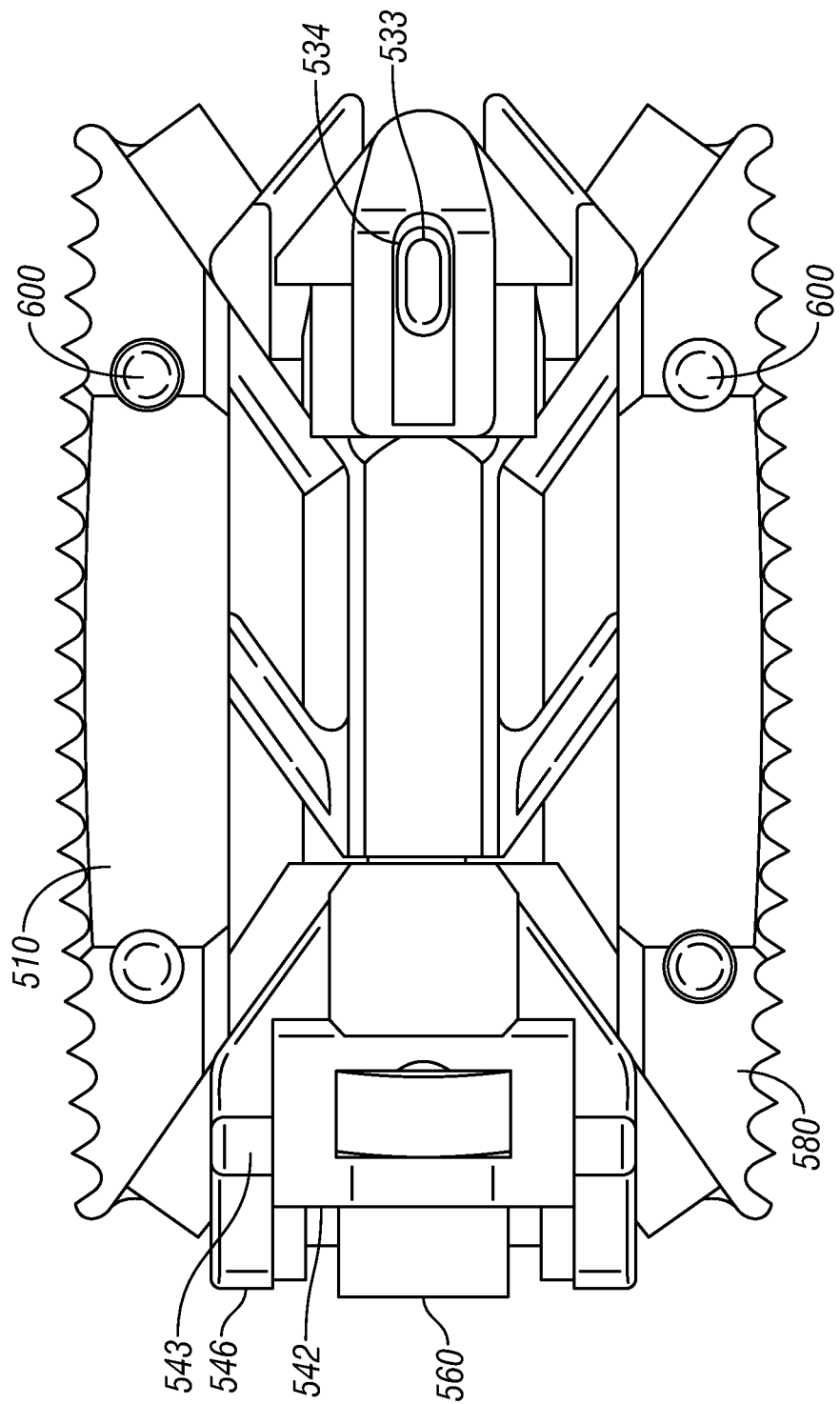
FIG. 70 is a side cross-sectional view of the expandable fusion device in the expanded position in accordance with one alternative embodiment.

As best seen in FIGS. 66-67 and 69, the front sloped actuator assembly 530 may comprise a front width actuator 536. As illustrated, the front width actuator 536 may be wedge-shaped. The front width actuator 536 may further comprise a sloped front end 538. The sloped front end 538 may be the section of the expandable fusion device 10 that is first inserted into an intervertebral disc space. The front width actuator 536 may further comprise a front stop pin track 535 that is complimentary to the front stop pins 533. The front width actuator 536 may also comprise a threaded instrument opening 539. The threaded instrument opening 539 also comprises threads that engage the threaded instrument 560. The front sloped actuator assembly 530 may also comprise a pair of front height actuators 532. The front height actuators 532 may be mirrored analogues that have substantially the same function. The front width actuator 536 may be disposed between the pair of front height actuators 532. The front height actuators 532 comprise a sloped surface 537 and elevated tongues 590 that vertically expand the upper 570 and lower 580 endplates. The front height actuators 532 additionally comprise a threaded screw opening 595. The threaded screw opening 595 engages the threaded locking screws 550. When threaded locking screws 550 are turned in the a first direction, upper 570 and lower 580 endplates are expanded vertically, due to the contraction of the front sloped actuator assembly 530 and the rear sloped actuator assembly 540. Front height actuators 532 may additionally comprise retaining bores 534, wherein the front stop pins 533 are disposed.

Rear sloped actuator assembly 540 may comprise a rear width actuator 542. As illustrated, the rear width actuator 542 may be generally wedge-shaped. The rear width actuator 542 may further comprise an instrument opening 561 wherein the threaded instrument 560 may be inserted to operate the expandable fusion device 10. The rear width actuator 542 may additionally comprise openings 541. Threaded locking screws 550 may be inserted into openings 541 of the rear width actuator 542 and run through the collective actuator assembly 520 to connect to the threaded screw openings 595 in the front height actuators 532. Rear width actuator 542 may additionally comprise retaining bores 544 which house the rear stop pins 543. The rear stop pins 543 are fixed in the retaining bores 544 and do not move relative to and apart from the retaining bores 544. The rear stop pins 543 and retaining bores 544 may be present in pairs, located on the top and bottom of the rear width actuator 542. Rear stop pins 543 connect the rear width actuator 542 to the rear height actuators 546. Rear height actuators 546 comprise rear stop pin tracks 545 in which the rear stop pins 543 may be disposed. When the threaded instrument 560 is turned in a first direction to contract the collective actuator assembly 520 and draw the front sloped actuator assembly 530 and the rear sloped actuator 540, the rear stop pins 543 slide in the rear stop pin tracks 545 to expand the upper and lower endplates 570, 580 horizontally, until the rear stop pins 543 contact the end of the rear stop pin tracks 545. The rear sloped actuator assembly 540 may also comprise a pair of rear height actuators 546. The rear height actuators 546 may be mirrored analogues that have substantially the same function. The rear width actuator 542 may be disposed between the pair of rear height actuators 546. Rear height actuators 546 may comprise a sloped surface 547 and elevated tongues 590 that vertically expand the upper 570 and lower 580 endplates. Sloped surface 547 is sloped towards the front sloped actuator assembly 530. Elevated tongues 590 engage the corresponding slots 575 of the upper 570 and lower 580 endplates.

As discussed above, the threaded locking screws 550 of the collective actuator assembly 520, may each comprise a flanged end 551 and surface threads 552. Surface threads 551 are disposed on the front end 553 of the threaded locking screws. The front end 553 of the threaded locking screws 550 are longitudinally opposite the flanged ends 551 of the threaded locking screws 550. Surface threads 551 are complimentary to and engage the threads of the threaded screw openings 595 of the front height actuators 532 of the front sloped actuator assembly 530. Threaded locking screws 550 also comprise an instrument opening 554 in the flanged ends 551 of the threaded locking screws 550. In an exemplary embodiment, the instrument opening 554 is configured and dimensioned to receive a locking screw instrument (not shown). Threaded locking screws 550 are disposed in the threaded screw openings 541 of the rear width actuator 542 with the front end 553 running through the threaded screw openings 541. The flanged ends 551 may be of a diameter that is too large to pass through the threaded screw openings 541 and thus allows the threaded locking screws 550 to reach an endpoint where it, or from another perspective the front sloped actuator assembly 530, cannot be drawn closer through rotation of the threaded locking screws 550.

As best seen in FIG. 68, as the threaded locking screws 550 are rotated in a first direction by a locking screw instrument (not shown), the front height actuators 532 are pulled towards the flanged ends 551 of the threaded locking screws 550. In the event the fusion device 10 needs to be repositioned or revised after being installed and expanded, the upper 570 and lower 580 endplates of fusion device 10 can be contracted back to the unexpanded configuration, repositioned, and expanded again once the desired positioning is achieved. To contract the endplates 570,580 of fusion device 10, the threaded instrument 560 and the threaded locking screws 550 can be rotated in a second direction. As discussed above, rear sloped actuator assembly 540 is in threaded engagement with the front sloped actuator assembly 530; thus, as the threaded instrument 560 is rotated in a second direction, opposite the first direction, the front sloped actuator assembly 530 is pushed away from the rear sloped actuator assembly 540 and the upper 570 and lower 580 endplates are pulled inward horizontally, this may continue until the front stop pins 533 and the rear stop pins 543 reach the end of their collective stop pin tracks 535 and 545 respectively. When the upper 570 and lower 580 endplates have been contracted to their initial unexpanded horizontal positions, the threaded locking screws 550 can be turned in a second direction opposite the first direction. Rotating the threaded locking screws 550 in a second direction will continue to push the front sloped actuator assembly 530 away from the rear sloped actuator assembly 540. This can continue, until the endplates 570,580 are fully contracted into the default unexpanded configuration.

With reference to FIGS. 66-68, in an exemplary embodiment the upper and lower endplates 570, 580 each comprise endplate pins 600. As illustrated, the upper and lower endplates 570, 580 each comprise two endplate pins 600. Endplate pins 600 rest in slots disposed in each half of the upper and lower endplates 605, 610. Endplate pins 600 connect the halves of the upper endplate 470 and the halves of the lower endplate 580. Endplate pins 600 provide for even and simultaneous movement of endplate halves.

Figure 71A:
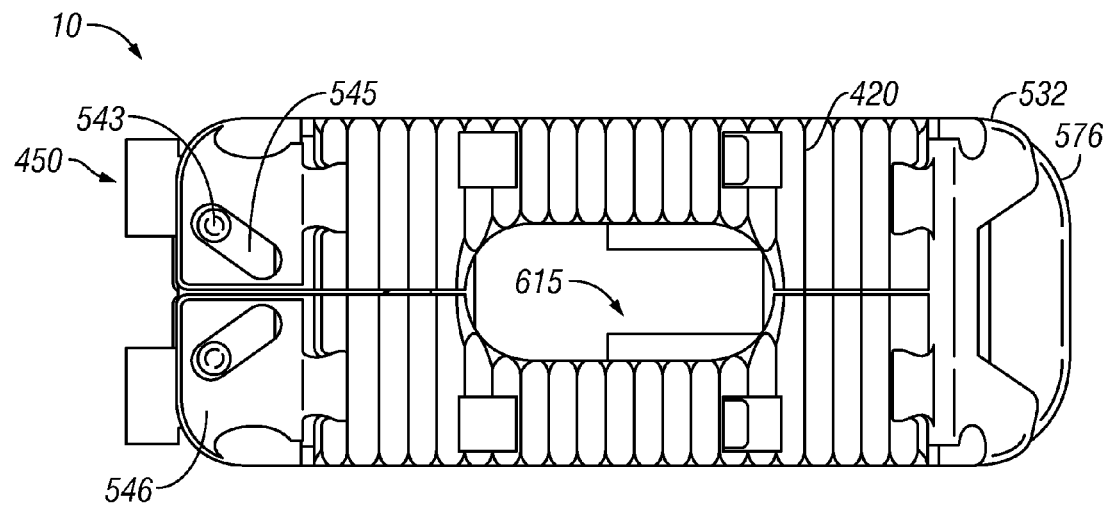
FIG. 71(a) is top-down view of the expandable fusion device in the unexpanded position in accordance with one alternative embodiment.
Figure 71B:
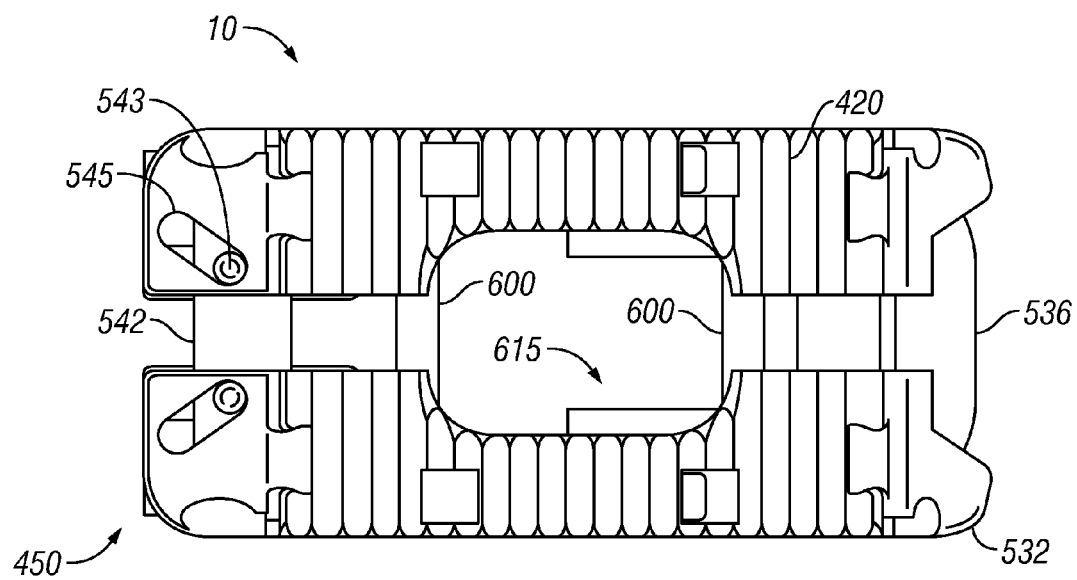
FIG. 71(b) is top-down view of the expandable fusion device in the expanded position in accordance with one alternative embodiment.
Figure 72:
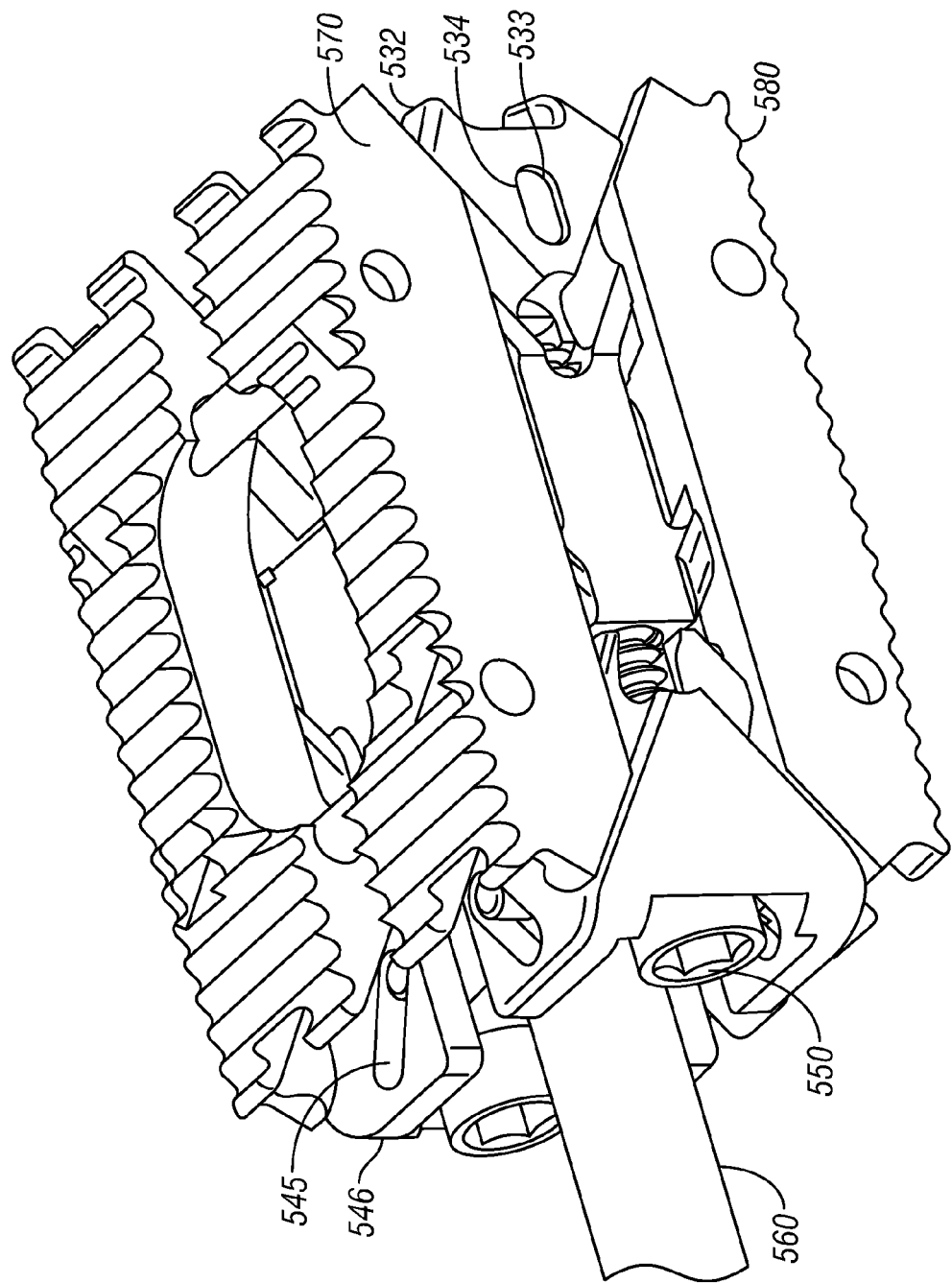
FIG. 72 is a view of the expandable fusion device with threaded instrument inserted and in the expanded position in accordance with one alternative embodiment.
Figure 73:
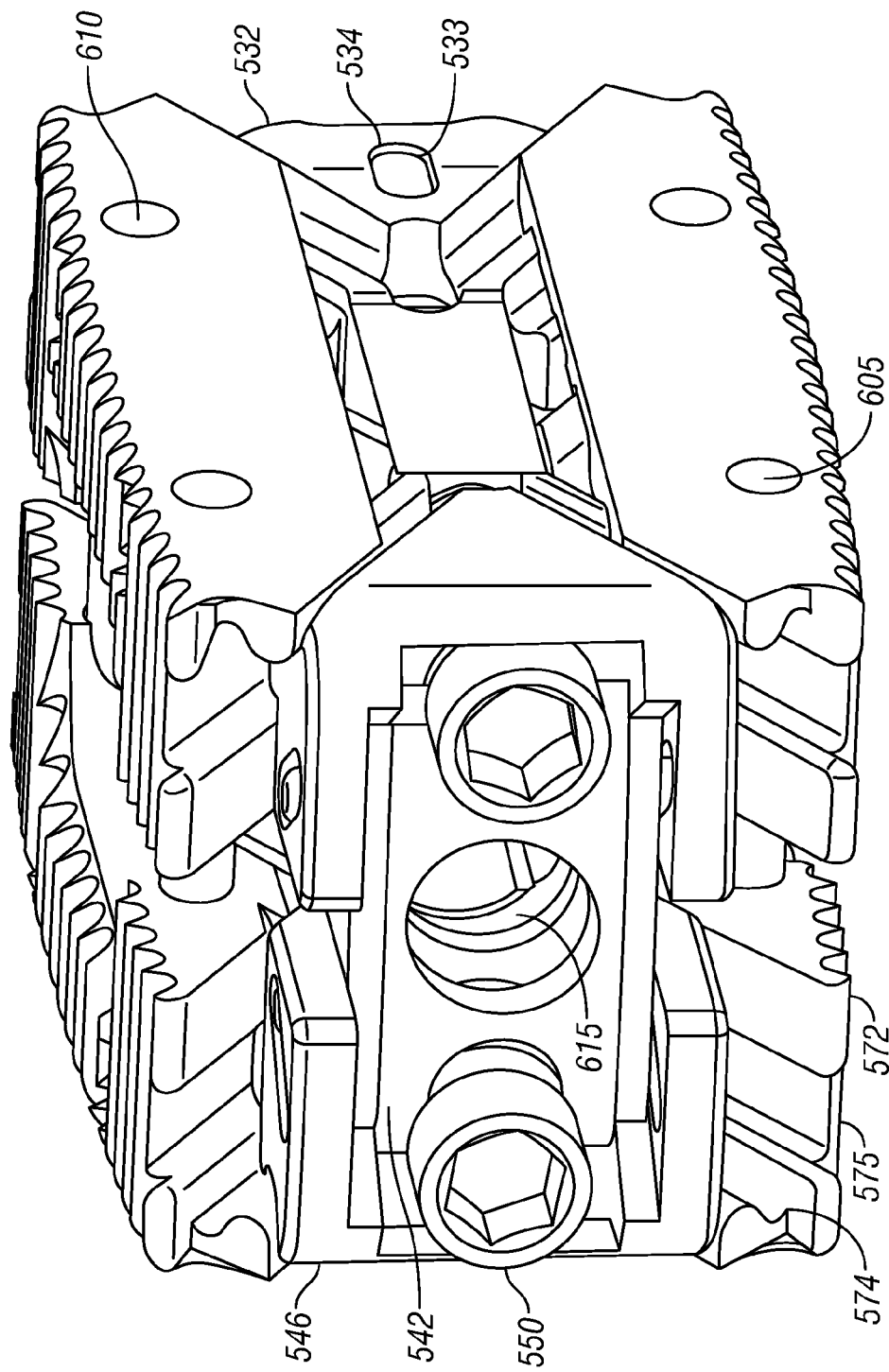
FIG. 73 is an angled perspective view of the expandable fusion device in the expanded position in accordance with one alternative embodiment.

In an exemplary embodiment, FIGS. 71(a)-71(c) depict bone graft hole 615 in the upper and lower endplates 570, 580. Bone graft hole 615 in conjunction with the threaded instrument opening 561 provides space for bone grafts that may used in the intervertebral fusion procedure.

A method of installing the expandable fusion device 10 of FIGS. 66-72 is now discussed in accordance with one embodiment of the present invention. Prior to insertion of the fusion device, the disc space may be prepared as described above. The expandable fusion device 10 can then be inserted into and seated in the appropriate position in the intervertebral disc space. In an embodiment, the device 10 is assembled prior to insertion. The expandable fusion device 10 can be introduced into the intervertebral space, with the end having the first end of the front sloped actuator 450 being inserted. In an exemplary method, the fusion device 10 is in the unexpanded position when introduced into the intervertebral space. In an exemplary method, the intervertebral space may be distracted prior to insertion of the fusion device 10. The distraction provide some benefits by providing greater access to the surgical site making removal of the intervertebral disc easier and making scraping of the endplates of the vertebral bodies 2, 3 easier as depicted in FIG. 1.

With the fusion device 10 inserted into and seated in the appropriate position in the intervertebral disc space, the fusion device 10 can then expand into the expanded position. To expand fusion device 10, a threaded instrument is inserted into the threaded instrument opening 561 and the threaded instrument opening 539 of the rear sloped actuator assembly 540 and the front sloped actuator assembly 530 respectively. The threaded instrument is rotated in the first direction, drawing the front sloped actuator assembly 530 and the rear sloped actuator 540 together and contracting the collective actuator assembly 520. In an exemplary embodiment the front sloped actuator assembly 530 and the rear sloped actuator assembly 540 are drawn together in a linear fashion with the threads of the threaded instrument opening 539 of the front sloped actuator assembly 530 engaging the surface threads 561 of the threaded instrument 560 as a means for controlling the movement of the contraction of the collective actuator assembly 520 and consequently the horizontal expansion of the upper 570 and lower 580 endplates, which expand horizontally with contraction of the collective actuator assembly 520. When horizontal expansion of endplates 570 and 580 has reached its maximum, threaded locking screws 550 may be rotated in a first direction simultaneously to further draw the front actuator assembly 530 towards the rear actuator assembly 540. This contraction of the collective actuator assembly 520 expands the upper 570 and lower 580 endplates until they reach their maximum vertical expansion.

It should also be noted that the expansion of the upper 570 and lower 580 endplates may be varied based on the differences in the dimensions of the sloped surfaces 537 and 547. As best seen in FIG. 16, the upper 570 and lower 580 endplates may be expanded in any of the following ways: straight rise expansion, straight rise expansion followed by a toggle into a lordotic expanded configuration, or a phase off straight rise into a lordotic expanded configuration.

Although the preceding discussion only discussed having a single fusion device 10 in the intervertebral space, it is contemplated that more than one fusion device 10 can be inserted in the intervertebral space. It is further contemplated that each fusion device 10 does not have to be finally installed in the fully expanded state. Rather, depending on the location of the fusion device 10 in the intervertebral disc space, the height of the fusion device 10 may vary from unexpanded to fully expanded. It should be noted that, as well as the height being varied from an unexpanded state to an expanded state, the fusion 10 may be positioned permanently anywhere between the expanded state and the unexpanded state.

The invention being thus described, it will be obvious that the same may be varied in many ways. Such variations are not to be regarded as a departure from the spirit and scope of the invention, and all such modifications as would be obvious to one skilled in the art are intended to be included within the scope of the following claims. Although individual embodiments are discussed, the invention covers all combinations of all those embodiments.

What is claimed is:

1. An intervertebral implant comprising:
an upper endplate comprising a first upper endplate portion and a second upper endplate portion;
a lower endplate comprising a first lower endplate portion and a second lower endplate portion;
a front sloped actuator configured to movingly engage a front end of the upper endplate and a front end of the lower endplate, the front sloped actuator comprising a front height actuator and a front width actuator; and
a rear sloped actuator configured to movingly engage a rear end of the upper endplate and a rear end of the lower endplate, the rear sloped actuator comprising a rear height actuator and a rear width actuator;
wherein the intervertebral implant is configured to transition from a collapsed configuration having a first height and a first width to an expanded configuration having a second height and a second width, non-symmetrically,
wherein the second height is greater than the first height and the second width is greater than the first width, and
wherein actuation of the front and rear width actuators transition the intervertebral implant from the first width to the second width and actuation of the front and rear height actuators transition the intervertebral implant from the first height to the second height such that the expansion of the implant from the first width to the second width is independent of the expansion of the implant from the first height to the second height.

2. The intervertebral implant of claim 1:
wherein the first upper endplate portion and the second upper endplate portion each comprise a front ramped surface in moving engagement with the front sloped actuator and a rear ramped surface in moving engagement with the rear sloped actuator, and
wherein the second lower endplate portion and the second upper endplate portion each comprise a front ramped surface in moving engagement with the front sloped actuator and a rear ramped surface in moving engagement with the rear sloped actuator.

3. The intervertebral implant of claim 1:
wherein the first upper endplate portion and the second upper endplate portion each comprise a front ramped surface and a rear ramped surface;
wherein the second lower endplate portion and the second upper endplate portion each comprise a front ramped surface and a rear ramped surface;
wherein the front sloped actuator comprises opposing sloped surfaces in engagement with the front ramped surface of the first upper endplate portion, the front ramped surface of the second upper endplate portion, the front ramped surface of the first lower endplate portion, and the front ramped surface of the second lower endplate portion; and
wherein the rear sloped actuator comprises opposing sloped surfaces in engagement with the rear ramped surface of the first upper endplate portion, the rear ramped surface of the second upper endplate portion, the rear ramped surface of the first lower endplate portion, and the rear ramped surface of the second lower endplate portion.

4. The intervertebral implant of claim 1:
wherein the first upper endplate portion and the second upper endplate portion each comprise a front ramped surface and a rear ramped surface;
wherein the second lower endplate portion and the second upper endplate portion each comprise a front ramped surface and a rear ramped surface;
wherein the front sloped actuator comprises opposing sloped surfaces that each comprise a pair of elevated tongues that are at an angle that directs away from the center of the intervertebral implant, wherein the elevated tongues engage corresponding slots in the front ramped surface of the first upper endplate portion, the front ramped surface of the second upper endplate portion, the front ramped surface of the first lower endplate portion, and the front ramped surface of the second lower endplate portion; and
wherein the rear sloped actuator comprises opposing sloped surfaces that each comprise a pair of elevated tongues that are at an angle that directs away from the center of the intervertebral implant, wherein the elevated tongues engage corresponding slots in the rear ramped surface of the first upper endplate portion, the rear ramped surface of the second upper endplate portion, the rear ramped surface of the first lower endplate portion, and the rear ramped surface of the second lower endplate portion.

5. The intervertebral implant of claim 1, wherein the upper endplate comprises endplate pins that connect the first upper endplate portion and the second upper endplate portion, and wherein the lower endplate comprises endplate pins that connect the first lower endplate portion and the second lower endplate portion.

6. The intervertebral implant of claim 1, further comprising a linear actuator that extends through an opening in the rear sloped actuator to engage an extension of the front sloped actuator.

7. The intervertebral implant of claim 1, further comprising a linear actuator comprising a head portion and an extension, wherein the extension extends through an opening in the rear sloped actuator to engage an extension of the front sloped actuator.

8. The intervertebral implant of claim 1, wherein the front sloped actuator comprises opposing sloped surfaces, and wherein the rear sloped actuator comprises opposing sloped surfaces.

9. The intervertebral implant of claim 1, wherein the first upper endplate portion and the second upper endplate portion are opposing mirrored halves of the upper endplate, and wherein the first lower endplate portion and the second lower endplate portion are opposing mirrored halves of the lower endplate.

10. An intervertebral implant comprising:
an upper endplate comprising:
a first upper endplate portion comprising a front ramped surface and a rear ramped surface;
a second upper endplate portion comprising a front ramped surface and a rear ramped surface; and
upper endplate pins connecting the first upper endplate portion and the second upper endplate portion;
a lower endplate comprising:
a first lower endplate portion comprising a front ramped surface and a rear ramped surface;
a second lower endplate portion comprising a front ramped surface and a rear ramped surface; and
lower endplate pins connecting the first lower endplate portion and the second lower endplate portion;
a front sloped actuator configured to movingly engage the front ramped surface of the first upper endplate portion, the front ramped surface of the second upper endplate portion, the front ramped surface of the first lower endplate portion, and the front ramped surface of the second lower endplate portion, the front sloped actuator comprising a front height actuator and a front width actuator; and
a rear sloped actuator configured to movingly engage the rear ramped surface of the first upper endplate portion, the front ramped surface of the second upper endplate portion, the rear ramped surface of the first lower endplate portion, and the rear ramped surface of the second lower endplate portion, the rear sloped actuator comprising a rear height actuator and a rear width actuator;
wherein the intervertebral implant is configured to transition from a collapsed configuration having a first height and a first width to an expanded configuration having a second height and a second width,
wherein actuation of the front and rear width actuators transition the intervertebral implant from the first width to the second width and actuation of the front and rear height actuators transition the intervertebral implant from the first height to the second height such that the expansion of the implant from the first width to the second width is independent of the expansion of the implant from the first height to the second height.

11. The intervertebral implant of claim 10:
wherein the front sloped actuator comprises opposing sloped surfaces that each comprise a pair of elevated tongues that are at an angle that directs away from the center of the intervertebral implant, wherein the elevated tongues engage corresponding slots in the front ramped surface of the first upper endplate portion, the front ramped surface of the second upper endplate portion, the front ramped surface of the first lower endplate portion, and the front ramped surface of the second lower endplate portion; and
wherein the rear sloped actuator comprises opposing sloped surfaces that each comprise a pair of elevated tongues that are at an angle that directs away from the center of the intervertebral implant, wherein the elevated tongues engage corresponding slots in the rear ramped surface of the first upper endplate portion, the rear ramped surface of the second upper endplate portion, the rear ramped surface of the first lower endplate portion, and the rear ramped surface of the second lower endplate portion.

12. The intervertebral implant of claim 10, further comprising a linear actuator that extends through an opening in the rear sloped actuator to engage an extension of the front sloped actuator.

13. The intervertebral implant of claim 10, further comprising a linear actuator comprising a head portion and an extension, wherein the extension extends through an opening in the rear sloped actuator to engage an extension of the front sloped actuator.

14. The intervertebral implant of claim 10, wherein the front sloped actuator comprises opposing sloped surfaces, and wherein the rear sloped actuator comprises opposing sloped surfaces.

15. A method of installing the intervertebral implant according to claim 1, the method comprising:
introducing the intervertebral implant of claim 1 into an intervertebral space; and
contracting the front sloped actuator and the rear sloped actuator to cause the intervertebral implant to transition from a collapsed configuration having a first height and a first width to an expanded configuration having a second height and a second width.

16. The method of claim 15, wherein the step of contracting comprises drawing the front sloped actuator and the rear sloped actuator together such that the upper endplate and the lower endplate of the intervertebral implant are forced vertically outward from one another, a first portion of the upper endplate and a second portion of the upper endplate are forced laterally outward from another, and a first portion of the lower endplate and a second portion of the lower endplate are forced laterally outward from one another.

17. The method of claim 15, wherein the step of contracting comprises rotating a linear actuator to draw the front sloped actuator and a rear sloped actuator together, the linear actuator being in engagement with the front sloped actuator.

18. The method of claim 16, wherein contracting the actuator assembly comprises: (i) moving the front sloped actuator such that opposing ramped surfaces of the front sloped actuator engage front ramped surfaces in an upper endplate and engage front ramped surfaces in a lower endplate; and (ii) moving the rear sloped actuator such that opposing ramped surfaces of the rear sloped actuator engage rear ramped surfaces in the upper endplate and engage rear ramped surfaces in the lower endplate, wherein moving the front sloped actuator and moving the rear sloped actuator force the upper and lower endplate outward and away from one another, cause the upper endplate and the lower endplate to each expand laterally.

19. The method of claim 18, wherein the opposing ramped surfaces of the front sloped actuator comprise elevated tongues that are angled at a slant that directs away from the center of the intervertebral implant and ride in corresponding slots in the front ramped surfaces of the upper and lower endplates, and wherein the opposing ramped surfaces of the rear sloped actuator comprise elevated tongues that are angled at a slant that directs away from the center of the intervertebral implant and ride in corresponding slots in the rear ramped surfaces of the upper and lower endplates.

* * * * *